US011919930B2

(12) United States Patent
Takahashi et al.

(10) Patent No.: US 11,919,930 B2
(45) Date of Patent: Mar. 5, 2024

(54) ODORANT RECEPTOR CO-RECEPTOR

(71) Applicant: Sumitomo Chemical Company, Limited, Tokyo (JP)

(72) Inventors: Yasuhiko Takahashi, Osaka (JP); Tomoyuki Takaku, Tokyo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 661 days.

(21) Appl. No.: 16/338,245

(22) PCT Filed: Sep. 26, 2017

(86) PCT No.: PCT/JP2017/034792
§ 371 (c)(1),
(2) Date: Mar. 29, 2019

(87) PCT Pub. No.: WO2018/062203
PCT Pub. Date: Apr. 5, 2018

(65) Prior Publication Data
US 2019/0225659 A1 Jul. 25, 2019

(30) Foreign Application Priority Data
Sep. 29, 2016 (JP) .................. 2016-191904

(51) Int. Cl.
C07K 14/705 (2006.01)
C07K 14/435 (2006.01)
G01N 33/00 (2006.01)
C12N 15/85 (2006.01)
C07K 19/00 (2006.01)
C12N 15/09 (2006.01)
C12N 5/10 (2006.01)

(52) U.S. Cl.
CPC ...... *C07K 14/43581* (2013.01); *C07K 14/705* (2013.01); *C07K 19/00* (2013.01); *C12N 5/10* (2013.01); *C12N 15/09* (2013.01); *C12N 15/85* (2013.01); *G01N 33/0004* (2013.01); *C12N 2015/859* (2013.01)

(58) Field of Classification Search
None
See application file for complete search history.

(56) References Cited

U.S. PATENT DOCUMENTS

| | | | |
|---|---|---|---|
| 2004/0235060 A1 | 11/2004 | Dhanasekaran et al. | |
| 2005/0053933 A1 | 3/2005 | Lee et al. | |
| 2011/0112179 A1* | 5/2011 | Airan ............... | A61P 43/00 514/44 R |
| 2013/0065244 A1 | 3/2013 | Suzuki et al. | |
| 2015/0276710 A1 | 10/2015 | Kitajima et al. | |

FOREIGN PATENT DOCUMENTS

| | | |
|---|---|---|
| CN | 102811615 A | 12/2012 |
| CN | 103097408 A | 5/2013 |
| CN | 104602523 A | 5/2015 |
| CN | 104640448 A | 5/2015 |
| JP | 2005510209 A | 4/2005 |
| JP | 2015192664 | 11/2015 |
| WO | 0050566 A2 | 8/2000 |
| WO | 03016477 A2 | 2/2003 |
| WO | 03020913 A2 | 3/2003 |

OTHER PUBLICATIONS

Zhao et al. (2014) Journal Genetics 93: 53-61. (Year: 2014).*
Extended European Search Report dated Mar. 23, 2020 in EP Application No. 17856153.6.
Krautwurst et al., "Identification of ligands for olfactory receptors by functional expression of a receptor library," Cell, Elsevier, Amsterdam, NL, vol. 95, pp. 917-926, XP002153217 (1998).
Larsson et al., "Or83b encodes a broadly expressed odorant receptor essential for *Drosophila* olfaction," Neuron, vol. 43, No. 5, pp. 703-714, XP002798287 (2004).
Nichols et al., "Transmembrane Segment 3 of *Drosophila melanogaster* Odorant Receptor Subunit 85b Contributes to Ligand-Receptor Interactions," Journal of Biological Chemistry, vol. 285, No. 16, pp. 11854-11862, XP055674352 (2010).
Pellegrino et al., "A natural polymorphism alters odour and DEET sensitivity in an insect odorant receptor," Nature, vol. 478, No. 7370, pp. 511-514, XP055674356 (2011).
Sato et al., "Insect olfactory receptors are heteromeric ligand-gated ion channels," Nature, vol. 452, No. 7190, pp. 1002-1006, XP055674348 (2008).
Office Action dated Apr. 10, 2020 in CN Application No. 201780015437.4
Database UniProt, [online], Accession No. W6GTH2, http://www.uniprot.org/uniprot/W6GTH2, Apr. 16, 2014 uploaded, [retrieved on Dec. 21, 2017], entire text.
English Translation of International Preliminary Report on Patentability dated Apr. 2, 2019 in International Application No. PCT/JP2017/034792; dated Apr. 11, 2019.
Fukutani et al., "The N-terminal replacement of an olfactory receptor for the development of a Yeast-based biomimetic odor sensor," Biotechnol. Bioeng., vol. 109, pp. 205-212 ((2012).
Hope et al., "Molecular determinants of (+)-tubocurarine binding at recombinant 5-hydroxytryptamine3A receptor subunits," Mol. Pharmacol., vol. 55, pp. 1037-1043 (1999).
International Search Report dated Jan. 9, 2018 in International Application No. PCT/JP2017/034792.
Kaupp, U. Benjamin, "Olfactor signalling in vertebrates and insects: differences and commonalities," Nature Reviews Neuroscience, vol. 11, pp. 188-200 (2010).

(Continued)

*Primary Examiner* — Michael D Pak
(74) *Attorney, Agent, or Firm* — Panitch Schwarze Belisario & Nadel LLP; Sandra M. Katz; Stephany G. Small

(57) ABSTRACT

Provided is an insect odorant receptor co-receptor that exhibits excellent detection sensitivity to an odorous substance when bound to an odorant receptor to form an odorant receptor complex. The odorant receptor co-receptor includes a first amino acid sequence and a second amino acid sequence subsequently to the farthest carboxyl-terminal amino acid residue of the first amino acid sequence.

9 Claims, 9 Drawing Sheets

Specification includes a Sequence Listing.

(56) References Cited

OTHER PUBLICATIONS

Melo et al., "Identification of chemosensory receptor from the yellow fever mosquito, *Aedes aegypti,* that is highly conserved and expressed in olfactory and gustatory organs," Chem. Senses, vol. 29, pp. 403-410 (2004).
Mueller et al., "Chimeric FLS2 receptors reveal the basis for differential flagellin perception in *Arabidopsis* and tomato," Plant Cell, vol. 24, pp. 2213-2224 (2012).
Office Action dated Aug. 4, 2020 in JP Application No. 2016191904.
Office Action dated Aug. 30, 2021 in Taiwanese Application No. 106133416.
Office Action dated Apr. 8, 2022 in CN Application No. 201780060791.9.
Qi et al., "Research advances in odorant receptors in insects," Acta Entomological Sinica, vol. 51, No. 1, pp. 75-80 (2008) (with English Abstract).
Shu-Yan et al., "Progress in functions and molecular structure of the atypical insect olfactory receptor Orco," Acta Entomological Sinica, vol. 56, No. 10, pp. 1208-1216 (2013) (with English Abstract).
Yang et al., The Olfactory Co-receptor Orco from the Migratory Locust (*Locusta migratoria*) and the Desert Locust (*Schistocerca gregaria*): Identification and Expression pattern, 8(2) International Journal of Biological Sciences 159-170 (2012).

\* cited by examiner

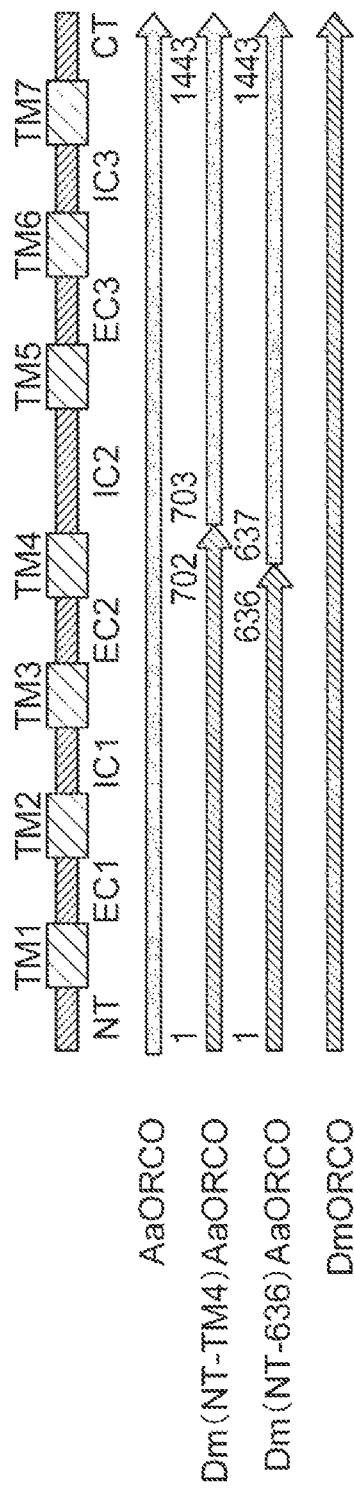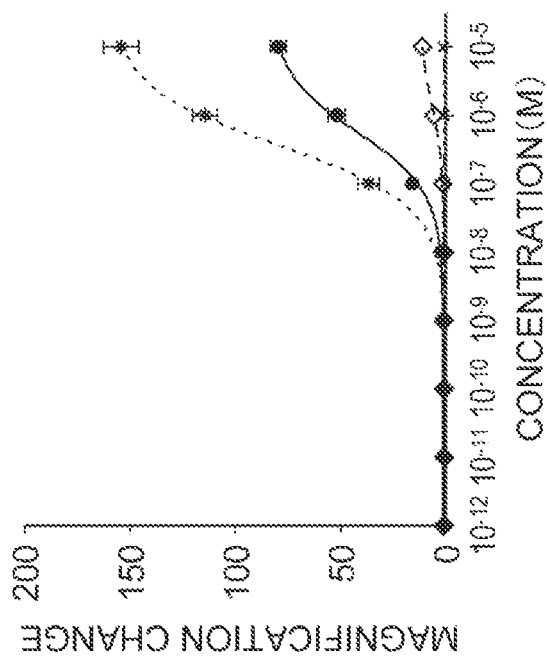
Fig. 4

ODORANT RECEPTOR CO-RECEPTOR

CROSS-REFERENCE TO RELATED APPLICATION

This application is a Section 371 of International Application No. PCT/JP2017/034792, filed Sep. 26, 2017, which was published in the Japanese language on Apr. 5, 2018, under International Publication No. WO 2018/062203 A1, which claims priority under 35 U.S.C. § 119(b) to Japanese Application No. 2016-191904, filed Sep. 29, 2016, and the disclosures of which are incorporated herein by reference.

REFERENCE TO SEQUENCE LISTING SUBMITTED ELECTRONICALLY

This application contains a sequence listing, which is submitted electronically via EFS-Web as an ASCII formatted sequence listing with a file name "688101_82US_Sequence_Listing", creation date of Mar. 29, 2019, and having a size of about 175 KB. The sequence listing submitted via EFS-Web is part of the specification and is herein incorporated by reference in its entirety.

TECHNICAL FIELD

The present invention relates to an odorant receptor co-receptor. The present invention also relates to a polynucleotide encoding an odorant receptor co-receptor, an expression plasmid having the polynucleotide incorporated therein, and a cell having the expression plasmid incorporated therein.

BACKGROUND ART

In recent years, various technologies for measuring volatile chemical substances (odorous substances) are known. Such technologies are expected to be applied to the field of diagnosis and healthcare, such as cancer diagnosis; the field of disaster prevention and security, such as person search and detection of narcotic drugs; the field of environment, such as detection of harmful substances; and the like.

For the detection of an odorous substance, living organisms such as a dog or a nematode may be utilized. However, while methods of utilizing living organisms are capable of detecting an odorous substance with high sensitivity, the methods lack stability, since there are fluctuations depending on the conditions or the individual. Furthermore, since there are limitations in the duration of the power of concentration, it is also considered difficult to utilize the methods for a long time period.

Therefore, attention is being paid not to a living organism itself, but to the olfactory function possessed by the living organism. Particularly, the olfactory function of insects is considered to have high recognition specificity of odorous substances, and a way of utilizing the olfactory function of insects in olfactory sensors and the like is being sought for. In the olfactory organ of an insect, an odorant receptor complex composed of an odorant receptor (hereinafter, may be referred to as "OR") that recognizes odorous substances, and an odorant receptor co-receptor (hereinafter, may be referred to as "ORCO" or "co-receptor"). When the odorant receptor complex is activated by an odorous substance, the complex exhibits ion channel activity, and the odorous substance is detected by that complex (U. Benjamin Kaupp, Nature Reviews Neuroscience, Vol. 11 (2010), p. 188-200).

SUMMARY OF INVENTION

Technical Problem

However, in a case in which it is intended to detect an odorous substance in the field, the concentration of the odorous substance may be very low. Therefore, an olfactory sensor that is used for detecting an odorous substance is required to be highly sensitive.

The present invention was achieved in view of the above-described circumstances, and it is an object of the invention to provide an odorant receptor co-receptor that exhibits excellent detection sensitivity for an odorous substance when bound to an odorant receptor to form an odorant receptor complex.

Solution to Problem

The inventors of the present invention conducted an investigation on chimeric odorant receptor co-receptors obtained by recombining two insect odorant receptor co-receptors of different varieties, and as a result, the inventors found that in a case in which the position of recombination of the two kinds of odorant receptor co-receptors is in the vicinity of the farthest carboxyl-terminal amino acid residue of the fourth transmembrane domain in the odorant receptor co-receptor, the odorant receptor complex having the chimeric odorant receptor co-receptor thus obtained has superior detection sensitivity- to an odorous substance compared to an odorant receptor complex having the original odorant receptor co-receptor. The invention is based on these findings.

That is, the invention relates to, for example, the following items [1] to [17].

[1] An odorant receptor co-receptor including the following first amino acid sequence and the following second amino acid sequence subsequent to the farthest carboxyl-terminal amino acid residue of the first amino acid sequence:

(1) a first amino acid sequence, which is a partial amino acid sequence of an odorant receptor co-receptor of a first insect or a variant of the co-receptor, the partial amino acid sequence being an amino acid sequence that is contiguous from the amino-terminus of the odorant receptor co-receptor of the first insect or a variant of the co-receptor to any amino acid residue positioned in the range of twenty amino acid residues before and after the farthest carboxyl-terminal amino acid residue of the fourth transmembrane domain; and (2) a second amino acid sequence, which is a partial amino acid sequence of an odorant receptor co-receptor of a second insect of a variety different from the first insect or a variant of the co-receptor, the partial amino acid sequence being an amino acid sequence that is contiguous from an amino acid residue at a position that is one position carboxyl-terminal to a position corresponding, in an alignment analysis of the amino acid sequence of the first insect odorant receptor co-receptor or the variant thereof and the amino acid sequence of the second insect odorant receptor co-receptor or the variant thereof, to the farthest carboxyl-terminal amino acid residue of the first amino acid sequence in the odorant receptor co-receptor of the second insect or a variant of the co-receptor, to the carboxyl-terminus of the odorant receptor co-receptor of the second insect or a variant of the co-receptor.

[2] The odorant receptor co-receptor according to [1], in which the first insect and the second insect are insects of different varieties selected from the group consisting of insects of the superorder Endopterygota.

[3] The odorant receptor co-receptor according to [1] or [2], in which the first insect and the second insect are insects of different varieties selected from the group consisting of insects of the order Diptera, insects of the order Lepidoptera, and insects of the order Hymenoptera.

[4] The odorant receptor co-receptor according to any one of [1] to [3], in which the first insect and the second insect are insects of different varieties selected from the group consisting of insects of the genus *Culicidae*, insects of the genus *Drosophilidae*, insects of the genus *Bombycidae*, and insects of the genus *Apidae*.

[5] The odorant receptor co-receptor according to any one of [1] to [4], in which the first insect is any one insect from among *Aedes aegypti, Anopheles gambiae*, and *Drosophila melanogaster*.

[6] The odorant receptor co-receptor according to any one of [1] to [5], in which the first amino acid sequence is an amino acid sequence having an identity of 90% or higher with an amino acid sequence set forth in any one of SEQ ID NO:1, SEQ ID NO:135, or SEQ ID NO:136.

[7] The odorant receptor co-receptor according to any one of [1] to [6], in which the second insect is any one insect from among *Aedes aegypti* and *Apis mellifera*.

[8] The odorant receptor co-receptor according to any one of [1] to [7], in which the second amino acid sequence is an amino acid sequence having an identity of 90% or higher with the amino acid sequence set forth in SEQ ID NO:2 or SEQ ID NO:137.

[9] The odorant receptor co-receptor according to any one of [1] to [4], in which the first insect is *Drosophila melanogaster*, and the second insect is *Apis mellifera*.

[10] The odorant receptor co-receptor according to [9], including an amino acid sequence having an identity of 90% or higher with the amino acid sequence set forth in SEQ ID NO:100.

[11] The odorant receptor co-receptor according to any one of [1] to [4], in which the first insect is *Drosophila melanogaster*, and the second insect is *Aedes aegypti*.

[12] The odorant receptor co-receptor according to [11], including an amino acid sequence having an identity of 90% or higher with the amino acid sequence set forth in SEQ NO:71.

[13] The odorant receptor co-receptor according to any one of [1] to [4], in which the first insect is *Aedes aegypti*, and the second insect is *Apis mellifera*.

[14] The odorant receptor co-receptor according to [13], including an amino acid sequence having an identity of 90% or higher with the amino acid sequence set forth in SEQ ID NO:108.

[15] A polynucleotide encoding the odorant receptor co-receptor according to any one of [1] to [14].

[16] An expression plasmid having the polynucleotide according to [15] incorporated therein.

[17] A cell having the polynucleotide according to [15] or the expression plasmid according to [16] incorporated therein.

Advantageous Effects of Invention

According to the present invention, a chimeric odorant receptor co-receptor that exhibits excellent detection sensitivity to odorous substances when bound to an odorant receptor to form an odorant receptor complex, can be provided. The odorant receptor complex having the chimeric odorant receptor co-receptor of the invention exhibits superior detection sensitivity to odorous substances compared to an odorant receptor complex having each one of two kinds of odorant receptor co-receptors which are origin of the chimeric odorant receptor co-receptors. The invention can also provide a polynucleotide encoding the chimeric odorant receptor co-receptor according to the invention, an expression plasmid having the polynucleotide incorporated therein, and a cell having the polynucleotide or the expression plasmid incorporated therein.

BRIEF DESCRIPTION OF DRAWINGS

FIG. 4 shows the relative value of the amount of luminescence detected when 1-octet-3-ol was added to a cell that expresses AaOR8 as an odorant receptor and expresses any one of AaORCO, DmORCO, or various chimeric co-receptors Dm-AaORCO) as a co-receptor.

DESCRIPTION OF EMBODIMENTS

Figure 1:
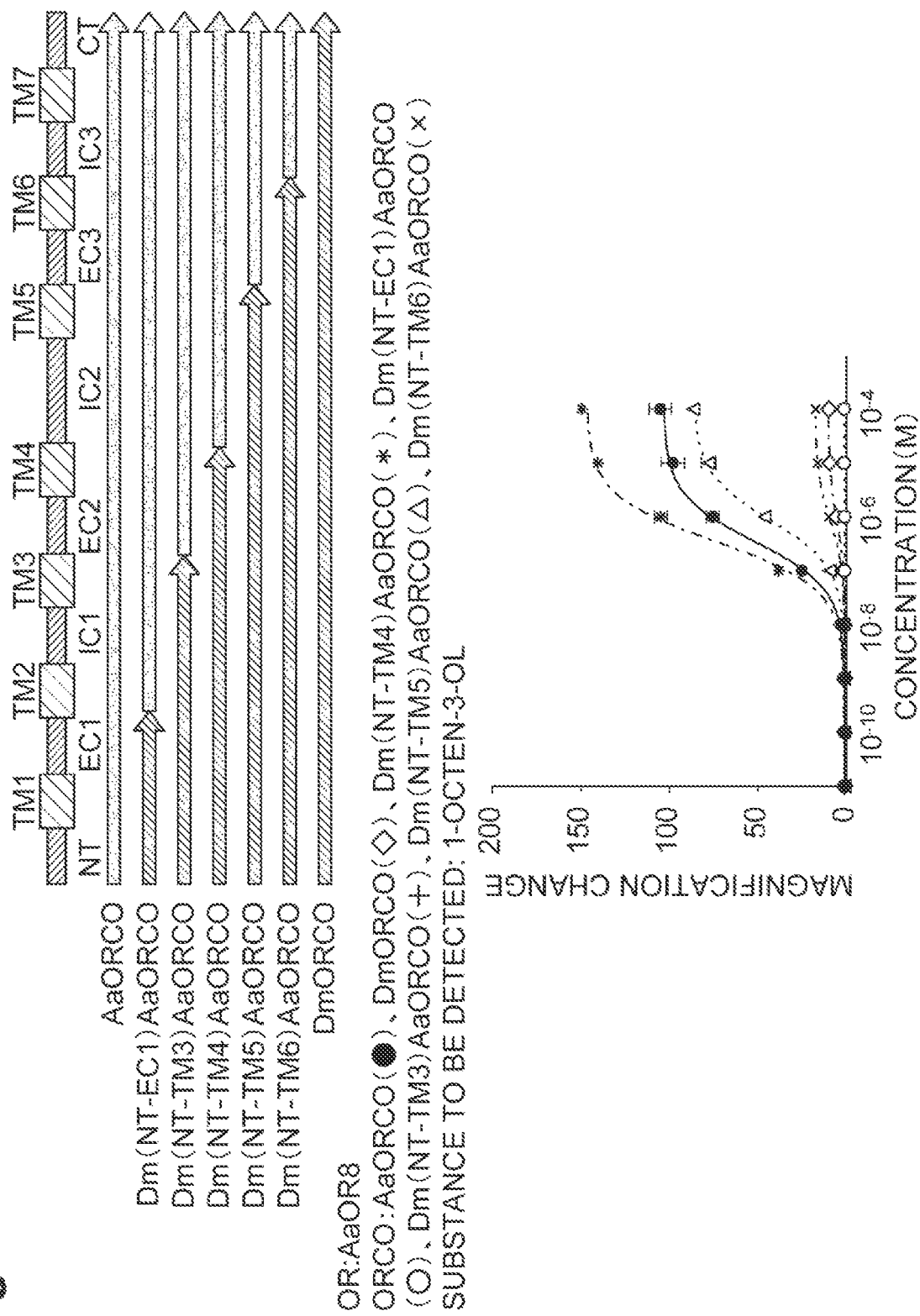
FIG. 1 shows the relative value of the amount of luminescence detected when 1-octen-3-ol was added to a cell that expresses AaOR8 as an odorant receptor and expresses any one of AaORCO, DmORCO, or various chimeric co-receptors (Dm-AaORCO) having different positions of recombination as a co-receptor.

In the following description, embodiments for carrying out the present invention (hereinafter, referred to as "present embodiments") will be explained in detail. However, the invention is not intended to be limited to the following embodiments.

Odorant receptors of insects constitute a class of G protein-coupled receptors having a seven-transmembrane structure and the recognition specificity of the odorant receptors to odorants is high Several odorant-specific odorant receptors are known.

While an odorant receptor co-receptor of an insect is a membrane protein having a seven-transmembrane structure as in the case of an odorant receptor, the odorant receptor co-receptor itself does not recognize odorous substances and functions by forming a hetero-complex with an odorant receptor. The odorant receptor co-receptors are conserved in all insects and are known as Orco family. Many of the odorant receptor co-receptors of the Orco family are each composed of, from the amino-terminus (hereinafter, may be referred to as "N-terminus") toward the carboxyl-terminal (hereinafter, may be referred to as "C-terminus"), an N-terminal domain (NT), a first transmembrane domain (TM1), a first extracellular loop (EC1), a second transmembrane domain (TM2), a first intracellular loop (IC1), a third transmembrane domain (TM3), a second extracellular loop (EC2), a fourth transmembrane domain (TM4), a second intracellular loop (IC2), a fifth transmembrane domain (TM5), a third extracellular loop (EC3), a sixth transmembrane domain (TM6), a third intracellular loop (IC3), a seventh transmembrane domain (TM7), and a C-terminal domain (CT), linked in the above order.

An odorant receptor complex, which is a hetero complex composed of the above-mentioned odorant receptor and the above-mentioned odorant receptor co-receptor, has ion channel activity that is activated by an odorous substance. When the odorant receptor complex is activated, the odorant receptor complex causes cations such as sodium ions ($Na^+$) and calcium ions ($Ca^{2+}$) to flow into cells.

The odorant receptor co-receptor of the present embodiment includes, in order from its N-terminus, a first amino acid sequence that is a partial amino acid sequence of an odorant receptor co-receptor of a first insect or a variant of the co-receptor; and a second amino acid sequence that is a partial amino acid sequence of an odorant receptor co-receptor of a second insect of variety different from the first insect or a variant of the co-receptor. That is, the odorant receptor co-receptor of the present embodiment includes a first amino acid sequence, and subsequent to the farthest C-terminal amino acid residue of the first amino acid sequence, a second amino acid sequence.

The term "variant" according to the present specification refers to a protein that retains the function as a co-receptor compared to an intended protein, but has several different amino acid residues compared to the amino acid sequence of the intended protein. Specifically, a variant may have one to ten different amino acid residues, may have one to five different amino acid residues, or may have one or two different amino acid residues. Such variation of amino acid residues may be specifically deletion, substitution, addition, and the like of amino acid variation. These include deletion, substitution, addition, and the like of amino acids occurring as a result of genetic mutations naturally occurring due to species differences, individual differences, or the like of the living organism from which the co-receptor is derived, as well as genetic mutations that are artificially introduced. The substitution of an amino acid may be, for example, conservative substitution with an amino acid having similar features in hydrophobicity, electric charge, pK, and the steric structure.

The first insect and the second insect are insects of varieties different from each other. The first insect and the second insect may be insects of the superorder Endopterygota. Examples of the insects of the superorder Endopterygota include the order Diptera such as the genus *Culicidae* and the genus *Drosophilidae*; the order Lepidoptera such as the genus *Bombycidae*; and the order Hymenoptera such as the genus *Apidae*. The first insect and the second insect may be insects of different varieties selected from the group consisting of insects of the order Diptera, insects of the order Lepidoptera, and insects of the order Hymenoptera. Examples of the insects of the genus *Culicidae* include *Anopheles gambiae, Aedes aegypti,* and *Culex quinquefasciatus*. Examples of the insects of the genus *Drosophilidae* include *Drosophila melanogaster, Drosophila pseudoobscura,* and *Drosophila virillis*. Examples of the genus *Bombycidae* include *Bombyx mori, Bombyx mandarina,* and *Trilocha varians*. Examples of the insects of the genus *Apidae* include *Apis mellifera, Apis florea, Apis dorsata,* and *Bombus terrestris*.

The first insect is preferably *Aedes aegypti, Anopheles gambiae,* or *Drosophila melanogaster*. The second insect is preferably *Aedes aegypti* or *Apis mellifera*. The first insect and the second insect may be arbitrarily combined as long as the insects are insects of varieties different from each other. A specific combination of the first insect and the second insect may be, for example, a combination of *Drosophila melanogaster* as the first insect and *Apis mellifera* as the second insect; a combination of *Drosophila melanogaster* as the first insect and *Aedes aegypti* as the second insect; or a combination of *Aedes aegypti* as the first insect and *Apis mellifera* as the second insect.

In regard to the odorant receptor co-receptor of the present embodiment, the first amino acid sequence is an amino acid sequence that is contiguous from the N-terminus of an odorant receptor co-receptor of a first insect or a variant of the co-receptor, to several amino acid residues positioned in the range of twenty amino acid residues before and after the farthest C-terminal amino acid residue of the fourth transmembrane domain. That is. the first amino acid sequence is an amino acid sequence including from the N-terminal domain (NT) of an odorant receptor co-receptor of a first insect or a variant of the co-receptor, with a first transmembrane domain (TM1), a first extracellular loop (EC1), a second transmembrane domain (TM2), a first intracellular loop (IC1), a third transmembrane domain (TM3), and a second extracellular loop (EC2) being subsequently disposed, to any one amino acid residue positioned in the range of twenty amino acid residues before and after the farthest C-terminal amino acid residue of the fourth transmembrane domain (TM4). The farthest C-terminal amino acid residue of the first amino acid sequence may be any one amino acid residue positioned in the range of twenty amino acid residues before and after the farthest C-terminal amino acid residue of the fourth transmembrane domain in the odorant receptor co-receptor of the first insect or a variant of the co-receptor; may be any one amino acid residue positioned in the range of fifteen amino acid residues before and after the farthest C-terminal amino acid residue of the fourth transmembrane domain; may be any one amino acid residue positioned in the range of ten amino acid residues before and after the farthest C-terminal amino acid residue of the fourth transmembrane domain; may be any one amino acid residue positioned in the range of five amino acid residues before and after the amino acid residue furthest C-terminal side of the fourth transmembrane domain; or may be the farthest C-terminal amino acid residue of the fourth transmembrane domain.

The first amino acid sequence may be, for example, an amino acid sequence having an identity of 90% or higher with an amino acid sequence that is contiguous from the N-terminal amino acid residue of the N-terminal domain of an odorant receptor co-receptor of *Drosophila melanogaster* to the farthest C-terminal amino acid residue of the fourth transmembrane domain (SEQ ID NO:1), or the first amino acid sequence may be an amino acid sequence having an identity of 95% or higher therewith; may be an amino acid sequence having an identity of 98% or higher therewith; may be an amino acid sequence having an identity of 99% or higher therewith; or may be a 100% identical amino acid sequence.

The first amino acid sequence may be, for example, an amino acid sequence having an identity of 90% or higher with an amino acid sequence that is contiguous from the N-terminal amino acid residue of the N-terminal domain of an odorant receptor co-receptor of *Aedes aegypti* to the farthest C-terminal amino acid residue of the fourth transmembrane domain (SEQ ID NO:135), or the first amino acid sequence may be an amino acid sequence having an identity of 95% or higher therewith; may be an amino acid sequence having an identity of 98% or higher, therewith; may be an amino acid sequence having an identity of 99% or higher therewith; or may be a 100% identical amino acid sequence.

The first amino acid sequence may be, fix example, an amino acid sequence having an identity of 90% or higher with an amino acid sequence that is contiguous from the N-terminal amino acid residue of the N-terminal domain of an odorant receptor co-receptor of *Anopheles gambiae* to the farthest C-terminal amino acid residue of the fourth transmembrane domain (SEQ ID NO:136), or the first amino acid sequence may be an amino acid sequence having an identity of 95% or higher therewith; may be an amino acid sequence having an identity of 98% or higher therewith; may be an amino acid sequence having an identity of 99% or higher therewith; or may be a 100% identical amino acid sequence.

In regard to the odorant receptor co-receptor of the present embodiment, the second amino acid sequence is an amino acid sequence that is contiguous from an amino acid residue at a position that is one position C-terminal to a position corresponding, in an alignment analysis of the amino acid sequence of the first insect odorant receptor co-receptor or the variant thereof and the amino acid sequence of the second insect odorant receptor co-receptor or the variant thereof, to the farthest C-terminal amino acid residue of the first amino acid sequence in the odorant receptor co-receptor of the second insect or a variant of the co-receptor, to the C-terminus of the odorant receptor co-receptor of the second insect or a variant of the co-receptor. The second amino acid sequence is, for example, an amino acid sequence including from any one amino acid residue positioned in the range of about twenty amino acid residues before and after the farthest N-terminal amino acid residue of the second intracellular loop (IC2) of the odorant receptor co-receptor of the second insect or a variant of the co-receptor, with a fifth transmembrane domain (TM5), a third extracellular loop (EC3), a sixth transmembrane domain (TM6), a third intracellular loop (IC3), and a seventh transmembrane domain (TM7) being subsequently disposed, to the C-terminal domain (CT).

That is, the odorant receptor co-receptor of the present embodiment having the first amino acid sequence and the second amino acid sequence is such that the amino acid sequence at a position corresponding to the second amino acid sequence in the odorant receptor co-receptor of the first insect has been replaced with the amino acid sequence of the odorant receptor co-receptor of the second insect. Any duplication or deletion in the amino acid, residue at a corresponding position in an alignment of the amino acid sequences of the original two kinds of odorant receptor co-receptors does not exist between the first amino acid sequence and the second amino acid sequence.

The second amino acid sequence may be, for example, an amino acid sequence having an identity of 90% or higher with an amino acid sequence that is contiguous from the farthest N-terminal amino acid residue of the second intracellular loop of an odorant receptor co-receptor of *Apis mellifera* to the C-terminal amino acid residue of the C-terminal domain (SEQ ID NO:2), or the second amino acid sequence may be an amino acid sequence having an identity of 95% or higher therewith; may be an amino acid sequence having an identity of 98% or higher therewith; may be an amino acid sequence having an identity of 99% or higher therewith; or may be a 100% identical amino acid sequence.

The second amino acid sequence may be, for example, an amino acid sequence having an identity of 90% or higher with an amino acid sequence that is contiguous from the farthest N-terminal amino acid residue of the second intracellular loop of an odorant receptor co-receptor of *Aedes aegypti* to the C-terminal amino acid residue of the C-terminal domain (SEQ ID NO:137), or the second amino acid sequence may be an amino acid sequence having an identity of 95% or higher therewith; may be an amino acid sequence having an identity of 98% or higher therewith; may be an amino acid sequence having an identity of 99% or higher therewith; or may be a 100% identical amino acid sequence.

The chimeric odorant receptor co-receptor of the present embodiment includes a first amino acid sequence and a second amino acid sequence and is composed of from about 460 to about 500 amino acid residues. The chimeric odorant receptor co-receptor of the present embodiment is composed of an N-terminal domain (NT), a first transmembrane domain (TM1), a first extracellular loop (EC1), a second transmembrane domain (TM2), a first intracellular loop (IC1), a third transmembrane domain (TM3), a second extracellular loop (EC2), a fourth transmembrane domain (TM4), a second intracellular loop (IC2), a fifth transmembrane domain (TM5), a third extracellular loop (EC3), a sixth transmembrane domain (TM6), a third intracellular loop (IC3), a seventh transmembrane domain (TM7), and a C-terminal domain (CT), linked in the above order from the N-terminus toward the C-terminus in the following order.

The chimeric odorant receptor co-receptor of the present embodiment has an ability to be coupled with an insect odorant receptor and to cause canons to flow into a cell. The ability of the odorant receptor co-receptor to be coupled with an odorant receptor and to cause cations to flow into a cell can be measured using, for example, cultured cells that co-express an odorant receptor co-receptor of an object of measurement and an insect odorant receptor. Specifically, a ligand of the odorant receptor is brought into contact with the cultured cells, and the transient change in the intracellular calcium concentration is measured. When the odorant receptor co-receptor of the object of measurement has the above-described ability, an increase in the intracellular calcium concentration caused by activation of the odorant receptor is detected.

More specific examples of the chimeric odorant receptor co-receptor of the present embodiment include:

an odorant receptor co-receptor in which the first amino acid sequence is a partial amino acid sequence of a co-receptor of *Drosophila melanogaster*, and the second amino acid sequence of a partial amino acid sequence of a co-receptor of *Apis mellifera*;

an odorant receptor co-receptor including an amino acid sequence having an identity of 90% or higher with the amino acid sequence set forth in SEQ ID NO:100;

the above-mentioned odorant receptor co-receptor in which the first amino acid sequence is a partial amino acid sequence of a co-receptor of *Drosophila melanogaster*, and the second amino acid sequence is a partial amino acid sequence of a co-receptor of *Aedes aegypti*;

an odorant receptor co-receptor including an amino acid sequence having an identity of 90% or higher with the amino acid sequence set forth in SEQ ID NO:71;

the above-mentioned odorant receptor co-receptor in which the first amino acid sequence is a partial amino acid sequence of a co-receptor of *Aedes aegypti*, and the second amino acid sequence is a partial amino acid sequence of a co-receptor of *Apis mellifera*; and an odorant receptor co-receptor including an amino acid sequence having an identity of 90% or higher with the amino acid sequence, set forth in SEQ ID NO:108.

Here, the "identity of 90% or higher" may be an identity of at least 90%, 95%, 98%, or 99%, or may be 100% identity.

The odorant receptor co-receptor of the present embodiment can be produced by a method of incorporating a polynucleotide encoding a polypeptide having the first amino acid sequence and a polynucleotide encoding a polypeptide having the second amino acid sequence into one expression plasmid such that these polynucleotides are linked together in frame, incorporating this expression plasmid into a cell to express an intended protein, and then purifying the expressed protein, or the like. The method of expressing an odorant receptor co-receptor in a cell is not particularly limited, and any known method can be used. The ratio (molar ratio) of the DNA fragments at the time of incorporating a polynucleotide encoding a polypeptide having the first amino acid sequence and a polynucleotide encoding a polypeptide having the second amino acid sequence into one expression plasmid, is preferably 1:1. Whether the expression plasmid has been incorporated into a cell can be checked by methods such as PCR. The odorant receptor co-receptor expressed in the cell can be purified by solubilizing the cell membrane and then subjecting the cell mixture to various columns for purification.

When the chimeric odorant receptor co-receptor of the present embodiment is used, superior detection sensitivity to an odorous substance is obtained when the chimeric receptor co-receptor is bound to an odorant receptor to form an odorant receptor complex, compared to the original two kinds of odorant receptor co-receptors. An odorant receptor co-receptor having such characteristics is useful as an olfactory sensor capable of detecting an odorous substance at a lower concentration.

In a case in which an odorant receptor complex is produced by using the odorant receptor co-receptor of the present embodiment together with an odorant receptor, the type of the odorant receptor can be selected as appropriate according to the targeting ligand. The odorant receptor may be specifically OR8 or OR10 of *Aedes aegypti*, OR10 or OR28 of *Anopheles gambiae*, OR56 of *Bombyx mori*, or OR47a of *Drosophila melanogaster*.

The polynucleotide of the present embodiment encodes the above-described chimeric odorant receptor co-receptor. The polynucleotide of the present embodiment includes a first nucleotide sequence encoding the first amino acid sequence and a second nucleotide sequence encoding the second amino acid sequence. The polynucleotide of the present embodiment can be produced by a method of linking a polynucleotide having the first nucleotide sequence with a polynucleotide having the second nucleotide sequence, or the like. The method of linking the poly-nucleotides is not particularly limited, and any known method can be used. For example, an In-Fusion HD Cloning Kit (manufactured by Takara Bio, Inc.) or the like may be used together with an expression plasmid. In this case, the polynucleotide of the present embodiment can be obtained in a state of being incorporated into a plasmid. The expression plasmid is not particularly limited, and for example, pCDNA3.1 can be used.

In a cell of the present embodiment, the polynucleotide of the present embodiment or an expression plasmid having the polynucleotide incorporated therein is incorporated, and the cell can express the odorant receptor co-receptor described above. The cell of the present embodiment can be produced by incorporating the polynucleotide of the present embodiment or an expression plasmid into a cell. The cell can be selected as appropriate according to the type of the expression plasmid to be incorporated. Examples of the cell include colon bacteria such as *Escherichia coli* K12; *Bacillus* bacteria such as *Bacillus subtilis* MI114; yeasts such as *Saccharomyces cerevisiae* AH22; insect cells such as *Spodoptera frugiperda*-derived Sf cell line or *Trichoplusia ni*-derived HighFive cell line; and animal cells such as COS7 cells. Preferred examples of animal cells include mammal-derived culctured cells, and specific examples include COS7 cells, CHO cells, HEK293 cells, HEK293FT cells, Hela cells, PC12 cells, N1E-115 cells, and SH-SY5Y cells.

EXAMPLES

Hereinafter, the present invention will be specifically described based on Examples. However, the invention is not intended to be limited to the following Examples.

The insects described in the present Examples are as follows.

*Anopheles gambiae* (hereinafter, may be referred to as "*Anopheles*" or "Ag")

*Aedes aegypti* (hereinafter, may be referred to as "*Aedes*" or "Aa")

*Drosophila melanogaster* (hereinafter, may be referred to as "*Drosophila*" or "Dm")

*Apis mellifera* (hereinafter, may be referred to as "*Apis*" or "Am")

*Bombyx mori* (Hereinafter, may be referred to as "*Bombyx*" or "Bm")

Production of Expression Plasmid of Co-Receptor

Expression plasmid of *Drosophila mellifera* co-receptor (hereinafter, may be referred to as "DmORCO")

An adult *Drosophila melanogaster* RNA (manufactured by Takara Bio, Inc.) was used as a template, and a reverse transcription reaction was performed by adding Super Script III reverse transcriptase (manufactured by Invitrogen, Inc.) to the template and keeping the system warm for 50 minutes at 55° C. and then for 15 minutes at 75° C. Thus, cDNA was obtained. PCR was performed using 1 μL of the cDNA thus obtained as a template, and using 1 μL of 10 μM forward primer DmOrco-5' (5'-caccatgacaacctcgatgcagccgagcaagt; SEQ ID NO:3), 1 μL of 10 μM reverse primer DmOrco-3' (5'-ttacttgagctgcaccagcaccataaagt; SEQ ID NO:4), and 1 μL of KOD Plus neo DNA polymerase (manufactured by Toyobo Co., Ltd.). The PCR reaction was carried out under the following conditions: (1) 94° C., for 2 minutes, (2) 98° C., for 10 seconds, and (3) 68° C., for 1.5 minutes, and the processes of (2) and (3) were repeatedly carried out for 35 cycles. The PCR product thus obtained was subjected to agarose gel electrophoresis, and then about 1.5-kb DNA detected on the gel was collected. The DNA thus collected was incorporated into pENTRID-TOPO vector (manufactured by Invitrogen, Inc.), and a plasmid named pENTR-DmOrco was obtained. 4 µL of pENTR-DmOrco, 1 µL of pcDNA6.2V5-DEST, and 2 µL, of LR Clonase II (manufactured by Invitrogen, Inc.) were mixed, and the mixture was maintained for one hour at room temperature. The mixture thus obtained was incorporated into *Escherichia coli*, and the bacterial cells were cultured. Thereby, an expression plasmid named pcDNA6.2-DmOrco was obtained. The nucleotide sequence of the expression plasmid pcDNA.6.2-DmOrco was analyzed using a DNA sequencer, and it was found that this plasmid contained the nucleotide sequence set forth in SEQ ID NO:5. The nucleotide sequence set forth in SEQ NO:5 encodes the amino acid sequence set forth in SEQ ID NO:6.

Expression plasmid of *Aedes aegypti* co-receptor (hereinafter, may be referred to as "AaORCO")

The head part of *Aedes aegypti* was frozen with liquid nitrogen, and then TRIzol (manufactured by Invitrogen, Inc.) was added thereto. The frozen head part was crushed using a mortar and a pestle in the presence of liquid nitrogen. From the crushed product thus obtained, RNA was extracted according to the manual attached to the TRIzol reagent. The RNA thus extracted was purified using an RNA purification kit (RNeasy Mini Kit; manufactured by QIAGEN N.V.) according to the manual attached to the kit. A reverse transcription reaction was carried out using the Total RNA thus obtained as a template, adding Super Script III reverse transcriptase (manufactured by Invitrogen, Inc.) to the template, and keeping the mixture warm for 50 minutes at 55° C. and then for 15 minutes at 75° C. Thus, cDNA was obtained. PCR was performed using 1 µL of the cDNA thus obtained as a template, and using 1 µL of 10 µM forward primer AaOrco-5' (5'-tggaattctgcagatcaccatgaacgtc-caaccgacaaagtacc; SEQ ID NO:7), 1 µL of 10 µM reverse primer AaOrco-3' (5'-gccactgtgctggatttatttcaactgcaccaacacc; SEQ ID NO:8), and 1 µL of KOD Plus neo DNA polymerase (manufactured by Toyobo Co., Ltd.). The PCR reaction was carried out under the following conditions: (1) 94° C., for 2 minutes, (2) 98° C., for 10 seconds, (3) 6:3° C., for 30 seconds, and (4) 68° C., for 1.5 minutes, and the processes of (2) to (4) were repeatedly carried out for 35 cycles. The PCR product thus obtained was linked to pcDNA3.1 (manufactured by Invitrogen, Inc.) that had been digested with EcoRV using In-Fusion HD Cloning Kit (manufactured by Takara Bio, Inc.), subsequently the product was incorporated into *Escherichia coli*, and the bacterial cells were cultured. Thus, an expression plasmid named pcDNA3.1-AaOrco was obtained. The nucleotide sequence of the expression plasmid pcDNA3.1-AaOrco was analyzed using a DNA sequencer, and it was found that this plasmid contained the nucleotide sequence set forth in SEQ IIS NO:9. The nucleotide sequence set forth in SEQ ID NO:9 encodes the amino acid sequence set forth in SEQ ID NO:10.

Expression plasmid of *Apis* co-receptor (hereinafter, may be referred to as "AmORCO")

Double-stranded DNA having the nucleotide sequence set forth in SEQ ID NO:11 in any one of the DNA strands was synthesized. PCR was performed using 100 ng of the DNA thus obtained as a template, and using 1 µL of 10 µM forward primer AmOrco-5' (5'-tggaattctgcagatcaccatgaagtt-caagcaacaagggctaa; SEQ ID NO:12), 1 µL of 10 µM reverse primer AmOrco-3' (5'-gccactgtgctggattcacttcagttgcac-caacaccatgaa; SEQ ID NO:13), and 1 µL of KOD Plus neo DNA polymerase (manufactured by Toyobo Co., Ltd.). The PCR reaction was carried out under the following conditions: (1) 94° C., for 2 minutes, (2) 98° C., for 10 seconds, (3) 63"c, for 30 seconds, and (4) 68° C., for 1.5 minutes, and the processes of (2) to (4) were repeatedly carried out for 35 cycles. The PCR product thus obtained was linked to pcDNA3.1 (manufactured by Invitrogen, Inc.) that had been digested with EcoRV, using In-Fusion HD Cloning Kit (manufactured by Takara Bio, Inc.), subsequently the product was incorporated into *Escherichia coli*, and the bacterial cells were cultured. Thus, an expression plasmid named pcDNA3.1-AmOrco was obtained. The nucleotide sequence of the expression plasmid pcDNA3.1-AmOrco was analyzed using a DNA sequencer, and it was found that this plasmid contained the nucleotide sequence set forth in SEQ ID NO:11. The nucleotide sequence set forth in SEQ ID NO:11 encodes the amino acid sequence set forth in SEQ ID NO:14.

Expression plasmid of *Anopheles* co-receptor (hereinafter, may be referred to as "AgORCO")

The head part of *Anopheles gambiae* Kisum strain or G3 strain was frozen with liquid nitrogen, and then TRIzol (manufactured by Invitrogen, Inc.) was added thereto. The frozen head part was crushed using a mortar and a pestle in the presence of liquid nitrogen. From the crushed product thus obtained, RNA was extracted according to the manual attached to the TRIzol reagent. The RNA thus extracted was purified using an RNA purification kit (RNeasy Mini Kit; manufactured by QIAGEN N.V.) according to the manual attached to the kit. A reverse transcription reaction was carried out using the Total RNA thus obtained as a template, adding Super Script III reverse transcriptase (manufactured by Invitrogen, Inc.) to the template, and keeping the mixture warm for 50 minutes at 55° C. and then for 15 minutes at 75° C. Thus, cDNA was obtained. PCR was performed using 1 µL of the cDNA thus obtained as a template, and using 1 µL of 10 µM forward primer AgOrco-5' (5'-cac-catgcaagtccagccgaccaagtacgtcggcct; SEQ ID NO:15), 1 µL of 10 µM reverse primer AgOrco-3' (5'-ttacttcagctgcaccagcaccatgaagt; SEQ ID NO:16), and 1 µL of KOD Plus neo DNA polymerase (manufactured by Toyobo Co., Ltd.). The PCR reaction was carried out under the following conditions: (1) 94° C., for 5 minutes, (2) 98° C., for 10 seconds, (3) 60° C., for 30 seconds, and (4) 68° C., for 1.5 minutes, and the processes of (2) to (4) were repeatedly carried out for 35 cycles. The PCR product thus obtained was subjected to agarose gel electrophoresis, and then about 1.4-kb DNA detected on the gel was collected. The DNA thus collected was incorporated into pENTR/D-TOPO vector (manufactured by Invitrogen, Inc.), and a plasmid named pENTR-AgOrco was obtained. 4 µL of pENTR-AgOrco, 1 µL of pcDNA6.2V5-DEST, and 2 µL of LR Clonase II (manufactured by Invitrogen, Inc.) were mixed, and the mixture was maintained for one hour at room temperature. The mixture thus obtained was incorporated into *Escherichia coli*, and the bacterial cells were cultured. Thereby, an expression plasmid named pcDNA6.2-AgOrco was obtained. The nucleotide sequence of the expression plasmid pcDNA6.2-AgOrco was analyzed using a DNA sequencer, and it was found that this plasmid contained the nucleotide sequence set forth in SEQ ID NO:17. The nucleotide sequence set forth in SEQ ID NO:17 encodes the amino acid sequence set forth in SEQ ID NO:18.

Expression plasmid of chimeric co-receptor of *Drosophila* co-receptor and *Aedes* co-receptor PCR was performed using 100 ng of the expression plasmid of DmORCO described above as a template, and using 1 μL of a 10-μM forward primer, 1 μL of a 10-μM reverse primer, and 1 μL of KOD Plus neo DNA polymerase (manufactured by Toyobo Co., Ltd.). The PCR reaction was carried out under the following conditions: (1) 94° C., for 2 minutes, 98° C., for 10 seconds, (3) 63° C., for 30 seconds, and (4) 68'C, for 1.5 minutes, and the processes of (2) to (4) were repeated for 35 cycles. The combinations of the forward primer and the reverse primer, and the PCR product thus obtained are presented in Table 1.

Furthermore, PCR performed using 1 μL (100 ng) of the above-mentioned expression plasmid of AaORCO as a template, and using 1 μL of a 10-μM forward primer, 1 μL of a 10-μM reverse primer, and 1 μL of KOD Plus neo DNA polymerase (manufactured by Toyobo Co., Ltd.). The PCR reaction was carried out under the following conditions: (1) 94° C., for 2 minutes, (2) 98° C., for 10 seconds, (3) 63° C., for 30 seconds, and (4) 68° C., for 1.5 minutes, and the processes of (2) to (4) were repeated for 35 cycles. The combinations of the forward primer and the reverse primer, and the PCR product thus obtained are presented in Table 2.

One of the PCR products described in Table 1 and one of the PCR products described in Table 2 were linked in the combinations indicated in Table 3, to pcDNA3.1 (manufactured by Invitrogen, Inc.) that had been digested with EcoRV, using In-Fusion HD Cloning Kit (manufactured by Takara Bio, Inc.). The DNA thus linked was incorporated into *Escherichia coli*, and the bacterial cells were cultured. Thereby, expression plasmids of various chimeric co-receptors derived from a *Drosophila* co-receptor and an *Aedes* co-receptor were obtained. The nucleotide sequences of the chimeric receptor expression plasmids thus obtained were analyzed using a DNA sequencer, and it was found that each of the various plasmids contained any one of nucleotide sequences set forth in SEQ ID NO:59 to SEQ ID NO:68. The nucleotide sequences set forth in SEQ ID NO:59 to SEQ ID NO:68 encode amino acid sequences set forth in SEQ ID NO:69 to SEQ NO:78, respectively. The combinations of the PCR products used for the production of the above-mentioned chimeric receptor expression plasmids, the sequence numbers of the nucleotide sequences of chimeric co-receptor encoding domains, and the sequence numbers of the amino acid sequences of the chimeric co-receptors are presented in Table 3.

The configurations of the amino acid sequences of the chimeric co-receptors encoded by the expression plasmids thus obtained are described below.

In DM(NT-EC)AaORCO, the amino acid sequence including from the N-terminal domain (NT) to the first extracellular loop (EC1) is derived from a *Drosophila* co-receptor, and the amino acid sequence including from the second transmembrane domain to the C-terminal domain is derived from an *Aedes* co-receptor.

In Dm(NT-TM3)AaORCO, the amino acid sequence including from the N-terminal domain (NT) to the third transmembrane domain (TM3) is derived from a *Drosophila* co-receptor, and the amino acid sequence including from the second extracellular loop to the C-terminal domain is derived from an *Aedes* co-receptor.

In Dm(NT-TM4)AaORCO, the amino acid sequence including from the N-terminal domain (NT) to the fourth transmembrane domain (TM4) (amino acid sequence including from the N-terminal amino acid residue to amino acid residue 234) is derived from a *Drosophila* co-receptor (Dm(NT-TM4), SEQ ID NO:1), and the amino acid sequence including from the second intracellular loop to the C-terminal domain is derived from an *Aedes* co-receptor (Aa(IC2-CT), SEQ ID NO:137).

In Dm(NT-TM5)AaORCO, the amino acid sequence including from the N-terminal domain (NT) to the fifth transmembrane domain (TM5) is derived from a *Drosophila* co-receptor, and the amino acid sequence including from the third extracellular loop to the C-terminal domain is derived from an *Aedes* co-receptor.

In Dm(NT-TM6)AaORCO, the amino acid sequence including from the N-terminal domain (NT) to the sixth transmembrane domain (TM6) is derived from a *Drosophila* co-receptor, and the amino acid sequence including from the third intracellular loop to the C-terminal domain is derived from an *Aedes* co-receptor.

In Dm(NT-792)AaORCO, the amino acid sequence including from the N-terminal amino acid residue to amino acid residue 264 is derived from a *Drosophila* co-receptor, and the amino acid sequence including from amino acid residue 265 to the C-terminal amino acid residue is derived from an *Aedes* co-receptor.

In Dm(NT-879)AaORCO, the amino acid sequence including from the N-terminal amino acid residue to amino acid residue 293 is derived from a *Drosophila* co-receptor, and the amino acid sequence including from amino acid residue 294 to the C-terminal amino acid residue is derived from an *Aedes* co-receptor.

In Dm(NT-969)AaORCO, the amino acid sequence from the N-terminal amino acid residue to amino acid residue 323 is derived from a *Drosophila* co-receptor, and the amino acid sequence including from amino acid residue 324 to the C-terminal amino acid residue is derived from an *Aedes* co-receptor.

In Dm(NT-1080)AaORCO, the amino acid sequence including from the N-terminal amino acid residue to amino acid residue 360 is derived from a *Drosophila* co-receptor, and the amino acid sequence including from amino acid residue 361 to the C-terminal amino acid residue is an *Aedes* co-receptor.

In Dm(NT-636)AaORCO, the amino acid sequence including from the N-terminal amino acid residue to amino acid residue 212 is derived from a *Drosophila* co-receptor, and the amino acid sequence including from amino acid residue 213 to the C-terminal amino acid residue is an *Aedes* co-receptor.

TABLE 1

| PCR product | Primer | Sequence number of primer | Nucleotide sequence (5'-3') |
|---|---|---|---|
| Dm (NT-EC1) | Forward | 19 | tggaattctgcagatcaccatgacaacctcgatgcagccgagcaa |
|  | Reverse | 20 | cgtgttgcccgacagctcgttgacct |
| Dm (NT-TM3) | Forward | 21 | tggaattctgcagatcaccatgacaacctcgatgcagccgagcaa |
|  | Reverse | 22 | aaagaaggtgatcgtggtccaggcggt |
| Dm (NT-TM4) | Forward | 23 | tggaattctgcagatcaccatgacaacctcgatgcagccgagcaa |
|  | Reverse | 24 | caagtgctgcagctgctcgcaggcgaatat |
| Dm (NT-TM5) | Forward | 25 | tggaattctgcagatcaccatgacaacctcgatgcagccgagcaa |
|  | Reverse | 26 | ggcctggtatgccagcagggtcagcttgat |
| Dm (NT-TM6) | Forward | 27 | tggaattctgcagatcaccatgacaacctcgatgcagccgagcaa |
|  | Reverse | 28 | attgccaaagatgcaaaagtggaaca |
| DM (792) | Forward | 29 | tggaattctgcagatcaccatgacaacctcgatgcagccgagcaa |
|  | Reverse | 30 | ggccgacagggacctgaagagggccgccgagtt |
| Dm (879) | Forward | 31 | tggaattctgcagatcaccatgacaacctcgatgcagccgagcaa |
|  | Reverse | 32 | atccgctttcgagctgtagatgccc |
| Dm (969) | Forward | 33 | tggaattctgcagatcaccatgacaacctcgatgcagccgagcaa |
|  | Reverse | 34 | gggattagcgccgttcaccaacccgtt |
| Dm (1080) | Forward | 35 | tggaattctgcagatcaccatgacaacctcgatgcagccgagcaa |
|  | Reverse | 36 | tccgtaagtatcgccgatggcagcca |
| Dm (636) | Forward | 37 | tggaattctgcagatcaccatgacaacctcgatgcagccgagcaa |
|  | Reverse | 38 | gtgatcatcgagaagagcacgtagt |

(NT: N-terminal domain, EC: extracellular loop, TM: transmembrane domain)

TABLE 2

| PCR product | Primer | Sequence number of primer | Nucleotide sequence (5'-3') |
|---|---|---|---|
| Aa (TM2-CT) | Forward | 39 | ctgtcgggcaacacgataacgacgctgtttttcacccatt |
|  | Reverse | 40 | gccactgtgctggatttatttcaactgcaccaacaccatgaaa |
| Aa (EC2-CT) | Forward | 41 | acgatcaccttctttggcgatagcgtcaaaaacgtattcg |
|  | Reverse | 42 | gccactgtgctggatttatttcaactgcaccaaca |
| Aa (IC2-CT) | Forward | 43 | cagctgcagcacttgaagggtataatgcgccccctgatgaa |
|  | Reverse | 44 | gccactgtgctggatttatttcaactgcaccaaca |
| Aa (EC3-CT) | Forward | 45 | ctggcataccaggccaccaaaatcgatgcactcaacgtt |
|  | Reverse | 46 | gccactgtgctggatttatttcaactgcaccaaca |
| Aa (IC3-CT) | Forward | 47 | tgcatctttggcaatcgattaattgaagagagttcatcag |
|  | Reverse | 48 | gccactgtgctggatttatttcaactgcaccaaca |
| Aa (792) | Forward | 49 | aggtccctgtcggccggatccaaatcggagctgattttgaat |
|  | Reverse | 50 | gccactgtgctggatttatttcaactgcaccaacaccatgaa |
| Aa (879) | Forward | 51 | agctcgaaagcggattggggtgcccagttcagggcgccat |
|  | Reverse | 52 | gccactgtgctggatttatttcaactgcaccaacaccatgaa |
| Aa (969) | Forward | 53 | aacggcgctaatcccaatggactaaccaagaagcaggaact |
|  | Reverse | 54 | gccactgtgctggatttatttcaactgcaccaacaccatgaa |
| Aa (1080) | Forward | 55 | ggcgatacttacggagccgccctgttgcttcacatgttga |
|  | Reverse | 56 | gccactgtgctggatttatttcaactgcaccaacaccatgaa |
| Aa (636) | Forward | 57 | ttctcgatgatccacgccaacctcgcgatgtgatgttttt |
|  | Reverse | 58 | gccactgtgctggatttatttcaactgcaccaacaccatgaa |

(EC: extracellular loop, IC: intracellular loop, TM: transmembrane domain, CT: C-terminal domain)

TABLE 3

| Chimeric co-receptor | PCR product | Sequence number of nucleotide sequence | Sequence number of amino acid sequence |
| --- | --- | --- | --- |
| Dm (NT-EC1)AaORCO | Dm (NT-EC1), Aa (TM2-CT) | 59 | 69 |
| Dm (NT-TM3)AaORCO | Dm (NT-TM3), Aa (EC2-CT) | 60 | 70 |
| Dm (NT-TM4)AaORCO | Dm (NT-TM4), Aa (IC2-CT) | 61 | 71 |
| Dm (NT-TM5)AaORCO | Dm (NT-TM5), Aa, (EC3-CT) | 62 | 72 |
| Dm (NT-TM6)AaORCO | Dm (NT-TM6), Aa (IC3-CT) | 63 | 73 |
| Dm (NT-792)AaORCO | Dm (792), Aa (792) | 64 | 74 |
| Dm (NT-879)AaORCO | Dm (879), Aa (879) | 65 | 75 |
| Dm (NT-969)AaORCO | Dm (969), Aa (969) | 66 | 76 |
| Dm (NT-1080)AaORCO | Dm (1080), Aa (1080) | 67 | 77 |
| Dm (NT-636)AaORCO | Dm (636), Aa (636) | 68 | 78 |

(NT: N-terminal domain, EC: extracellular loop, TM: transmembrane domain)

Expression plasmid of chimeric co-receptor in which transmembrane domain is derived from *Drosophila* co-receptor and other domains are derived from *Aedes* co-receptor (hereinafter, may be referred to as "Aa(TM1-4Dm)AaORCO")

Double-stranded DNA having the nucleotide sequence set forth in SEQ ID NO:79 in any one of the DNA strands was synthesized. PCR was performed using 100 ng of the DNA thus obtained as a template, and using 1 µL of 10 µM forward primer AaOrco-5' (5'-tggaattctgcagatcaccatgaacgtc-caaccgacaaagtacc; SEQ NO:80), 1 µL of 10 µM reverse primer DmAaOrco(IC2-CT)-3' (5'-gccactgtgctggatttattt-caactgcaccaaca; SEQ ID NO:81), and 1 µL of KOD Plus neo DNA polymerase (manufactured by Toyobo Co., Ltd.). The PCR reaction was carried out under the following conditions: (1) 94° C., for 2 minutes, (2) 98° C., for 10 seconds, (3) 63° C., for 30 seconds, and (4) 68° C., for 1.5 minutes, and the processes of (2) to (4) were repeatedly carried out for 35 cycles. The PCR product thus obtained was linked to pcDNA3.1 (manufactured by Invitrogen, Inc.) that had been digested with EcoRV, using In-Fusion HD Cloning Kit (manufactured by Takara Bio, Inc.), subsequently the product was incorporated into *Escherichia coli*, and the bacterial cells were cultured. Thus, an expression plasmid named pcDNA3.1-Aa(TM1-4Dm)AaOrco was obtained. The nucleotide sequence of the expression plasmid pcDNA3.1-Aa(TM1-4Dm)AaOrco was analyzed using a DNA sequencer, and it was found that this plasmid contained the nucleotide sequence set forth in SEQ ID NO:79. The nucleotide sequence set forth in SEQ ID NO:79 encodes the amino acid sequence set forth in SEQ ID NO:82. In the chimeric co-receptor encoded by the expression plasmid pcDNA3.1-Aa(TM1-4Dm)AaOrco, the amino acid sequences of the first transmembrane domain, the second transmembrane domain, the third transmembrane domain, and the fourth transmembrane domain are derived from a *Drosophila* co-receptor, and the amino acid sequences of the other domains are derived from an *Aedes* co-receptor.

Expression plasmid of chimeric co-receptor in which amino-terminal domain, first extracellular loop, first intracellular loop, and second extracellular loop are derived from a *Drosophila* co-receptor, and other domains are derived from *Aedes* co-receptor (hereinafter, may be referred to as "Dm(TM1-4Aa)AaORCO")

Double-stranded DNA having a nucleotide sequence set forth in SEQ ID NO:83 in any one of the DNA strands was synthesized. PCR was performed using 100 ng of the DNA thus obtained as a template, and using 1 µL of 10 µM forward primer DmOrco(NT-TM4)-5' (5'-tggaattctgcagat-caccatgacaacctcgatgcagccgagcaa; SEQ ID NO:84), 1 µL of 10 µM reverse primer DmAaOrco(IC2-CT)-3' (5'-gc-cactgtgctggatttatttcaactgcaccaaca; SEQ ID NO:85), and 1 µL of KOD Plus neo DNA polymerase (manufactured by Toyobo Co., Ltd.). The PCR reaction was carried out under the following conditions: (1) 94° C., for 2 minutes, (2) 98° C., for 10 seconds, (3) 63° C., for 30 seconds, and (4) 68° C., for 1.5 minutes, and the processes of (2) to (4) were repeatedly carried out for 35 cycles. The PCR product thus obtained was linked to pcDNA3.1 (manufactured by Invitrogen, Inc.) that had been digested with EcoRV, using In-Fusion HD Cloning Kit (manufactured by Takara Bio, Inc.), subsequently the product was incorporated into *Escherichia coli*, and the bacterial cells were cultured. Thus, an expression plasmid named pcDNA3.1-Dm(TM1-4Aa)AaOrco was obtained. The nucleotide sequence of the expression plasmid pcDNA3.1-Aa(TM1-4Dm)AaOrco was analyzed using a DNA sequencer, and it was found that this plasmid contained a nucleotide sequence set forth in SEQ ID NO:83. The nucleotide sequence set forth in SEQ NO:83 encodes the amino acid sequence set forth ire SEQ ID NO:86. In the chimeric co-receptor encoded by the expression plasmid pcDNA3.1-Aa(TM1-4Dm)AaOrco, the amino acid sequences of the amino-terminal domain, the first extracellular loop, the first intracellular loop, and the second extracellular loop are derived from a *Drosophila* co-receptor; the amino acid sequences of the first transmembrane domain, the second transmembrane domain, the third transmembrane domain, and the fourth transmembrane domain are derived from an *Aedes* co-receptor; and the amino acid sequence including from the second intracellular loop to the C-terminal domain is derived from an *Aedes* co-receptor.

Expression plasmid of chimeric co-receptor of *Drosophila* co-receptor and *Apis* co-receptor Dm(NT-TM3), Dm(NT-TM4), Dm(NT-TM5), and Dm(NT-Tm6) as the PCR products shown in Table 1 were produced.

PCR was performed using 1 µL (100 ng) of the above-mentioned expression plasmid of AmORCO as a template, and using 1 µL of a 10-µM forward primer, 1 µL of a 10-µM reverse primer, and 1 µL of KOD Plus neo DNA polymerase (manufactured by Toyobo Co., Ltd.). The PCR reaction was carried out under the following conditions; (1) 94° C., for 2 minutes, (2) 98° C., for 10 seconds, (3) 63° C., for 30 seconds, and (4) 68° C., for 1.5 minutes, and the processes of (2) to (4) were repeatedly carried out for 35 cycles. The combinations of the forward primer and the reverse primer, and the PCR products thus obtained, are presented in Table 4.

One of the PCR products Dm(NT-TM3), Dm(NT-TM4), Dm(NT-TM5), and Dm(NT-Tm6), and one of the PCR products described in Table 4 were linked in the combinations indicated in Table 5 to pcDNA3.1 (manufactured by Invitrogen, Inc.) that had been digested with EcoRV, using In-Fusion HD Cloning Kit (manufactured by Takara Bio, Inc.). The DNA thus linked was incorporated into *Escherichia coli*, and the bacterial cells were cultured. Thus, expression plasmids of various chimeric co-receptors derived from a *Drosophila* co-receptor and an *Apis* co-receptor were obtained. The nucleotide sequences of the chimeric receptor expression plasmids thus obtained were analyzed using a DNA sequencer, and it was found that each of the various plasmids contained any one of nucleotide sequences set forth in SEQ ID NO:95 to SEQ ID NO:98. The nucleotide sequences set forth in SEQ ID NO:95 to SEQ ID NO:98 encode amino acid sequences set forth in SEQ XD NO:99 to SEQ ID NO:102, respectively. The sequence numbers of the nucleotide sequence of the combination of PCR products used for the production of the chimeric receptor expression plasmids, the sequence number of the nucleotide sequences of the chimeric co-receptor encoding domain, and the sequence numbers of the amino acid sequences of the chimeric co-receptor are shown in Table 5.

The configuration of the amino acid sequences of the chimeric co-receptors encoded by the expression plasmids thus obtained is shown below.

In Dm(NT-TM3)AmORCO, the amino acid sequence including from the N-terminal domain (NT) to the third transmembrane domain (TM3) is derived from a *Drosophila* co-receptor, and the amino acid sequence including from the second extracellular loop to the C-terminal domain is derived from an *Apis* co-receptor (Am(IC2-CT), SEQ ID NO:2).

In Dm(NT-TM4)AmORCO, the amino acid sequence including from the N-terminal domain (NT) to the fourth transmembrane domain (TM4) is derived from a *Drosophila* co-receptor (Dm(NT-TM4) SEQ ID NO:1), and the amino acid sequence including from the second intracellular loop to the C-terminal domain is derived from an *Apis* co-receptor.

In Dm(NT-TM5)AmORCO, the amino acid sequence including from the N-terminal domain (NT) to the fifth transmembrane domain (TM5) is derived from a *Drosophila* co-receptor, and the amino acid sequence including from the third extracellular loop to the C-terminal domain is derived from an *Apis* co-receptor.

In Dm(NT-TM6)AmORCO, the amino acid sequence including from the N-terminal domain (NT) to the sixth transmembrane domain (TM6) is derived from a *Drosophila* co-receptor, and the amino acid sequence including from the third intracellular loop to the C-terminal domain is derived from an *Apis* co-receptor.

TABLE 5

| Chimeric co-receptor | PCR product | Sequence number of nucleotide sequence | Sequence number of amino acid sequence |
|---|---|---|---|
| Dm (NT-TM3)AmORCO | Dm (NT-TM3), Am (EC2-CT) | 95 | 99 |
| Dm (NT-TM4)AmORCO | Dm (NT-TM4), Am (IC2-CT) | 96 | 100 |
| Dm (NT-TM5)AmORCO | Dm (NT-TM5), Am (EC3-CT) | 97 | 101 |
| Dm (NT-TM6)AmORCO | Dm (NT-TM6), Am (IC3-CT) | 98 | 102 |

(NT: N-terminal domain, TM: transmembrane domain)

Expression plasmid of chimeric co-receptor of *Aedes* co-receptor and *Apis* co-receptor (hereinafter, may be referred to as "Aa(NT-TM4)AmORCO")

PCR was performed using 100 ng of the above-mentioned expression plasmid of AaORCO as a template, and using 1 μL of 10 μM forward primer AaOrco(NT-TM4)-5' (5'-tggaattctgcagatcaccatgaacgtccaaccgacaaagtacc; SEQ ID NO:103), 1 μL of 10 μM reverse primer AaOrco (NT-TM4)-3' (5'-caaatgttgcagctgttcgcaagtga; SEQ ID NO:104), and 1 μL of KOD Plus neo DNA polymerase (manufactured by Toyobo Co., Ltd.). The PCR reaction was carried out under the following conditions: (1) 94° C., for 2 minutes, (2) 98° C., for 10 seconds, (3) 63° C., for 30 seconds, and (4) 68° C., for 1.5 minutes, and the processes of (2) to (4) were repeatedly carried out for 35 cycles. PCR was performed using 100 ng of the above-mentioned expression plasmid of AmORCO as a template, and using 1 μL of 10 μM forward primer AaAmOrco(IC2-CT)-5' (5'-cagctgcaacatttgaagaatat-catgaagcctttgatggaa; SEQ ID NO:105), 1 μL of 10 μM reverse primer AaAmOrco (IC2-CT)-3' (5'-gccactgtgctggat-tcacttcagttgcaccaacaccatgaa; SEQ ID NO:106), and 1 μL of KOD Plus neo DNA polymerase (manufactured by Toyobo Co., Ltd.). The PCR reaction was carried out under the following conditions: (1) 94° C., for 2 minutes, (2) 98° C., for 10 seconds, (3) 63° C., for 30 seconds, and (4) 68° C., for 1.5 minutes, and the processes of (2) to (4) were repeatedly carried out for 35 cycles. The two PCR products thus obtained were linked to pcDNA3.1 (manufactured by Invitrogen, Inc.) that had been digested with EcoRV, using In-Fusion HD Cloning Kit (manufactured by Takara Bio, Inc.). The DNA thus linked was incorporated into *Escherichia coli*, and the bacterial cells were cultured. Thus, an expression plasmid of a chimeric co-receptor of an *Aedes*

TABLE 4

| PCR product | Primer | Sequence number of primer | Nucleotide sequence (5'-3') |
|---|---|---|---|
| Am (EC2-CT) | Forward | 87 | acgatcaccttctttggtgactctgtgaaaaaggtcatcg |
| Am (EC2-CT) | Reverse | 88 | gccactgtgctggattcacttcagttgcaccaacaccatgaa |
| Am (IC2-CT) | Forward | 89 | cagctgcagcacttgaagaatatcatgaagcctttgatgg |
| Am (IC2-CT) | Reverse | 90 | gccactgtgctggattcacttcagttgcaccaacaccatgaa |
| Am (EC3-CT) | Forward | 91 | ctggcataccaggccacaaagatacatgcagtagatacat |
| Am (EC3-CT) | Reverse | 92 | gccactgtgctggattcacttcagttgcaccaacaccatgaa |
| Am (IC3-CT) | Forward | 93 | tgcatctttggcaatcgtctcattgaagagagctcatcag |
| Am (IC3-CT) | Reverse | 94 | gccactgtgctggattcacttcagttgcaccaacaccatgaa |

(EC: extracellular loop, IC: intracellular loop, CT: C-terminal domain)

co-receptor and an *Apis* co-receptor, which was named pcDNA3.1-AaAmOrco, was obtained. The nucleotide sequence of the expression plasmid pcDNA3.1-AaAmOrco thus obtained was analyzed using a DNA sequencer, and it was found that the expression plasmid contained the nucleotide sequence set forth in SEQ ID NO:107. The nucleotide sequence set forth in SEQ ID NO:107 encodes the amino acid sequence set forth in SEQ ID NO:108. In the chimeric co-receptor encoded by the expression plasmid pcDNA3.1-AaAmOrco, the amino acid sequence including from the N-terminal domain (NT) to the fourth transmembrane domain (TM4) is derived from an *Aedes* co-receptor (Aa (NT-TM4), SEQ ID NO:135), and the amino acid sequence including from the second intracellular loop to the C-terminal domain is derived from an *Apis* co-receptor (Am(IC2-CT), SEQ ID NO:2).

Expression plasmid of chimeric co-receptor of *Anopheles* co-receptor and *Apis* co-receptor (hereinafter, may be referred to as "Ag(NT-TM4) Am ORCO")

PCR was performed using 100 ng of the above-mentioned expression plasmid of an *Anopheles* co-receptor as a template, and using 1 µL of 10 µM forward primer AgOrco(NT-TM4)-5' (5'-tggaattctgcagatcaccatgcaagtccagccgac-caagtacgt; SEQ ID NO:109), 1 µL of 10 µM reverse primer AgOrco(NT-TM4)-3' (5'-caagtgttgcagctgctcgcaggcta; SEQ ID NO:110), and 1 µL of KOD Plus neo DNA polymerase (manufactured by Toyobo Co., Ltd.). The PCR reaction was carried out under the following conditions: (1) 94° C., for 2 minutes, (2) 98° C., for 10 seconds, (3) 63° C., for 30 seconds, and (4) 68'C, for 1.5 minutes, and the processes of (2) to (4) were repeatedly carried out for 35 cycles. PCR was performed using 100 ng of the above-mentioned expression plasmid of an *Apis* co-receptor as a template, and using 1 µL of 10 µM forward primer AgAmOrco(IC2-CT)-5' (5'-cagctgcaacacttgaagaatatcatgaagcctttgatgg; SEQ ID NO:111), 1 µL, of 10 µM reverse primer AmOrco-3' (5'-gccactgtgctggattcacttcagttgcaccaacaccatgaa; SEQ ID NO:112), and 1 µL of KOD Plus neo DNA polymerase (manufactured by Toyobo Co., Ltd.). The PCR reaction was carried out under the following conditions: (1) 94° C., for 2 minutes, (2) 98° C., for 10 seconds, (3) 63° C., for 30 seconds, and (4) 68° C., for 1.5 minutes, and the processes of (2) to (4) were repeatedly carried out for 35 cycles. The two PCR products thus obtained were linked to pcDNA3.1 (manufactured by Invitrogen, Inc.) that had been digested with EcoRV, using In-Fusion HD Cloning Kit (manufactured by Takara Bio, Inc.). The DNA thus linked was incorporated into *Escherichia coli*, and the bacterial cells were cultured. Thus, an expression plasmid of a chimeric co-receptor of an *Anopheles* co-receptor and an *Apis* co-receptor, which was named pcDNA3.1-AgAmOrco, was obtained. The nucleotide sequence of the expression plasmid pcDNA3.1-AgAmOrco thus obtained was analyzed using a DNA sequencer, and it was found that the expression plasmid contained the nucleotide sequence set forth in SEQ ID NO:113. The nucleotide sequence set forth in SEQ ID NO:113 encodes the amino acid sequence set forth in SEQ ID NO:114. In the chimeric co-receptor encoded by the expression plasmid pcDNA3.1-AgAmOrco, the amino acid sequence including from the N-terminal domain (NT) to the fourth transmembrane domain (TM4) is derived from an *Anopheles* co-receptor (Ag(NT-TM4), SEQ ID NO:136), and the amino acid sequence including from the second intracellular loop to the C-terminal domain is derived from an *Apis* co-receptor (Am(IC2-CT), SEQ ID NO:2).

Production of Odorant Receptor Expression Plasmid

Expression plasmid of *Aedes* odorant receptor OR8 (hereinafter, may be referred to as "AaOR8")

1 µL of a cDNA derived from the *Aedes* head part produced by the method described above was used as a template, and PCR was performed using 1 µL of 10 µM forward primer AaOR8-5' (5'-tggaattctgcagatcaccatgg-gagggtaagttctc; SEQ ID NO:115), 1 µL of 10 µM reverse primer AaOR8-3' (5'-gccactgtgctggattcacttctgacttggttc; SEQ ID NO:116), and 1 µL of KOD Plus neo DNA polymerase (manufactured by Toyobo Co., Ltd.). The PCR reaction was carried out under the following conditions: (1) 94° C., for 2 minutes, (2) 98° C., for 10 seconds, and (3), 68° C., for 1 minute, and the processes of (2) to (4) were repeatedly carried out for 30 cycles. The PCR product thus obtained was linked to pcDNA3.1 (manufactured by Invitrogen, Inc.) that had been digested with EcoRV, using In-Fusion HD Cloning Kit (manufactured by Takara Bio, Inc.). The DNA thus linked was incorporated into *Escherichia coli*, and the bacterial cells were cultured. Thus, an expression plasmid named pcDNA3.1-AaOR8 was obtained. The nucleotide sequence of the expression plasmid pcDNA3.1-AaOR8 was analyzed using a DNA sequencer, and it was found that the expression plasmid contained the nucleotide sequence set forth in SEQ ID NO:117. The nucleotide, sequence set forth in SEQ NO:117 encodes the amino acid sequence set forth in SEQ ID NO:118.

Expression plasmid of *Drosophila* odorant receptor OR47a, (hereinafter, may be referred to as "DmOR47a")

1 µL of a cDNA derived from *Drosophila* image produced by the method described above was used as a template, and PCR was performed using 1 µL of 10 µM forward primer DmOR47a-5' (5'-caccatggacagtttctgcaagtacagaa; SEQ ID NO:119), 1 µL of 10 µM reverse primer DmOR47a-3' (5'-ttaggagaatgatctcagcattgtgatgta; SEQ ID NO:120), and 1 µL of KOD Plus neo DNA polymerase (manufactured by Toyobo Co., Ltd.). The PCR reaction was carried out under the following conditions: (1) 94° C., for 2 minutes, (2) 98° C., for 10 seconds, and (3) 68° C., for 1.5 minutes, and the processes of (2) and (3) were repeatedly carried out for 35 cycles. The PCR product thus obtained was subjected to agarose gel electrophoresis, and then about 1.2-kb DNA detected on the gel was collected. The DNA thus collected was incorporated into pENTR/D-TOPO vector (manufactured by Invitrogen, Inc.), and a plasmid named pENTR-DmOR47a was obtained. 4 µL of pENTR-DmOR47a, 1 µL of pcDNA6.2V5-DEST, and 2 µL of LR Clonase II (manufactured by Invitrogen, Inc.) were mixed, and the mixture was maintained for one hour at room temperature. The mixture thus obtained was incorporated into *Escherichia coli*, and the bacterial cells were cultured. Thereby, an expression plasmid named pcDNA6.1-DmOR47a was obtained. The nucleotide sequence of the expression plasmid pcDNA6.2-DmOR47a was analyzed using a DNA sequencer, and it was found that the expression plasmid contained the nucleotide sequence set forth in SEQ ID NO:121. The nucleotide sequence set forth in SEQ ID NO:121 encodes the amino acid sequence represented by SEQ ID NO:122.

Expression plasmid of *Bombyx* odorant receptor OR56 (hereinafter, may be referred to as "BmOR56")

Double-stranded DNA having the nucleotide sequence set forth in SEQ ID NO:123 in any one of the DNA strands was synthesized. PCR was performed using 100 ng of the double-stranded DNA having the nucleotide sequence set forth in SEQ ID NO:123, and using 1 μL of 10 μM forward primer BmOR56-5' (5'-tggaattctgcagatcaccatgaagctcctggagaagctag; SEQ ID NO:124), 1 μL of 10 μM reverse primer BmOR56-3' (5'-gccactgtgctggattcatgttttattcatttgcgactgac; SEQ ID NO:125), and 1 μL of KOD Plus neo DNA polymerase (manufactured by Toyobo Co., Ltd.). The PCR reaction was carried out under the following conditions: (1) 94° C., for 2 minutes, (2) 98° C., for 10 seconds, (3) 63° C., for 30 seconds, and (4) 68° C., for 1.5 minutes, and the processes of (2) to (4) were repeatedly carried out for 35 cycles. The PCR product thus obtained was linked to pcDNA3.1 (manufactured by invitrogen, Inc.) that had been digested with EcoRV, using In-Fusion HD Cloning Kit (manufactured by Takara Bio, Inc.). The DNA thus linked was incorporated into Escherichia coli, and the bacterial cells were cultured. Thus, an expression plasmid named pcDNA3.1-BmOR56 was obtained. The nucleotide sequence of the expression plasmid pcDNA3.1-BmOR56 was analyzed using a DNA sequencer, and it was found that the expression plasmid contained the nucleotide sequence set forth in SEQ ID NO:123. The nucleotide sequence set forth in SEQ ID NO:123 encodes the amino acid sequence set forth in SEQ ID NO:126.

Production of Aequorin Expression Plasmid 50 ng of a plasmid obtained by cloning the nucleotide sequence set forth in SEQ ID NO:127, which encodes aequorin, into pMD19 vector (pMD19-AEQ) was used as a template, and PCR was performed using 1 μL of 1 μM forward primer AEQ-5' (5'-caccatgacaagcaaacaatactc; SEQ ID NO:128), 1 μL of 10 μM reverse primer AEQ-3' (5'-ttaggggacagctccaccgtag; SEQ ID NO:129), and 1 μL of KOD Plus neo DNA polymerase (manufactured by Toyobo Co., Ltd.). The PCR reaction was carried out under the following conditions: (1) 95° C., for 3 minutes, (2) 95° C., for 30 seconds, (3), 60° C., for 30 seconds, and (4) 68° C., for 1 minute, and the processes of (2) to (4) were repeatedly carried out for 35 cycles. The PCR product thus obtained was subjected to agarose gel electrophoresis, and then about 600-bp DNA detected on the gel was collected. The DNA thus collected was incorporated into pENTR/D-TOPO vector (manufactured by Invitrogen, Inc.), and a plasmid named pENTR-AEQ was obtained. The nucleotide sequence set forth in SEQ ID NO:127 encodes the amino acid sequence set forth in SEQ ID NO:130. 4 μL of pENTR-AEQ, 1 μL of pcDNA6.2V5-DEST, and 2 μl, of LR Clonase II (manufactured by Invitrogen, Inc.) were mixed, and the mixture was maintained for one hour at room temperature. The mixture thus obtained was incorporated into Escherichia coli, and the mixture was amplified. Thereby, an expression plasmid named pcDNA6.2-AEQ was obtained. 100 ng of the plasmid pcDNA6.2-AEQ was used as a template, and PCR was performed using 1 μL of 10 μM forward primer In-Fusion SEQ-5' (5'-gtggcggccgctcgaggccaccatgacaagcaaacaatactc; SEQ ID NO:131), 1 μL, of 10 μM reverse primer In-Fusion AEQ-3' (5'-gccctctagactcgagttaggggacagctccaccgtag; SEQ ID NO:132) and 1 μL of KOD neo Plus DNA polymerase (manufactured by Toyobo Co., Ltd.). The PCR reaction was carried out under the following conditions: (1) 95° C., for 3 minutes, (2) 95° C., for 30 seconds, (3) 60° C., for 30 seconds, and (4) 68° C., for 1 minute, and the processes of (2) to (4) were repeatedly carried out for 35 cycles. The DNA thus obtained was subjected to agarose gel electrophoresis, and then about 600-bp DNA detected on the gel was collected. This DNA was designated as insert DNA1. pcDNA3.1 (manufactured by invitrogen, Inc.) that had been digested with XhoI was used as a vector, and the insert DNA1 was linked to this vector using In-Fusion HD Cloning Kit (manufactured by Takara Bio, Inc.). The DNA thus linked was incorporated into Escherichia coli, and the bacterial cells were cultured. Thus, a plasmid named pcDNA3.1-AEQ was obtained. PCR was performed using 100 ng of pcDNA3.1-AEQ as a template, and using 1 μL of 10 μM forward primer In-Fusion AEQ-5' (5'-gtggcggccgctcgaggccaccatgacaagcaaacaatactc; SEQ ID NO:133), 1 μL of 10 μM reverse primer In-Fusion AEQ-3' (5'-gccctctagactcgagttaggggacagctccaccgtag; SEQ ID NO:134), and 1 μL of KOD Plus neo DNA polymerase (manufactured by Toyobo Co., Ltd.). The PCR reaction as carried out under the following conditions: (1) 95° C., for 3 minutes, (2) 95° C., for 30 seconds, (3) 60° C., for 30 seconds, and (4) 68° C., for 1 minute, and the processes of (2) to (4) were repeatedly carried out for 35 cycles. The DNA thus obtained was subjected to agarose gel electrophoresis, and then about 600-bp DNA detected on the gel was collected, and this was designated as insert DNA2. pcDNA3.1(hygro) (manufactured by Invitrogen, Inc.) that had been digested with XhoI was used as a vector, and the insert DNA2 was linked to this vector using In-Fusion HD Cloning Kit (manufactured by Takara Bio, Inc.), The DNA thus linked was incorporated into Escherichia coli, and the bacterial cells were cultured. Thereby, an expression plasmid named peDNA3.1(hygro)-AEQ was obtained.

Incorporation of Expression Plasmid into Cells

HEK293FT cells (purchased from invitrogen, Inc.) were inoculated into 10-cm Petri dishes at a concentration of $3 \times 10^6$ cells/Petri dish, and the cells were cultured in DMEM medium containing 10% FBS (manufactured by Nacalai Tesque, Inc.) for about 24 hours under the conditions of 37° C. and 5% $CO_2$. 3 μg of any one of the co-receptor expression plasmids produced, 1.5 μg of any one of the odorant receptor expression plasmids produced, and 8 μg of Aequorin expression plasmid were mixed with 12.5 μL of Plus reagent and 31.25 μL of LIPOFECTAMINE LTX (manufactured by Invitrogen, Inc.), and the mixture was maintained for 30 minutes. Subsequently this liquid mixture was transfected into the above-mentioned cells. After 4 hours from the initiation of transfection, the cells were inoculated onto a 96-well plate at a concentration of $9 \times 10^4$ cells/well, and the cells were cultured in DMEM medium containing 10% FBS (manufactured by Nacalai Tesque, Inc.) for about 24 hours under the conditions of 37° C. and 5% $CO_2$. Thereby, transformed cells having a co-receptor expression plasmid, an odorant receptor expression plasmid, and an aequorin expression plasmid transiently incorporated therein were obtained.

Activity Measurement

Aequorin is activated when hound to a calcium ion, and oxidizes a substrate such as coelenterazine, thus emitting light. Therefore, an increase in the intracellular calcium ion concentration in a cell that expresses aequorin is directly exhibited as an increase in the amount of luminescence. Therefore, whether an odorant receptor complex functions an ion channel as a result of addition of a substance to be detected, can be measured from the change in the amount of luminescence.

A culture fluid of the transformed cells was removed, and the medium was exchanged with Hanks-HEPES (20 mM, pH 7.4) including Assay buffer (0.5 μM coelenterazine h (manufactured by Promega Corporation) and 0.3% BSA. culture system was left to stand for another 4 hours at room temperature. Subsequently, a substance to be detected, which corresponded to an odorant receptor, was added to the cell culture using FLEXSTATION 3 (manufactured by Molecular Devices, LLC), and at the same time, the amount of luminescence of the cells was measured. As a control substance, the amount of luminescence in the cells to which dimethyl sulfoxide had been added was designated as 1, and the amount or luminescence of cells to which the substance to be detected was added was calculated as a relative value.

Test Example 1

Cells into which:
an expression plasmid of odorant receptor AaOR8;
an expression plasmid of any one of co-receptor AaORCO or DmORCO, or various chimeric co-receptors Dm-AaORCO having different positions of recombination [Dm(NT-EC1)AaORCO, Dm(NT-TM3)AaOROC, Dm(NT-TM4)AaORCO, Dm(NT-TM5)AaORCO, or Dm(NT-TM6)AaORCO]; and
an aequorin expression plasmid
had been incorporated were used, and the amount of luminescence was measured as explained above. 1-Octen-3-ol was used as a substance to be detected, and 1-octen-3-ol was added to the culture fluid at a concentration of $10^{-4}$ M, $10^{-5}$ M, $10^{-6}$ M, $10^{-7}$ M, $10^{-8}$ M, $10^{-9}$ M, or $10^{-10}$ M. The results are presented in FIG. 1. In cells that expressed an odorant receptor and, among the chimeric co-receptors of DmORCO and AaORCO, chimeric co-receptor [Dm(NT-TM4)AaORCO] in which the amino acid sequence including from the N-terminal domain to the fourth transmembrane domain was derived from a *Drosophila* co-receptor, and the amino acid sequence including from the second intracellular loop to the C-terminal domain was derived from an *Aedes* co-receptor, the increase in the amount of luminescence caused by addition of 1-Octen-3-ol was larger compared to the cells that expressed original AaORCO or DmORCO and an odorant receptor. It was found that cells that expressed an odorant receptor and a chimeric co-receptor [Dm(NT-TM4)AaORCO] in which the amino acid sequence including from the N-terminal domain to the fourth transmembrane domain was derived from a *Drosophila* co-receptor, and the amino acid sequence including from the second intracellular loop to the C-terminal domain was derived from an *Aedes* co-receptor, responded more strongly to 1-octen-3-ol, compared to cells that expressed any one of original AaORCO or DmORCO and an odorant receptor.

Test Example 2

Figure 2:
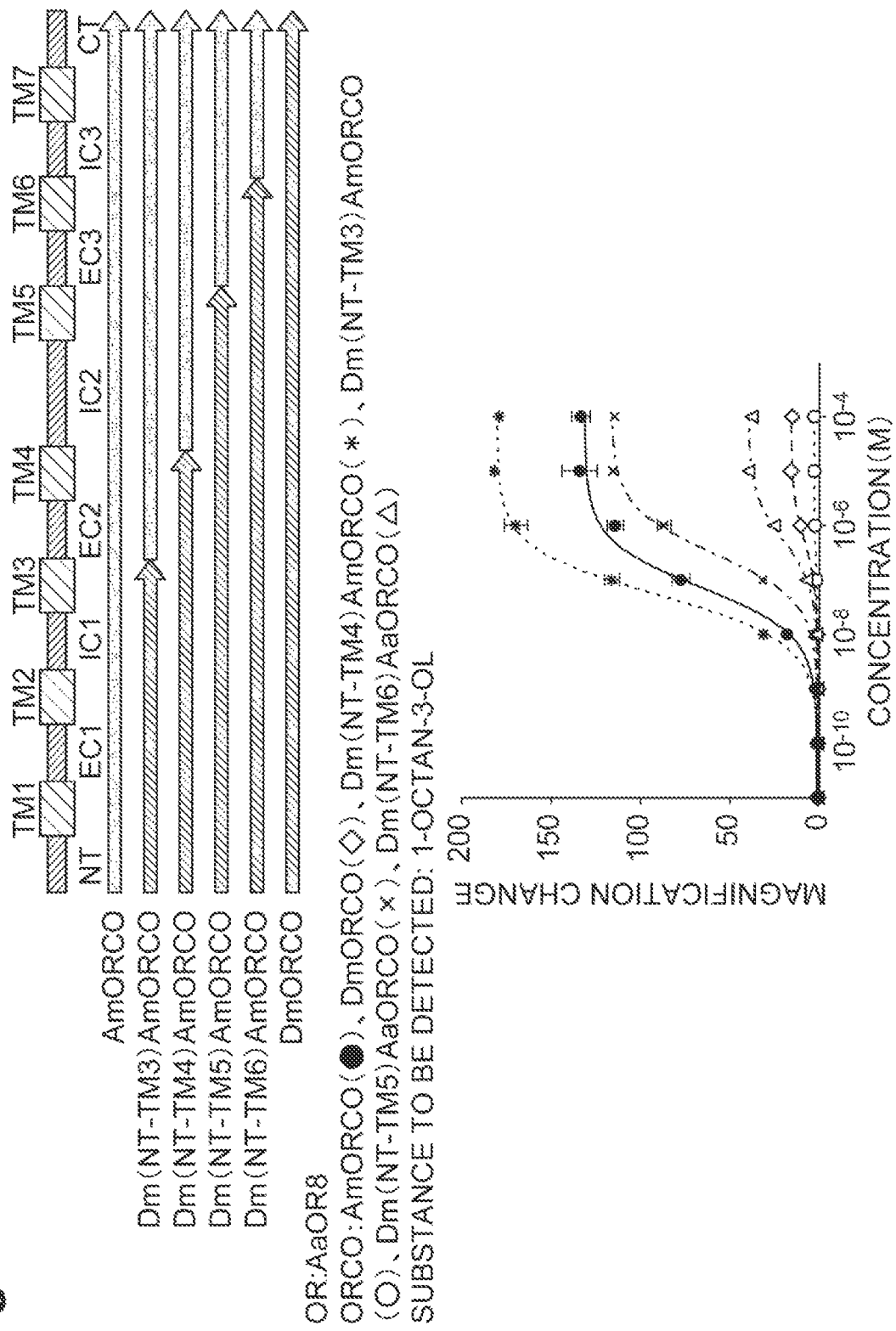
FIG. 2 shows the relative value of the amount of luminescence detected when 1-octen-3-ol was added to a cell that expresses AaOR8 as an odorant receptor and expresses any one of AmORCO, DmORCO, or various chimeric co-receptors (Dm-AmORCO) having different positions of recombination as a co-receptor.

Cells into which:
an expression plasmid of odorant receptor AaOR8;
an expression plasmid of any one of co-receptor AmORCO or DmORCO, or various chimeric co-receptors Dm-AmORCO having different positions of recombination [Dm(NT-TM3)AmOROC, Dm(NT-TM4)AmORCO, Dm(NT-TM5)AmORCO, or Dm(NT-TM6)AmORCO]; and
an aequorin expression plasmid
had been incorporated were used, and the amount of luminescence was measured as explained above. 1-Octen-3-ol was used as a substance to be detected, and 1-octen-3-ol was added to the culture fluid at a concentration of $10^{-4}$ M, $10^{-5}$ M, $10^{-6}$ M, $10^{-7}$ M, $10^{-8}$ M, $10^{-9}$ M, or $10^{-10}$ M. The results are presented in FIG. 2. Also for chimeric co-receptors of DmORCO and AmORCO, similarly to the chimeric co-receptors of DmORCO and AaORCO, in cells that expressed an odorant receptor and chimeric co-receptor [Dm(NT-TM4)AmORCO] in which the amino acid sequence including from the N-terminal domain to the fourth transmembrane domain was derived from a *Drosophila* co-receptor, and the amino acid sequence including from the second intracellular loop to the C-terminal domain was derived from an *Apis* co-receptor, the increase in the amount of luminescence caused by addition of 1-octen-3-ol was larger compared to the cells that expressed any one of original AmORCO or DmORCO and an odorant receptor.

From the results of Test Examples 1 and 2, it was found that in order to produce a chimeric co-receptor having a high intensity of response to a ligand when the chimeric co-receptor is bound to an odorant receptor to form an odorant receptor complex, it is important to recombine the amino acid sequences of the original two kinds of co-receptors near the C-terminus of the fourth transmembrane domain.

Test Example 3

Figure 3:
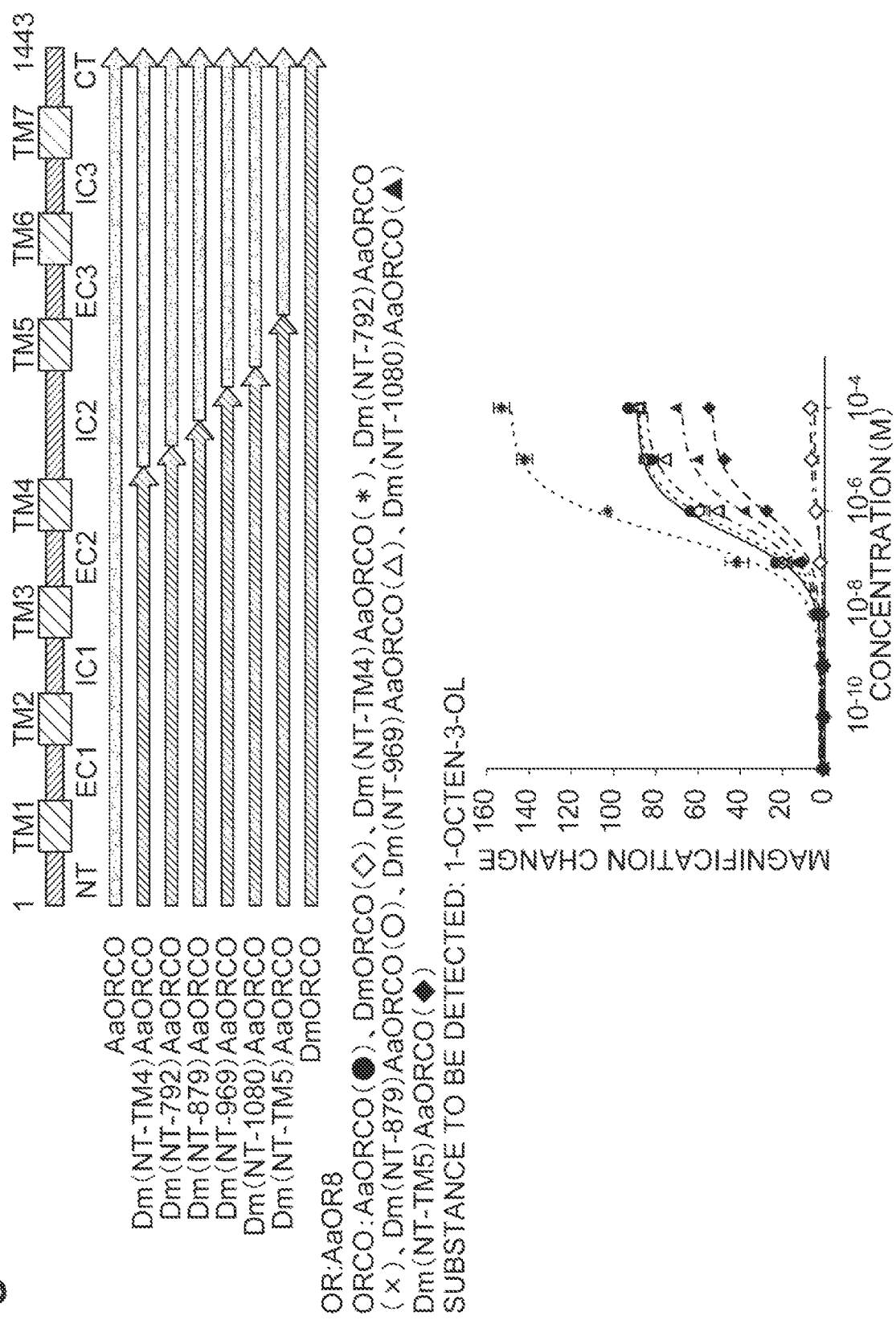
FIG. 3 shows the relative value of the amount of luminescence detected when 1-octen-3-ol was added to a cell that expresses AaOR8 as an odorant receptor and expresses any one of AaORCO, DmORCO, or various chimeric co-receptors (Dm-AaORCO) as a co-receptor.

Cells into which:
an expression plasmid of odorant receptor AaOR8;
an expression plasmid of any one of co-receptor AaORCO or DmORCO, or various chimeric co-receptors Dm-AaORCO having different positions of recombination [Dm(NT-TM4)AaORCO, Dm(NT-792)AaORCO, Dm(NT-879)AaORCO, Dm(NT-969)AaORCO, Dm(NT-1080)AaORCO, Dm(NT-TM5)AaORCO, or Dm (NT-636)AaORCO]; and
an aequorin expression plasmid
had been incorporated were used, and the amount of luminescence was measured as explained above. 1-Octen-3-ol was used as a substance to be detected, and 1-octen-3-ol was added to the culture fluid at a concentration of $10^{-4}$ M, $10^{-5}$ M, $10^{-6}$ M, $10^{-7}$ M, $10^{-8}$ M, $10^{-9}$ M, or $10^{-10}$ M. The results are presented in FIG. 3 and FIG. 4. In cells that expressed Dm(NT-TM4)AaORCO and an odorant, receptor, the intensity of response to 1-octen-3-ol was higher, compared to cells that expressed any one of original AaORCO or DmORCO and an odorant receptor. In contrast, in cells that expressed an odorant receptor and Dm(792)AaORCO in which the DmORCO-derived amino acid sequence was longer by thirty amino acid residues on the C-terminal side than Dm(NT-TM4)AaORCO the intensity of response to 1-octen-3-ol was decreased compared to cells that expressed original AaORCO and an odorant receptor. Also, in cells that expressed an odorant receptor and Dm(NT-636)AaORCO in which the DmORCO-derived amino acid sequence was shorter by 22 amino acid residues on the N-terminal side than Dm(NT-TM4)AaORCO, the intensity of response to 1-octen-3-ol was decreased compared to cells that expressed any one of original AaORCO or DmORCO and an odorant receptor. From these results, it was suggested that it is preferable for the amino acid sequence derived from ORCO of a first insect in the chimeric co-receptor to include from the N-terminal to any one amino acid residue in the range of about twenty amino acid residues before and after the farthest C-terminal amino acid residue of the fourth transmembrane domain.

Test Example 4

Figure 5:
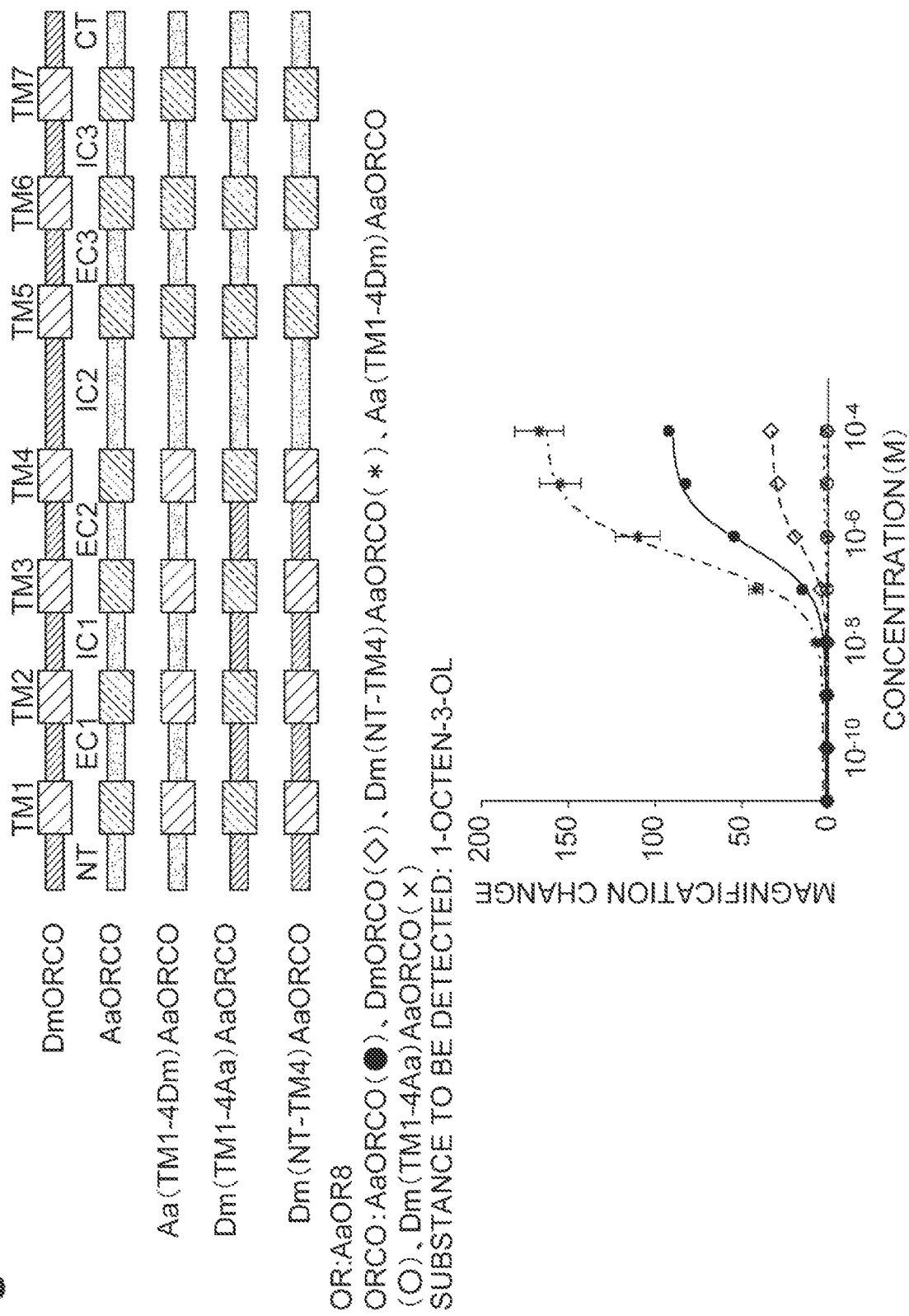
FIG. 5 shows the relative value of the amount of luminescence detected when 1-octen-3-ol was added to a cell that expresses AaOR8 as an odorant receptor and expresses, as a co-receptor, any one of AaORCO, DmORCO, Dm(NT-TM4)AaORCO, or various chimeric co-receptors (Dm-AaORCO) obtained by recombining a transmembrane domain or an intracellular domain and an extracellular domain.

Cells into which:

an expression plasmid of odorant receptor AaOR8;

an expression plasmid of any one of co-receptor AaORCO or DmORCO, or various chimeric co-receptors Dm(NT-TM4)AaORCO, Aa(TM1-4Dm)AaORCO obtained by further incorporating only the first to fourth transmembrane domains from AaORCO into DmORCO, or Dm(TM1-4Aa)AaORCO obtained by further incorporating the N-terminal domain, the first and second extracellular domains, and the first intracellular domain from AaORCO into DmORCO; and an aequorin expression plasmid had been incorporated were used, and the amount of luminescence was measured as explained above. 1-Octen-3-ol was used as a substance to be detected, and 1-octen-3-ol was added to the culture fluid at a concentration of $10^{-4}$ M, $10^{-5}$ M, $10^{-6}$ M, $10^{-7}$ M, $10^{-8}$ M, $10^{-9}$ M, or $10^{-10}$ M. The results are presented in FIG. 5. As a result, in cells that expressed an odorant receptor and a chimeric co-receptor obtained by incorporating only the transmembrane domains or the intracellular domains and extracellular domains [Aa(TM1-4Dm)AaORCO or Dm(TM1-4Aa)AaORCO], the intensity of response to 1-octen-3-ol was decreased compared to cells that expressed any one of original AaORCO or DmORCO and an odorant receptor. It was found that in order to produce a chimeric co-receptor having a high intensity of response to a ligand when bound to an odorant receptor to form an odorant receptor complex, it is necessary that the domains from the N-terminal to the fourth transmembrane domain are contiguous and are domains derived from ORCO of the same species.

Test Example 5

Figure 6:
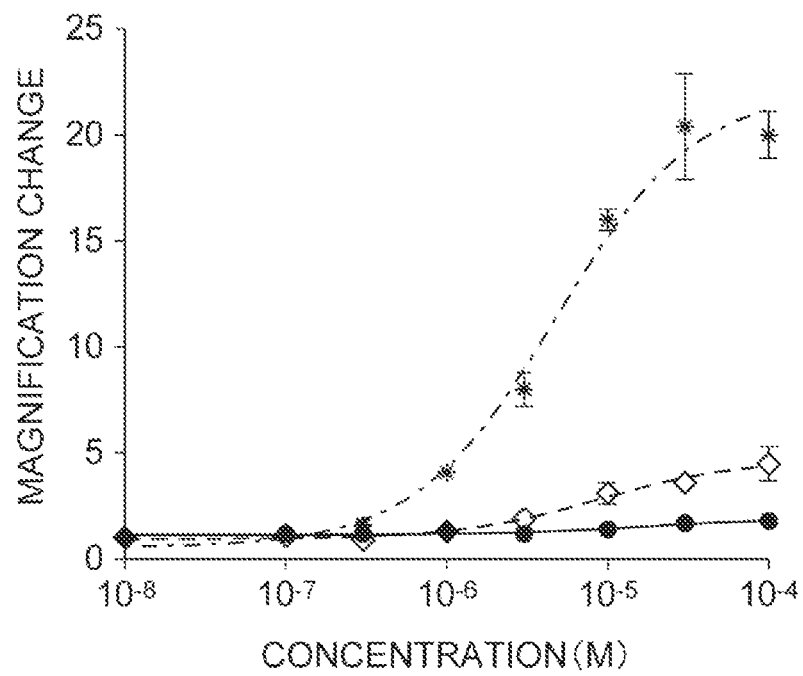
FIG. 6 shows the relative value of the amount of luminescence detected when pentyl acetate was added to a cell that expresses DmOR47a as an odorant receptor and expresses any one DmORCO, AmORCO, or Dm(NT-TM4) AmORCO as a co-receptor.

Cells into which:

an expression plasmid of odorant receptor DmOR47a;

an expression plasmid of any one of co-receptor DmORCO or AmORCO, or chimeric co-receptor Dm(NT-TM4)AmORCO; and an aequorin expression plasmid had been incorporated were used, and the amount of luminescence was measured as explained above. Pentyl acetate was used as a substance to be detected, and pentyl acetate was added to the culture fluid at a concentration of $10^{-4}$ M, $10^{-4.5}$ M, $10^{-5}$ M, $10^{-5.5}$ M, $10^{-6}$ M, $10^{-6.5}$ M, or $10^{-7}$ M. The results are presented in FIG. 6. It was found that cells that expressed Dm(NT-TM4)AmORCO and an odorant receptor responded more strongly to pentyl acetate, compared to cells that expressed any one of original DmORCO or AmORCO and an odorant receptor.

Test Example 6

Figure 7:
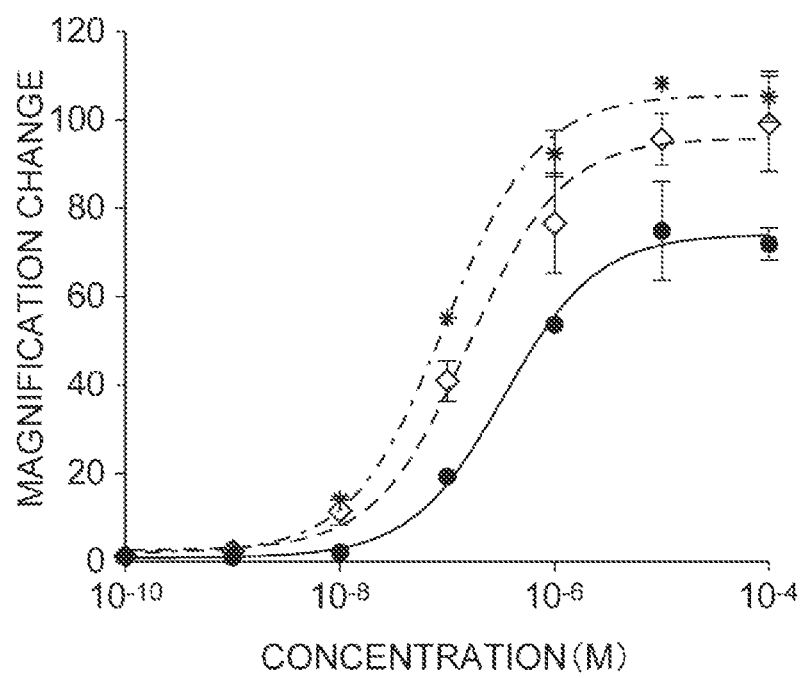
FIG. 7 shows the relative value of the amount of luminescence detected when 1-octen-3-ol was added to a cell that expresses AaOR8 as an odorant receptor and expresses any one of AaORCO, AmORCO, or Aa(NT-TN44)AmORCO as a co-receptor.

Cells into which:

an expression plasmid of odorant receptor AaOR8;

an expression plasmid of any one of co-receptor AaORCO or AmORCO, or chimeric co-receptor Aa(NT-TM4)AmORCO; and aequorin expression plasmid had been incorporated were used, and the amount of luminescence was measured as explained above. 1-Octan-3-ol was used as a substance to be detected, and 1-octan-3-ol was added to the culture fluid at a concentration of $10^{-4}$ M, $10^{-5}$ M, $10^{-6}$ M, $10^{-7}$ M, $10^{-8}$ M, $10^{-9}$ M, or $10^{-10}$ M. The results are presented in FIG. 7. It was found that cells that expressed Aa(NT-TM4)AmORCO and an odorant receptor responded more strongly to 1-octan-3-ol, compared to cells that expressed any one of original AaORCO or AmORCO and an odorant receptor.

Test Example 7

Figure 8:
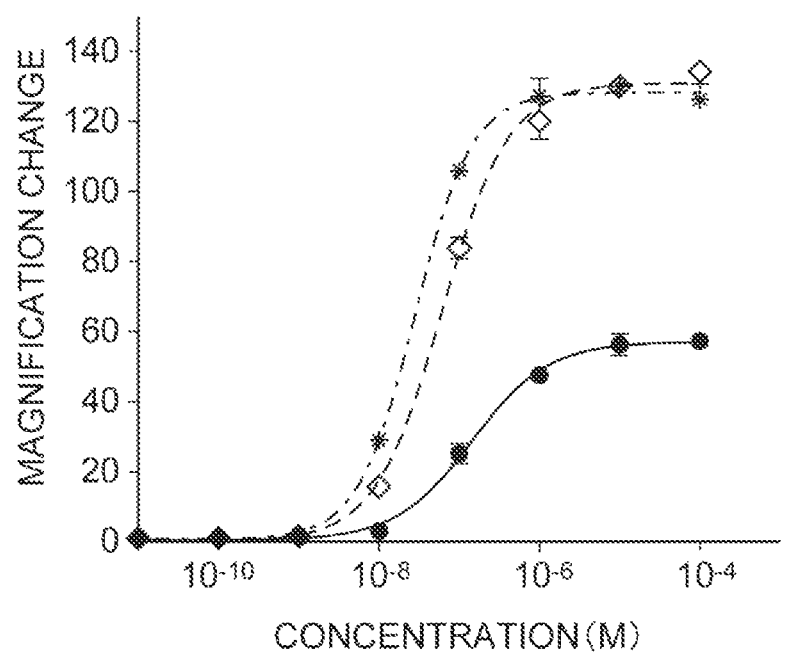
FIG. 8 shows the relative value of the amount of luminescence detected when 1-octen-3-ol was added to a cell that expresses AaOR8 as an odorant receptor and expresses any one of AgORCO, AmORCO, or Ag(NT-TM4)AmORCO as a co-receptor.

Cells into which:

an expression plasmid of odorant receptor AaOR8;

an expression plasmid of any one of co-receptor AgORCO or AmORCO, or chimeric co-receptor Ag(NT-TM4)AmORCO; and an aequorin expression plasmid had been incorporated were used, and the amount of luminescence was measured as explained above. 1-Octan-3-ol was used as a substance to be detected, and 1-octan-3-ol was added to the culture fluid at a concentration of $10^{-4}$ M, $10^{-5}$ M, $10^{-6}$ M, $10^{-7}$ M, $10^{-8}$ M, $10^{-9}$ M, or $10^{-10}$ M. The results are presented in FIG. 8. It was found that cells that expressed Ag(NT-TM4)AmORCO and an odorant receptor when bound to an odorant receptor to form an odorant receptor complex, responded to 1-octan-3-ol at a lower concentration compared to cells that expressed any one of original AaORCO or AmORCO and an odorant receptor.

Test Example 8

Figure 9:
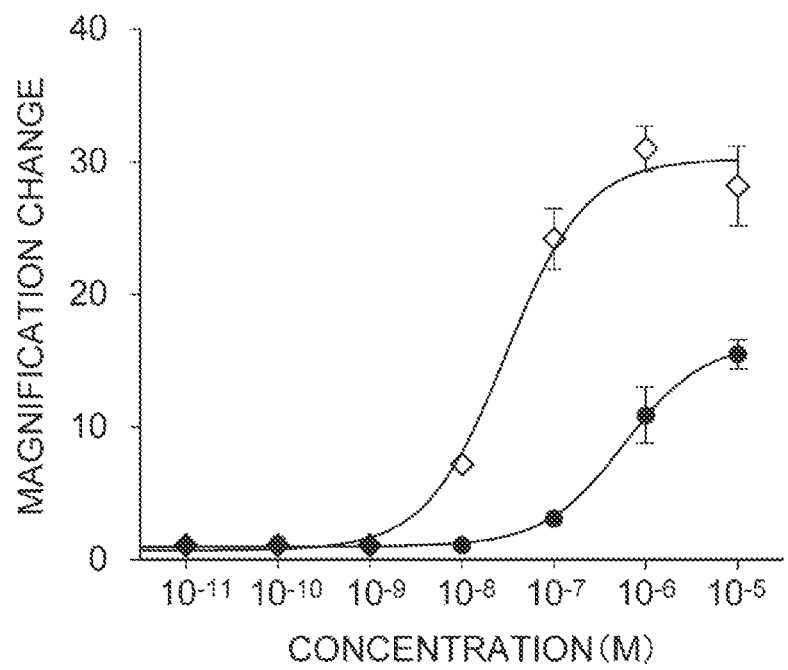
FIG. 9 shows the relative value of the amount of luminescence detected when cis-jasmone was added to a cell that expresses BmOR56 as an odorant receptor and expresses any one of BmORCO or Dm(NT-TM4)AmORCO as a co-receptor.

Cells into which:

an expression plasmid of odorant receptor BmOR56;

an expression plasmid of any one of co-receptor BmORCO or chimeric co-receptor Dm(NT-TM4)AmORCO; and an aequorin expression plasmid had been incorporated were used, and the amount of luminescence was measured as explained above. Cis-jasmone was used as a substance to be detected, and cis-jasmone was added to the culture fluid at a concentration of $10^{-5}$ M, $10^{-6}$ M, $10^{-7}$ M, $10^{-8}$ M, $10^{-9}$ M, $10^{-10}$ M, or $10^{-11}$ M. The results are presented in FIG. 9. It was found that cells that expressed Dm(NT-TM4)AmORCO and BmOR56 responded more strongly to cis-jasmone than cells that expressed BmORCO and BmOR56. Furthermore, from the results of Examples 7 and 8, it was found that cells that expressed the chimeric co-receptor of the present embodiment and an odorant receptor derived from an insect of a variety different from the respective insects from which the original ORCO's constituting a chimeric co-receptor are derived, respond strongly or with high sensitivity to a ligand, compared to cells that express be original odorant receptor co-receptor and the above-mentioned odorant receptor.

The invention claimed is:

1. A chimeric odorant receptor co-receptor protein comprising:
    an amino terminal portion derived from an odorant receptor co-receptor protein from a first organism and
    a carboxyl-terminal portion derived from an odorant receptor co-receptor protein from a second organism,
    wherein the amino acid terminal portion and the carboxyl-terminal portion are delineated from one another at an amino acid residue at a position between
        twenty amino acid residues before and after the farthest carboxyl-terminal amino acid residue of the fourth transmembrane domain of the chimeric odorant receptor co-receptor protein, wherein said farthest carboxyl-terminal amino acid residue of the fourth transmembrane domain corresponds to position 234 in the amino acid sequence of SEQ ID NO:6 and position 232 in the amino acid sequence of SEQ ID NO:14, and
        wherein the first organism is *Drosophila melanogaster* and the second organism is *Apis mellifera*.

2. The chimeric odorant receptor co-receptor protein according to claim 1, wherein the amino terminal portion comprises amino acid sequence residues from position 1 to position 214-254 of SEQ ID NO:6 and the carboxyl-terminal portion comprises amino acid residues from position 212-252 to position 477 of SEQ ID NO:14.

3. The chimeric odorant receptor co-receptor protein according to claim 1, comprising an amino acid sequence having the amino acid sequence set forth in SEQ ID NO:100.

4. A chimeric odorant receptor co-receptor protein comprising:
    an amino terminal portion derived from an odorant receptor co-receptor protein from a first organism and
    a carboxyl-terminal portion derived from an odorant receptor co-receptor protein from a second organism,
    wherein the amino acid terminal portion and the carboxyl-terminal portion are delineated from one another at an amino acid residue at a position between twenty amino acid residues before and after the farthest carboxyl-terminal amino acid residue of the fourth transmembrane domain of the chimeric odorant receptor co-receptor protein, wherein said farthest carboxyl-terminal amino acid residue of the fourth transmembrane domain corresponds to position 234 in the amino acid sequence of SEQ ID NO:6 and position 233 in the amino acid sequence of SEQ ID NO:10, and
    wherein the first insect is *Drosophila melanogaster*, and the second insect is *Aedes aegypti*.

5. The chimeric odorant receptor co-receptor protein according to claim 4, comprising an amino acid sequence having the amino acid sequence set forth in SEQ ID NO:71.

6. A chimeric odorant receptor co-receptor protein comprising:
    an amino terminal portion derived from an odorant receptor co-receptor protein from a first organism and
    a carboxyl-terminal portion derived from an odorant receptor co-receptor protein from a second organism,
    wherein the amino acid terminal portion and the carboxyl-terminal portion are delineated from one another at an amino acid residue at a position between twenty amino acid residues before and after the farthest carboxyl-terminal amino acid residue of the fourth transmembrane domain of the chimeric odorant receptor co-receptor protein, wherein said farthest carboxyl-terminal amino acid residue of the fourth transmembrane domain corresponds to position 233 in the amino acid sequence of SEQ ID NO:10 and position 232 in the amino acid sequence of SEQ ID NO:14, and
    wherein the first insect is *Aedes aegypti*, and the second insect is *Apis mellifera*.

7. The chimeric odorant receptor co-receptor protein according to claim 6, comprising an amino acid sequence having the amino acid sequence set forth in SEQ ID NO:108.

8. The chimeric odorant receptor co-receptor protein according to claim 4, wherein the amino terminal portion comprises amino acid sequence residues from position 1 to position 214-254 of SEQ ID NO:6 and the carboxyl-terminal portion comprises amino acid residues from position 213-253 to position 478 of SEQ ID NO:10.

9. The chimeric odorant receptor co-receptor protein according to claim 6, wherein the amino terminal portion comprises amino acid sequence residues from position 1 to position 213-253 of SEQ ID NO:10 and the carboxyl-terminal portion comprises amino acid residues from position 212-252 to position 477 of SEQ ID NO:14.

* * * * *

SEQUENCE LISTING

```
<160> NUMBER OF SEQ ID NOS: 137

<210> SEQ ID NO 1
<211> LENGTH: 234
<212> TYPE: PRT
<213> ORGANISM: Drosophila melanogaster
```

<400> SEQUENCE: 1

```
Met Thr Thr Ser Met Gln Pro Ser Lys Tyr Thr Gly Leu Val Ala Asp
1               5                   10                  15

Leu Met Pro Asn Ile Arg Ala Met Lys Tyr Ser Gly Leu Phe Met His
            20                  25                  30

Asn Phe Thr Gly Gly Ser Ala Phe Met Lys Lys Val Tyr Ser Ser Val
        35                  40                  45

His Leu Val Phe Leu Leu Met Gln Phe Thr Phe Ile Leu Val Asn Met
 50                  55                  60

Ala Leu Asn Ala Glu Glu Val Asn Glu Leu Ser Gly Asn Thr Ile Thr
65                  70                  75                  80

Thr Leu Phe Phe Thr His Cys Ile Thr Lys Phe Ile Tyr Leu Ala Val
                85                  90                  95

Asn Gln Lys Asn Phe Tyr Arg Thr Leu Asn Ile Trp Asn Gln Val Asn
            100                 105                 110

Thr His Pro Leu Phe Ala Glu Ser Asp Ala Arg Tyr His Ser Ile Ala
        115                 120                 125

Leu Ala Lys Met Arg Lys Leu Phe Phe Leu Val Met Leu Thr Thr Val
130                 135                 140

Ala Ser Ala Thr Ala Trp Thr Thr Ile Thr Phe Phe Gly Asp Ser Val
145                 150                 155                 160

Lys Met Val Val Asp His Glu Thr Asn Ser Ser Ile Pro Val Glu Ile
                165                 170                 175

Pro Arg Leu Pro Ile Lys Ser Phe Tyr Pro Trp Asn Ala Ser His Gly
            180                 185                 190

Met Phe Tyr Met Ile Ser Phe Ala Phe Gln Ile Tyr Tyr Val Leu Phe
        195                 200                 205

Ser Met Ile His Ser Asn Leu Cys Asp Val Met Phe Cys Ser Trp Leu
210                 215                 220

Ile Phe Ala Cys Glu Gln Leu Gln His Leu
225                 230
```

<210> SEQ ID NO 2
<211> LENGTH: 246
<212> TYPE: PRT
<213> ORGANISM: Apis mellifera

<400> SEQUENCE: 2

```
Lys Asn Ile Met Lys Pro Leu Met Glu Phe Ser Ala Thr Leu Asp Thr
1               5                   10                  15

Val Val Pro Asn Ser Gly Glu Leu Phe Lys Ala Gly Ser Ala Glu Gln
            20                  25                  30

Pro Lys Glu Gln Glu Pro Leu Pro Pro Val Thr Pro Pro Gln Gly Glu
        35                  40                  45

Asn Met Leu Asp Met Asp Leu Arg Gly Ile Tyr Ser Asn Arg Thr Asp
     50                  55                  60

Phe Thr Thr Thr Phe Arg Pro Thr Ala Gly Met Thr Phe Asn Gly Gly
65                  70                  75                  80

Val Gly Pro Asn Gly Leu Thr Lys Lys Gln Glu Met Leu Val Arg Ser
                85                  90                  95

Ala Ile Lys Tyr Trp Val Glu Arg His Lys His Ile Val Arg Leu Val
            100                 105                 110

Thr Ala Ile Gly Asp Ala Tyr Gly Val Ala Leu Leu Leu His Met Leu
        115                 120                 125
```

```
Thr Thr Thr Ile Thr Leu Thr Leu Leu Ala Tyr Gln Ala Thr Lys Ile
    130                 135                 140

His Ala Val Asp Thr Tyr Ala Ala Ser Val Val Gly Tyr Leu Leu Tyr
145                 150                 155                 160

Ser Leu Gly Gln Val Phe Met Leu Cys Ile Phe Gly Asn Arg Leu Ile
                165                 170                 175

Glu Glu Ser Ser Ser Val Met Glu Ala Ala Tyr Ser Cys His Trp Tyr
            180                 185                 190

Asp Gly Ser Glu Glu Ala Lys Thr Phe Val Gln Ile Val Cys Gln Gln
        195                 200                 205

Cys Gln Lys Ala Met Ser Ile Ser Gly Ala Lys Phe Phe Thr Val Ser
    210                 215                 220

Leu Asp Leu Phe Ala Ser Val Leu Gly Ala Met Val Thr Tyr Phe Met
225                 230                 235                 240

Val Leu Val Gln Leu Lys
                245

<210> SEQ ID NO 3
<211> LENGTH: 32
<212> TYPE: DNA
<213> ORGANISM: Artificial Sequence
<220> FEATURE:
<223> OTHER INFORMATION: synthetic

<400> SEQUENCE: 3
caccatgaca acctcgatgc agccgagcaa gt                                32

<210> SEQ ID NO 4
<211> LENGTH: 29
<212> TYPE: DNA
<213> ORGANISM: Artificial Sequence
<220> FEATURE:
<223> OTHER INFORMATION: synthetic

<400> SEQUENCE: 4
ttacttgagc tgcaccagca ccataaagt                                    29

<210> SEQ ID NO 5
<211> LENGTH: 1461
<212> TYPE: DNA
<213> ORGANISM: Drosophila melanogaster

<400> SEQUENCE: 5
atgacaacct cgatgcagcc gagcaagtac acgggcctgg tcgccgacct gatgcccaac      60
atccgggcga tgaagtactc cggcctgttc atgcacaact tcacgggcgg cagtgccttc     120
atgaagaagg tgtactcctc cgtgcacctg gtgttcctcc tcatgcagtt caccttcatc     180
ctggtcaaca tggccctgaa cgccgaggag gtcaacgagc tgtcgggcaa cacgatcacg     240
accctcttct tcacccactg catcacgaag tttatctacc tggctgttaa ccagaagaat     300
ttctacagaa cattgaatat atggaaccag gtgaacacgc atcccttgtt cgccgagtcg     360
gatgctcgtt accattcgat cgcactggcg aagatgagga agctgttctt tctggtgatg     420
ctgaccacag tcgcctcggc caccgcctgg accacgatca ccttctttgg cgacagcgta     480
aaaatggtgg tggaccatga gacgaactcc agcatcccgg tggagatacc ccggctgccg     540
attaagtcct ctacccgtg gaacgccagc cacggcatgt tctacatgat cagctttgcc     600
tttcagatct actacgtgct cttctcgatg atccactcca atctatgcga cgtgatgttc     660
```

-continued

```
tgctcttggc tgatattcgc ctgcgagcag ctgcagcact tgaagggcat catgaagccg    720
ctgatggagc tgtccgcctc gctggacacc tacaggccca actcggcggc cctcttcagg    780
tccctgtcgg ccaactccaa gtcggagcta attcataatg aagaaaagga tcccggcacc    840
gacatggaca tgtcgggcat ctacagctcg aaagcggatt ggggcgctca gtttcgagca    900
ccctcgacac tgcagtcctt tggcgggaac gggggcggag gcaacgggtt ggtgaacggc    960
gctaatccca acgggctgac caaaaagcag gagatgatgg tgcgcagtgc catcaagtac    1020
tgggtcgagc ggcacaagca cgtggtgcga ctggtggctg ccatcggcga tacttacgga    1080
gccgccctcc tcctccacat gctgacctcg accatcaagc tgaccctgct ggcataccag    1140
gccaccaaaa tcaacggagt gaatgtctac gccttcacag tcgtcggata cctaggatac    1200
gcgctggccc aggtgttcca cttttgcatc tttggcaatc gtctgattga agagagttca    1260
tccgtcatgg aggccgccta ctcgtgccac tggtacgatg ctccgagga ggccaagacc    1320 ttcgtccaga tcgtgtgcca gcagtgccag aaggcgatga gcatatcggg agcgaaattc    1380
ttcaccgtct ccctggattt gtttgcttcg gttctgggtg ccgtcgtcac ctactttatg    1440
gtgctggtgc agctcaagta a                                              1461
```

<210> SEQ ID NO 6
<211> LENGTH: 486
<212> TYPE: PRT
<213> ORGANISM: Drosophila melanogaster

<400> SEQUENCE: 6

```
Met Thr Thr Ser Met Gln Pro Ser Lys Tyr Thr Gly Leu Val Ala Asp
1               5                   10                  15

Leu Met Pro Asn Ile Arg Ala Met Lys Tyr Ser Gly Leu Phe Met His
                20                  25                  30

Asn Phe Thr Gly Gly Ser Ala Phe Met Lys Lys Val Tyr Ser Ser Val
            35                  40                  45

His Leu Val Phe Leu Leu Met Gln Phe Thr Phe Ile Leu Val Asn Met
        50                  55                  60

Ala Leu Asn Ala Glu Glu Val Asn Glu Leu Ser Gly Asn Thr Ile Thr
65                  70                  75                  80

Thr Leu Phe Phe Thr His Cys Ile Thr Lys Phe Ile Tyr Leu Ala Val
                85                  90                  95

Asn Gln Lys Asn Phe Tyr Arg Thr Leu Asn Ile Trp Asn Gln Val Asn
                100                 105                 110

Thr His Pro Leu Phe Ala Glu Ser Asp Ala Arg Tyr His Ser Ile Ala
            115                 120                 125

Leu Ala Lys Met Arg Lys Leu Phe Phe Leu Val Met Leu Thr Thr Val
        130                 135                 140

Ala Ser Ala Thr Ala Trp Thr Thr Ile Thr Phe Phe Gly Asp Ser Val
145                 150                 155                 160

Lys Met Val Val Asp His Glu Thr Asn Ser Ser Ile Pro Val Glu Ile
                165                 170                 175

Pro Arg Leu Pro Ile Lys Ser Phe Tyr Pro Trp Asn Ala Ser His Gly
            180                 185                 190

Met Phe Tyr Met Ile Ser Phe Ala Phe Gln Ile Tyr Tyr Val Leu Phe
        195                 200                 205

Ser Met Ile His Ser Asn Leu Cys Asp Val Met Phe Cys Ser Trp Leu
    210                 215                 220

Ile Phe Ala Cys Glu Gln Leu Gln His Leu Lys Gly Ile Met Lys Pro
```

```
                    225                 230                 235                 240

Leu Met Glu Leu Ser Ala Ser Leu Asp Thr Tyr Arg Pro Asn Ser Ala
                245                 250                 255

Ala Leu Phe Arg Ser Leu Ser Ala Asn Ser Lys Ser Glu Leu Ile His
                260                 265                 270

Asn Glu Glu Lys Asp Pro Gly Thr Asp Met Asp Met Ser Gly Ile Tyr
                275                 280                 285

Ser Ser Lys Ala Asp Trp Gly Ala Gln Phe Arg Ala Pro Ser Thr Leu
                290                 295                 300

Gln Ser Phe Gly Gly Asn Gly Gly Gly Asn Gly Leu Val Asn Gly
305                 310                 315                 320

Ala Asn Pro Asn Gly Leu Thr Lys Lys Gln Glu Met Met Val Arg Ser
                325                 330                 335

Ala Ile Lys Tyr Trp Val Glu Arg His Lys His Val Val Arg Leu Val
                340                 345                 350

Ala Ala Ile Gly Asp Thr Tyr Gly Ala Ala Leu Leu Leu His Met Leu
                355                 360                 365

Thr Ser Thr Ile Lys Leu Thr Leu Leu Ala Tyr Gln Ala Thr Lys Ile
                370                 375                 380

Asn Gly Val Asn Val Tyr Ala Phe Thr Val Val Gly Tyr Leu Gly Tyr
385                 390                 395                 400

Ala Leu Ala Gln Val Phe His Phe Cys Ile Phe Gly Asn Arg Leu Ile
                405                 410                 415

Glu Glu Ser Ser Ser Val Met Glu Ala Ala Tyr Ser Cys His Trp Tyr
                420                 425                 430

Asp Gly Ser Glu Glu Ala Lys Thr Phe Val Gln Ile Val Cys Gln Gln
                435                 440                 445

Cys Gln Lys Ala Met Ser Ile Ser Gly Ala Lys Phe Phe Thr Val Ser
                450                 455                 460

Leu Asp Leu Phe Ala Ser Val Leu Gly Ala Val Val Thr Tyr Phe Met
465                 470                 475                 480

Val Leu Val Gln Leu Lys
                485

<210> SEQ ID NO 7
<211> LENGTH: 44
<212> TYPE: DNA
<213> ORGANISM: Artificial Sequence
<220> FEATURE:
<223> OTHER INFORMATION: synthetic

<400> SEQUENCE: 7
tggaattctg cagatcacca tgaacgtcca accgacaaag tacc            44

<210> SEQ ID NO 8
<211> LENGTH: 37
<212> TYPE: DNA
<213> ORGANISM: Artificial Sequence
<220> FEATURE:
<223> OTHER INFORMATION: synthetic

<400> SEQUENCE: 8
gccactgtgc tggatttatt tcaactgcac caacacc       37

<210> SEQ ID NO 9
<211> LENGTH: 1437
<212> TYPE: DNA
<213> ORGANISM: Aedes aegypti
```

<400> SEQUENCE: 9

```
atgaacgtcc aaccgacaaa gtaccatggg ctggtgctcg acttgatgcc gaacatccgg      60
ctgatgcagg gcttcggtca ctttctgttc cgttacgtaa atgggccggt cctgattcgg     120
aagctgtact cctggtggaa cctgataatg atcctgctgc aatattttgc catcatgggc     180
aatctggtga tgaatacagg ggacgtcaat gagctaacgg caaacaccat aacgacgctg     240
ttttcaccc attctgtgac caagttcatc tacgtcgccg tcaactcgga acatttctac     300
cgcacgctgg gcatctggaa tcaaccgaac agtcattcac ttttgccga atcggatgct     360
cggtaccatt cgattgcgtt ggctaagatg cgaaaactgc tggtcatggt gatggtgact     420
acagtgctat ccgtcgtcgc atggatcacg ataacattct tcggcgatag cgtcaaaaac     480
gtattcgaca agagactaa cgaaacgtat acggtggaaa ttccccgatt gcccatcaag     540
gcttggtacc cgtgggatgc aatgagcgga gtgccgtact ttttctcctt catctaccag     600
gcttatttcc tactgttttc gatgtgccag gccaacctcg ccgatgtgat gttttgctcc     660
tggctgcttt tcacttgcga acagctgcaa catttgaagg gtataatgcg ccccctgatg     720
gaactttccg ccacgctgga cacctaccga ccaaactcgg ctgccctgtt ccgtgtcgct     780
tccgccggat ccaaatcgga gctgattttg aatgaagaga agatcccga cacgaaagat     840
ttcgacttga acggtatcta caactcgaaa gcggactggg gtgcccagtt cagggcgcca     900
tccactttgc aaacgttcgg tgacaatggc atcaatggta atccaaatgg actaaccaag     960
aagcaggaac tgatggtccg aagtgcgatc aagtactggg tggagaggca caagcacgtc    1020
gttcgcctcg tatcggccat cggtgaaact tacggagccg ccctgttgct tcacatgttg    1080
acctcgacca tcaagctgac cctgttggct taccaggcaa ccaaaatcga tgcactcaac    1140
gtttatggac tgaccgtgat cggctatctg gtctatgctc tggctcaggt gttcctgttt    1200
tgcattttcg gcaatcgatt aattgaagag agttcatcag tgatggaggc tgcctactcg    1260
tgccactggt atgacggttc cgaggaagcc aaaactttcg tgcaaatcgt ttgccagcag    1320
tgtcagaaag cgatgaccat atccggggcc aagtttttca ccgtttcact ggatctgttc    1380
gcatcggttc tgggagcggt cgtcacctac ttcatggtgt tggtgcagtt gaaataa       1437
```

<210> SEQ ID NO 10
<211> LENGTH: 478
<212> TYPE: PRT
<213> ORGANISM: Aedes aegypti

<400> SEQUENCE: 10

```
Met Asn Val Gln Pro Thr Lys Tyr His Gly Leu Val Leu Asp Leu Met
1               5                   10                  15

Pro Asn Ile Arg Leu Met Gln Gly Phe Gly His Phe Leu Phe Arg Tyr
            20                  25                  30

Val Asn Gly Pro Val Leu Ile Arg Lys Leu Tyr Ser Trp Trp Asn Leu
        35                  40                  45

Ile Met Ile Leu Leu Gln Tyr Phe Ala Ile Met Gly Asn Leu Val Met
    50                  55                  60

Asn Thr Gly Asp Val Asn Glu Leu Thr Ala Asn Thr Ile Thr Thr Leu
65                  70                  75                  80

Phe Phe Thr His Ser Val Thr Lys Phe Ile Tyr Val Ala Val Asn Ser
                85                  90                  95

Glu His Phe Tyr Arg Thr Leu Gly Ile Trp Asn Gln Pro Asn Ser His
            100                 105                 110
```

```
Ser Leu Phe Ala Glu Ser Asp Ala Arg Tyr His Ser Ile Ala Leu Ala
        115                 120                 125

Lys Met Arg Lys Leu Leu Val Met Val Met Val Thr Thr Val Leu Ser
    130                 135                 140

Val Val Ala Trp Ile Thr Ile Thr Phe Phe Gly Asp Ser Val Lys Asn
145                 150                 155                 160

Val Phe Asp Lys Glu Thr Asn Glu Thr Tyr Thr Val Glu Ile Pro Arg
                165                 170                 175

Leu Pro Ile Lys Ala Trp Tyr Pro Trp Asp Ala Met Ser Gly Val Pro
                180                 185                 190

Tyr Phe Phe Ser Phe Ile Tyr Gln Ala Tyr Phe Leu Leu Phe Ser Met
            195                 200                 205

Cys Gln Ala Asn Leu Ala Asp Val Met Phe Cys Ser Trp Leu Leu Phe
        210                 215                 220

Thr Cys Glu Gln Leu Gln His Leu Lys Gly Ile Met Arg Pro Leu Met
225                 230                 235                 240

Glu Leu Ser Ala Thr Leu Asp Thr Tyr Arg Pro Asn Ser Ala Ala Leu
                245                 250                 255

Phe Arg Val Ala Ser Ala Gly Ser Lys Ser Glu Leu Ile Leu Asn Glu
            260                 265                 270

Glu Lys Asp Pro Asp Thr Lys Asp Phe Asp Leu Asn Gly Ile Tyr Asn
        275                 280                 285

Ser Lys Ala Asp Trp Gly Ala Gln Phe Arg Ala Pro Ser Thr Leu Gln
    290                 295                 300

Thr Phe Gly Asp Asn Gly Ile Asn Gly Asn Pro Asn Gly Leu Thr Lys
305                 310                 315                 320

Lys Gln Glu Leu Met Val Arg Ser Ala Ile Lys Tyr Trp Val Glu Arg
                325                 330                 335

His Lys His Val Val Arg Leu Val Ser Ala Ile Gly Glu Thr Tyr Gly
            340                 345                 350

Ala Ala Leu Leu Leu His Met Leu Thr Ser Thr Ile Lys Leu Thr Leu
        355                 360                 365

Leu Ala Tyr Gln Ala Thr Lys Ile Asp Ala Leu Asn Val Tyr Gly Leu
    370                 375                 380

Thr Val Ile Gly Tyr Leu Val Tyr Ala Leu Ala Gln Val Phe Leu Phe
385                 390                 395                 400

Cys Ile Phe Gly Asn Arg Leu Ile Glu Glu Ser Ser Val Met Glu
                405                 410                 415

Ala Ala Tyr Ser Cys His Trp Tyr Asp Gly Ser Glu Glu Ala Lys Thr
            420                 425                 430

Phe Val Gln Ile Val Cys Gln Gln Cys Gln Lys Ala Met Thr Ile Ser
        435                 440                 445

Gly Ala Lys Phe Phe Thr Val Ser Leu Asp Leu Phe Ala Ser Val Leu
    450                 455                 460

Gly Ala Val Val Thr Tyr Phe Met Val Leu Val Gln Leu Lys
465                 470                 475

<210> SEQ ID NO 11
<211> LENGTH: 1434
<212> TYPE: DNA
<213> ORGANISM: Apis mellifera

<400> SEQUENCE: 11
atgaagttca agcaacaagg gctaatcgcc gacctgatgc ccaatataaa cttgatgaaa      60
```

```
gcaactggcc acttcatgtt caattactac actgacagtt ccacgaaaca catacacaag    120
atctactgta tcgtccacct ggtcctgata ctgatgcagt tcggattctg cggtatcaat    180
ctaatgatgg agagcgaaga cgtggacgat ctcaccgcga acaccatcac catgctcttc    240
ttcacgcaca gcgtggtcaa gctcgtttac ttcgcggtca ggagtaaatt gttctacaga    300
acgcttggca tatggaacaa tccgaacagc catcccctct cgccgagag caacgcgcga     360 taccatcaga tagccgtcaa gaagatgagg atactcctgc tggccgtcat agggaccacg    420
gtgctgtccg ccatttcttg gaccaccatc actttcattg gtgactctgt gaaaaaggtc    480
atcgaccctg tcaccaacga aacgacctac gtcgagatac aaggttgat ggttcgttcc     540 tggtatcctt acgaccccag tcacgggatg cccatattt taacactgat attccaattt     600
tactggctga tattctgcat ggcggacgcg aatctactgg acgtgttgtt ctgctcgtgg    660
ctcctgttcg cttgcgagca gatacagcat ttgaagaata tcatgaagcc tttgatggaa    720
ttcagcgcca cgctggacac cgtcgtgcca aacagtgggg aactgttcaa ggctggcagt    780
gcagagcagc cgaaggaaca ggagccattg ccaccagtca cgccgcccca gggtgaaaac    840
atgttggaca tggatcttcg agggatatat agcaacagga ccgacttcac gaccaccttc    900
cggccaactg ctggaatgac gttcaacggc ggggtcgggc caaatgggtt gaccaagaaa    960
caggaaatgc tggtacgaag cgccatcaag tactgggtag agagacacaa gcatatcgtt   1020
agactcgtaa ctgcaattgg agacgcctat ggtgtagctt tgctgctaca tatgttgact   1080
actactatta cgttaacttt gctcgcttac caagcaacaa agatacatgc agtagataca   1140
tacgcagcat cagtagtagg ttatttgcta tattctttag acaagtctt tatgctctgt    1200 atatttggaa atcgtctcat tgaagagagc tcatcagtga tggaagcagc ttattcttgt   1260
cactggtatg atggatcaga ggaggccaaa acatttgtac agattgtttg ccagcagtgt   1320
cagaaagcga tgtcgatttc agggcaaag ttcttcactg tatctttgga tctctttgct    1380
tcggtgttgg gagctatggt tacctacttc atggtgttgg tgcaactgaa gtga          1434
```

<210> SEQ ID NO 12  
<211> LENGTH: 44  
<212> TYPE: DNA  
<213> ORGANISM: Artificial Sequence  
<220> FEATURE:  
<223> OTHER INFORMATION: synthetic

<400> SEQUENCE: 12

```
tggaattctg cagatcacca tgaagttcaa gcaacaaggg ctaa                      44
```

<210> SEQ ID NO 13  
<211> LENGTH: 42  
<212> TYPE: DNA  
<213> ORGANISM: Artificial Sequence  
<220> FEATURE:  
<223> OTHER INFORMATION: synthetic

<400> SEQUENCE: 13

```
gccactgtgc tggattcact tcagttgcac caacaccatg aa                        42
```

<210> SEQ ID NO 14  
<211> LENGTH: 477  
<212> TYPE: PRT  
<213> ORGANISM: Apis mellifera

<400> SEQUENCE: 14

```
Met Lys Phe Lys Gln Gln Gly Leu Ile Ala Asp Leu Met Pro Asn Ile
1               5                   10                  15

Asn Leu Met Lys Ala Thr Gly His Phe Met Phe Asn Tyr Tyr Thr Asp
            20                  25                  30

Ser Ser Thr Lys His Ile His Lys Ile Tyr Cys Ile Val His Leu Val
            35                  40                  45

Leu Ile Leu Met Gln Phe Gly Phe Cys Gly Ile Asn Leu Met Met Glu
        50                  55                  60

Ser Glu Asp Val Asp Asp Leu Thr Ala Asn Thr Ile Thr Met Leu Phe
65                  70                  75                  80

Phe Thr His Ser Val Val Lys Leu Val Tyr Phe Ala Val Arg Ser Lys
                85                  90                  95

Leu Phe Tyr Arg Thr Leu Gly Ile Trp Asn Asn Pro Asn Ser His Pro
            100                 105                 110

Leu Phe Ala Glu Ser Asn Ala Arg Tyr His Gln Ile Ala Val Lys Lys
            115                 120                 125

Met Arg Ile Leu Leu Ala Val Ile Gly Thr Thr Val Leu Ser Ala
            130                 135                 140

Ile Ser Trp Thr Thr Ile Thr Phe Ile Gly Asp Ser Val Lys Lys Val
145                 150                 155                 160

Ile Asp Pro Val Thr Asn Glu Thr Thr Tyr Val Glu Ile Pro Arg Leu
                165                 170                 175

Met Val Arg Ser Trp Tyr Pro Tyr Asp Pro Ser His Gly Met Ala His
            180                 185                 190

Ile Leu Thr Leu Ile Phe Gln Phe Tyr Trp Leu Ile Phe Cys Met Ala
            195                 200                 205

Asp Ala Asn Leu Leu Asp Val Leu Phe Cys Ser Trp Leu Leu Phe Ala
210                 215                 220

Cys Glu Gln Ile Gln His Leu Lys Asn Ile Met Lys Pro Leu Met Glu
225                 230                 235                 240

Phe Ser Ala Thr Leu Asp Thr Val Val Pro Asn Ser Gly Glu Leu Phe
            245                 250                 255

Lys Ala Gly Ser Ala Glu Gln Pro Lys Glu Gln Glu Pro Leu Pro Pro
            260                 265                 270

Val Thr Pro Pro Gln Gly Glu Asn Met Leu Asp Met Asp Leu Arg Gly
        275                 280                 285

Ile Tyr Ser Asn Arg Thr Asp Phe Thr Thr Thr Phe Arg Pro Thr Ala
        290                 295                 300

Gly Met Thr Phe Asn Gly Gly Val Gly Pro Asn Gly Leu Thr Lys Lys
305                 310                 315                 320

Gln Glu Met Leu Val Arg Ser Ala Ile Lys Tyr Trp Val Glu Arg His
                325                 330                 335

Lys His Ile Val Arg Leu Val Thr Ala Ile Gly Asp Ala Tyr Gly Val
            340                 345                 350

Ala Leu Leu Leu His Met Leu Thr Thr Ile Thr Leu Thr Leu Leu
            355                 360                 365

Ala Tyr Gln Ala Thr Lys Ile His Ala Val Asp Thr Tyr Ala Ala Ser
        370                 375                 380

Val Val Gly Tyr Leu Leu Tyr Ser Leu Gly Gln Val Phe Met Leu Cys
385                 390                 395                 400

Ile Phe Gly Asn Arg Leu Ile Glu Glu Ser Ser Val Met Glu Ala
            405                 410                 415

Ala Tyr Ser Cys His Trp Tyr Asp Gly Ser Glu Glu Ala Lys Thr Phe
```

|   | 420 |   | 425 |   | 430 |

Val Gln Ile Val Cys Gln Gln Cys Gln Lys Ala Met Ser Ile Ser Gly
      435                 440                 445

Ala Lys Phe Phe Thr Val Ser Leu Asp Leu Phe Ala Ser Val Leu Gly
  450                 455                 460

Ala Met Val Thr Tyr Phe Met Val Leu Val Gln Leu Lys
465                 470                 475

<210> SEQ ID NO 15
<211> LENGTH: 36
<212> TYPE: DNA
<213> ORGANISM: Artificial Sequence
<220> FEATURE:
<223> OTHER INFORMATION: synthetic

<400> SEQUENCE: 15
caccatgcaa gtccagccga ccaagtacgt cggcct                          36

<210> SEQ ID NO 16
<211> LENGTH: 29
<212> TYPE: DNA
<213> ORGANISM: Artificial Sequence
<220> FEATURE:
<223> OTHER INFORMATION: synthetic

<400> SEQUENCE: 16
ttacttcagc tgcaccagca ccatgaagt                                  29

<210> SEQ ID NO 17
<211> LENGTH: 1437
<212> TYPE: DNA
<213> ORGANISM: Anopheles gambiae

<400> SEQUENCE: 17
atgcaagtcc agccgaccaa gtacgtcggc ctcgtcgccg acctgatgcc gaacattcgg      60
ctgatgcagg ccagcggtca ctttctgttc cgctacgtca ccggcccgat actgatccgc     120
aaggtgtact cctggtggac gctcgccatg gtgctgatcc agttcttcgc catcctcggc     180
aacctggcga cgaacgcgga cgacgtgaac gagctgaccg ccaacacgat cacgaccctg     240
ttcttcacgc actcggtcac caagttcatc tactttgcgg tcaactcgga gaacttctac     300
cggacgctcg ccatctggaa ccagaccaac acgcaccccgc tgtttgccga atcggacgcc     360
cggtaccatt cgattgcgct cgccaagatg cggaagctgc tggtgctggt gatggccacc     420
accgtcctgt cggttgtcgc ctgggttacg ataacatttt cggcgagag cgtcaagacc     480
gtgctcgata aggcaaccaa cgagacgtac acggtggata taccccggct gcccatcaag     540
tcctggtatc cgtggaatgc aatgagcgga ccggcgtaca ttttctcttt catctaccag     600
atttacttcc tgctgttttc gatggtccag agcaacctcg cggatgtcat gttctgctcc     660
tggttgctgc tagcctgcga gcagctgcaa cacttgaagg gtattatgcg atcgctgatg     720
gagctttcgg cctcgctgga cacctaccgg cccaactctt cgcaactgtt ccgagcaatt     780
tcagccggtt ccaaatcgga gctgatcatc aacgaagaaa aggatccgga cgttaaggac     840
tttgatctga gcggcatcta cagctcgaag gcggactggg cgcccagtt ccgtgcgccg     900
tcgacgctgc aaacgttcga cgagaatggc aggaacggaa atccgaacgg gcttacccgg     960
aagcaggaaa tgatggtgcg cagcgccatc aagtactggg tcgagcggca caagcacgtt    1020
gtacgtctcg tttcagcaat cggagatacg tacggtcctg ccctgctgct acacatgctg    1080

```
acctccacca tcaagctgac gctgctcgcc taccaggcaa cgaaaatcga cggtgtcaac    1140
gtgtacggat tgaccgtaat cggatatttg tgctacgcgt tggctcaggt tttcctgttt    1200
tgcatctttg gcaatcggct catcgaggag agctcatccg tgatggaggc ggcctattcc    1260
tgccactggt acgacgggtc cgaggaggca aaaaccttcg tccagatcgt ttgtcagcag    1320
tgccagaagg cgatgactat ttccggagca agttttcca ccgtttcgct cgatctgttt    1380
gcttcggttc ttggagccgt tgtcacctac ttcatggtgc tggtgcagct gaagtaa      1437

<210> SEQ ID NO 18
<211> LENGTH: 478
<212> TYPE: PRT
<213> ORGANISM: Anopheles gambiae

<400> SEQUENCE: 18

Met Gln Val Gln Pro Thr Lys Tyr Val Gly Leu Val Ala Asp Leu Met
1               5                   10                  15

Pro Asn Ile Arg Leu Met Gln Ala Ser Gly His Phe Leu Phe Arg Tyr
                20                  25                  30

Val Thr Gly Pro Ile Leu Ile Arg Lys Val Tyr Ser Trp Trp Thr Leu
            35                  40                  45

Ala Met Val Leu Ile Gln Phe Phe Ala Ile Leu Gly Asn Leu Ala Thr
        50                  55                  60

Asn Ala Asp Asp Val Asn Glu Leu Thr Ala Asn Thr Ile Thr Thr Leu
65                  70                  75                  80

Phe Phe Thr His Ser Val Thr Lys Phe Ile Tyr Phe Ala Val Asn Ser
                85                  90                  95

Glu Asn Phe Tyr Arg Thr Leu Ala Ile Trp Asn Gln Thr Asn Thr His
                100                 105                 110

Pro Leu Phe Ala Glu Ser Asp Ala Arg Tyr His Ser Ile Ala Leu Ala
            115                 120                 125

Lys Met Arg Lys Leu Leu Val Leu Val Met Ala Thr Thr Val Leu Ser
        130                 135                 140

Val Val Ala Trp Val Thr Ile Thr Phe Phe Gly Glu Ser Val Lys Thr
145                 150                 155                 160

Val Leu Asp Lys Ala Thr Asn Glu Thr Tyr Thr Val Asp Ile Pro Arg
                165                 170                 175

Leu Pro Ile Lys Ser Trp Tyr Pro Trp Asn Ala Met Ser Gly Pro Ala
            180                 185                 190

Tyr Ile Phe Ser Phe Ile Tyr Gln Ile Tyr Phe Leu Leu Phe Ser Met
        195                 200                 205

Val Gln Ser Asn Leu Ala Asp Val Met Phe Cys Ser Trp Leu Leu Leu
    210                 215                 220

Ala Cys Glu Gln Leu Gln His Leu Lys Gly Ile Met Arg Ser Leu Met
225                 230                 235                 240

Glu Leu Ser Ala Ser Leu Asp Thr Tyr Arg Pro Asn Ser Ser Gln Leu
                245                 250                 255

Phe Arg Ala Ile Ser Ala Gly Ser Lys Ser Glu Leu Ile Ile Asn Glu
            260                 265                 270

Glu Lys Asp Pro Asp Val Lys Asp Phe Asp Leu Ser Gly Ile Tyr Ser
        275                 280                 285

Ser Lys Ala Asp Trp Gly Ala Gln Phe Arg Ala Pro Ser Thr Leu Gln
    290                 295                 300

Thr Phe Asp Glu Asn Gly Arg Asn Gly Asn Pro Asn Gly Leu Thr Arg
305                 310                 315                 320
```

Lys Gln Glu Met Met Val Arg Ser Ala Ile Lys Tyr Trp Val Glu Arg
            325                 330                 335

His Lys His Val Val Arg Leu Val Ser Ala Ile Gly Asp Thr Tyr Gly
        340                 345                 350

Pro Ala Leu Leu Leu His Met Leu Thr Ser Thr Ile Lys Leu Thr Leu
    355                 360                 365

Leu Ala Tyr Gln Ala Thr Lys Ile Asp Gly Val Asn Val Tyr Gly Leu
370                 375                 380

Thr Val Ile Gly Tyr Leu Cys Tyr Ala Leu Ala Gln Val Phe Leu Phe
385                 390                 395                 400

Cys Ile Phe Gly Asn Arg Leu Ile Glu Glu Ser Ser Val Met Glu
                405                 410                 415

Ala Ala Tyr Ser Cys His Trp Tyr Asp Gly Ser Glu Glu Ala Lys Thr
                420                 425                 430

Phe Val Gln Ile Val Cys Gln Gln Cys Gln Lys Ala Met Thr Ile Ser
            435                 440                 445

Gly Ala Lys Phe Phe Thr Val Ser Leu Asp Leu Phe Ala Ser Val Leu
        450                 455                 460

Gly Ala Val Val Thr Tyr Phe Met Val Leu Val Gln Leu Lys
465                 470                 475

```
<210> SEQ ID NO 19
<211> LENGTH: 45
<212> TYPE: DNA
<213> ORGANISM: Artificial Sequence
<220> FEATURE:
<223> OTHER INFORMATION: synthetic

<400> SEQUENCE: 19
tggaattctg cagatcacca tgacaacctc gatgcagccg agcaa            45

<210> SEQ ID NO 20
<211> LENGTH: 26
<212> TYPE: DNA
<213> ORGANISM: Artificial Sequence
<220> FEATURE:
<223> OTHER INFORMATION: synthetic

<400> SEQUENCE: 20
cgtgttgccc gacagctcgt tgacct                                 26

<210> SEQ ID NO 21
<211> LENGTH: 45
<212> TYPE: DNA
<213> ORGANISM: Artificial Sequence
<220> FEATURE:
<223> OTHER INFORMATION: synthetic

<400> SEQUENCE: 21
tggaattctg cagatcacca tgacaacctc gatgcagccg agcaa            45

<210> SEQ ID NO 22
<211> LENGTH: 27
<212> TYPE: DNA
<213> ORGANISM: Artificial Sequence
<220> FEATURE:
<223> OTHER INFORMATION: synthetic

<400> SEQUENCE: 22
aaagaaggtg atcgtggtcc aggcggt                                27
```

<210> SEQ ID NO 23
<211> LENGTH: 45
<212> TYPE: DNA
<213> ORGANISM: Artificial Sequence
<220> FEATURE:
<223> OTHER INFORMATION: synthetic

<400> SEQUENCE: 23
tggaattctg cagatcacca tgacaacctc gatgcagccg agcaa         45

<210> SEQ ID NO 24
<211> LENGTH: 30
<212> TYPE: DNA
<213> ORGANISM: Artificial Sequence
<220> FEATURE:
<223> OTHER INFORMATION: synthetic

<400> SEQUENCE: 24
caagtgctgc agctgctcgc aggcgaatat         30

<210> SEQ ID NO 25
<211> LENGTH: 45
<212> TYPE: DNA
<213> ORGANISM: Artificial Sequence
<220> FEATURE:
<223> OTHER INFORMATION: synthetic

<400> SEQUENCE: 25
tggaattctg cagatcacca tgacaacctc gatgcagccg agcaa         45

<210> SEQ ID NO 26
<211> LENGTH: 30
<212> TYPE: DNA
<213> ORGANISM: Artificial Sequence
<220> FEATURE:
<223> OTHER INFORMATION: synthetic

<400> SEQUENCE: 26
ggcctggtat gccagcaggg tcagcttgat         30

<210> SEQ ID NO 27
<211> LENGTH: 45
<212> TYPE: DNA
<213> ORGANISM: Artificial Sequence
<220> FEATURE:
<223> OTHER INFORMATION: synthetic

<400> SEQUENCE: 27
tggaattctg cagatcacca tgacaacctc gatgcagccg agcaa         45

<210> SEQ ID NO 28
<211> LENGTH: 26
<212> TYPE: DNA
<213> ORGANISM: Artificial Sequence
<220> FEATURE:
<223> OTHER INFORMATION: synthetic

<400> SEQUENCE: 28
attgccaaag atgcaaaagt ggaaca         26

<210> SEQ ID NO 29
<211> LENGTH: 45
<212> TYPE: DNA
<213> ORGANISM: Artificial Sequence
<220> FEATURE:
<223> OTHER INFORMATION: synthetic

<400> SEQUENCE: 29
tggaattctg cagatcacca tgacaacctc gatgcagccg agcaa                45

<210> SEQ ID NO 30
<211> LENGTH: 33
<212> TYPE: DNA
<213> ORGANISM: Artificial Sequence
<220> FEATURE:
<223> OTHER INFORMATION: synthetic

<400> SEQUENCE: 30
ggccgacagg gacctgaaga gggccgccga gtt                             33

<210> SEQ ID NO 31
<211> LENGTH: 45
<212> TYPE: DNA
<213> ORGANISM: Artificial Sequence
<220> FEATURE:
<223> OTHER INFORMATION: synthetic

<400> SEQUENCE: 31
tggaattctg cagatcacca tgacaacctc gatgcagccg agcaa                45

<210> SEQ ID NO 32
<211> LENGTH: 25
<212> TYPE: DNA
<213> ORGANISM: Artificial Sequence
<220> FEATURE:
<223> OTHER INFORMATION: synthetic

<400> SEQUENCE: 32
atccgctttc gagctgtaga tgccc                                      25

<210> SEQ ID NO 33
<211> LENGTH: 45
<212> TYPE: DNA
<213> ORGANISM: Artificial Sequence
<220> FEATURE:
<223> OTHER INFORMATION: synthetic

<400> SEQUENCE: 33
tggaattctg cagatcacca tgacaacctc gatgcagccg agcaa                45

<210> SEQ ID NO 34
<211> LENGTH: 27
<212> TYPE: DNA
<213> ORGANISM: Artificial Sequence
<220> FEATURE:
<223> OTHER INFORMATION: synthetic

<400> SEQUENCE: 34
gggattagcg ccgttcacca acccgtt                                    27

<210> SEQ ID NO 35
<211> LENGTH: 45
<212> TYPE: DNA
<213> ORGANISM: Artificial Sequence
<220> FEATURE:
<223> OTHER INFORMATION: synthetic

<400> SEQUENCE: 35
tggaattctg cagatcacca tgacaacctc gatgcagccg agcaa                45

<210> SEQ ID NO 36

```
<210> SEQ ID NO 36
<211> LENGTH: 26
<212> TYPE: DNA
<213> ORGANISM: Artificial Sequence
<220> FEATURE:
<223> OTHER INFORMATION: synthetic

<400> SEQUENCE: 36
tccgtaagta tcgccgatgg cagcca                                          26

<210> SEQ ID NO 37
<211> LENGTH: 45
<212> TYPE: DNA
<213> ORGANISM: Artificial Sequence
<220> FEATURE:
<223> OTHER INFORMATION: synthetic

<400> SEQUENCE: 37
tggaattctg cagatcacca tgacaacctc gatgcagccg agcaa                     45

<210> SEQ ID NO 38
<211> LENGTH: 26
<212> TYPE: DNA
<213> ORGANISM: Artificial Sequence
<220> FEATURE:
<223> OTHER INFORMATION: synthetic

<400> SEQUENCE: 38
gtggatcatc gagaagagca cgtagt                                          26

<210> SEQ ID NO 39
<211> LENGTH: 40
<212> TYPE: DNA
<213> ORGANISM: Artificial Sequence
<220> FEATURE:
<223> OTHER INFORMATION: synthetic

<400> SEQUENCE: 39
ctgtcgggca acacgataac gacgctgttt ttcacccatt                           40

<210> SEQ ID NO 40
<211> LENGTH: 42
<212> TYPE: DNA
<213> ORGANISM: Artificial Sequence
<220> FEATURE:
<223> OTHER INFORMATION: synthetic

<400> SEQUENCE: 40
gccactgtgc tggatttatt tcaactgcac caacaccatg aa                        42

<210> SEQ ID NO 41
<211> LENGTH: 40
<212> TYPE: DNA
<213> ORGANISM: Artificial Sequence
<220> FEATURE:
<223> OTHER INFORMATION: synthetic

<400> SEQUENCE: 41
acgatcacct tctttggcga tagcgtcaaa aacgtattcg                           40

<210> SEQ ID NO 42
<211> LENGTH: 35
<212> TYPE: DNA
<213> ORGANISM: Artificial Sequence
<220> FEATURE:
<223> OTHER INFORMATION: synthetic

<400> SEQUENCE: 42
```

```
gccactgtgc tggatttatt tcaactgcac caaca                             35

<210> SEQ ID NO 43
<211> LENGTH: 42
<212> TYPE: DNA
<213> ORGANISM: Artificial Sequence
<220> FEATURE:
<223> OTHER INFORMATION: synthetic

<400> SEQUENCE: 43
cagctgcagc acttgaaggg tataatgcgc ccctgatgg aa                      42

<210> SEQ ID NO 44
<211> LENGTH: 35
<212> TYPE: DNA
<213> ORGANISM: Artificial Sequence
<220> FEATURE:
<223> OTHER INFORMATION: synthetic

<400> SEQUENCE: 44
gccactgtgc tggatttatt tcaactgcac caaca                             35

<210> SEQ ID NO 45
<211> LENGTH: 39
<212> TYPE: DNA
<213> ORGANISM: Artificial Sequence
<220> FEATURE:
<223> OTHER INFORMATION: synthetic

<400> SEQUENCE: 45
ctggcatacc aggccaccaa aatcgatgca ctcaacgtt                         39

<210> SEQ ID NO 46
<211> LENGTH: 35
<212> TYPE: DNA
<213> ORGANISM: Artificial Sequence
<220> FEATURE:
<223> OTHER INFORMATION: synthetic

<400> SEQUENCE: 46
gccactgtgc tggatttatt tcaactgcac caaca                             35

<210> SEQ ID NO 47
<211> LENGTH: 40
<212> TYPE: DNA
<213> ORGANISM: Artificial Sequence
<220> FEATURE:
<223> OTHER INFORMATION: synthetic

<400> SEQUENCE: 47
tgcatctttg gcaatcgatt aattgaagag agttcatcag                        40

<210> SEQ ID NO 48
<211> LENGTH: 35
<212> TYPE: DNA
<213> ORGANISM: Artificial Sequence
<220> FEATURE:
<223> OTHER INFORMATION: synthetic

<400> SEQUENCE: 48
gccactgtgc tggatttatt tcaactgcac caaca                             35

<210> SEQ ID NO 49
<211> LENGTH: 42
<212> TYPE: DNA
```

```
<213> ORGANISM: Artificial Sequence
<220> FEATURE:
<223> OTHER INFORMATION: synthetic

<400> SEQUENCE: 49
aggtccctgt cggccggatc caaatcggag ctgattttga at                          42

<210> SEQ ID NO 50
<211> LENGTH: 42
<212> TYPE: DNA
<213> ORGANISM: Artificial Sequence
<220> FEATURE:
<223> OTHER INFORMATION: synthetic

<400> SEQUENCE: 50
gccactgtgc tggatttatt tcaactgcac caacaccatg aa                          42

<210> SEQ ID NO 51
<211> LENGTH: 40
<212> TYPE: DNA
<213> ORGANISM: Artificial Sequence
<220> FEATURE:
<223> OTHER INFORMATION: synthetic

<400> SEQUENCE: 51
agctcgaaag cggattgggg tgcccagttc agggcgccat                             40

<210> SEQ ID NO 52
<211> LENGTH: 42
<212> TYPE: DNA
<213> ORGANISM: Artificial Sequence
<220> FEATURE:
<223> OTHER INFORMATION: synthetic

<400> SEQUENCE: 52
gccactgtgc tggatttatt tcaactgcac caacaccatg aa                          42

<210> SEQ ID NO 53
<211> LENGTH: 41
<212> TYPE: DNA
<213> ORGANISM: Artificial Sequence
<220> FEATURE:
<223> OTHER INFORMATION: synthetic

<400> SEQUENCE: 53
aacggcgcta atcccaatgg actaaccaag aagcaggaac t                           41

<210> SEQ ID NO 54
<211> LENGTH: 42
<212> TYPE: DNA
<213> ORGANISM: Artificial Sequence
<220> FEATURE:
<223> OTHER INFORMATION: synthetic

<400> SEQUENCE: 54
gccactgtgc tggatttatt tcaactgcac caacaccatg aa                          42

<210> SEQ ID NO 55
<211> LENGTH: 40
<212> TYPE: DNA
<213> ORGANISM: Artificial Sequence
<220> FEATURE:
<223> OTHER INFORMATION: synthetic

<400> SEQUENCE: 55
ggcgatactt acggagccgc cctgttgctt cacatgttga                             40
```

<210> SEQ ID NO 56
<211> LENGTH: 42
<212> TYPE: DNA
<213> ORGANISM: Artificial Sequence
<220> FEATURE:
<223> OTHER INFORMATION: synthetic

<400> SEQUENCE: 56
gccactgtgc tggatttatt tcaactgcac caacaccatg aa         42

<210> SEQ ID NO 57
<211> LENGTH: 40
<212> TYPE: DNA
<213> ORGANISM: Artificial Sequence
<220> FEATURE:
<223> OTHER INFORMATION: synthetic

<400> SEQUENCE: 57
ttctcgatga tccacgccaa cctcgccgat gtgatgtttt           40

<210> SEQ ID NO 58
<211> LENGTH: 42
<212> TYPE: DNA
<213> ORGANISM: Artificial Sequence
<220> FEATURE:
<223> OTHER INFORMATION: synthetic

<400> SEQUENCE: 58
gccactgtgc tggatttatt tcaactgcac caacaccatg aa         42

<210> SEQ ID NO 59
<211> LENGTH: 1443
<212> TYPE: DNA
<213> ORGANISM: Artificial Sequence
<220> FEATURE:
<223> OTHER INFORMATION: synthetic

<400> SEQUENCE: 59
atgacaacct cgatgcagcc gagcaagtac acgggcctgg tcgccgacct gatgcccaac    60
atccgggcga tgaagtactc cggcctgttc atgcacaact tcacgggcgg cagtgccttc    120
atgaagaagg tgtactcctc cgtgcacctg gtgttcctcc tcatgcagtt caccttcatc    180
ctggtcaaca tggccctgaa cgccgaggag gtcaacgagc tgtcgggcaa cacgataacg    240
acgctgtttt tcacccattc tgtgaccaag ttcatctacg tcgccgtcaa ctcggaacat    300
ttctaccgca cgctgggcat ctggaatcaa ccgaacagtc attcactttt tgccgaatcg    360
gatgctcggt accattcgat tgcgttggct aagatgcgaa aactgctggt catggtgatg    420
gtgactacag tgctatccgt cgtcgcatgg atcacgataa cattcttcgg cgatagcgtc    480
aaaaacgtat tcgacaaaga gactaacgaa acgtatacgg tggaaattcc ccgattgccc    540
atcaaggctt ggtacccgtg ggatgcaatg agccggagtgc cgtacttttt ctccttcatc    600
taccaggctt atttcctact gttttcgatg tgccaggcca acctcgccga tgtgatgttt    660
tgctcctggc tgcttttcac ttgcgaacag ctgcaacatt tgaagggtat aatgcgcccc    720
ctgatggaac tttccgccac gctggacacc taccgaccaa actcggctgc cctgttccgt    780
gtcgcttccg ccggatccaa atcggagctg attttgaatg aagagaaaga tcccgacacg    840
aaagatttcg acttgaacgg tatctacaac tcgaaagcgg actggggtgc ccagttcagg    900
gcgccatcca ctttgcaaac gttcggtgac aatggcatca atggtaatcc aaatggacta    960

| | |
|---|---:|
| accaagaagc aggaactgat ggtccgaagt gcgatcaagt actgggtgga gaggcacaag | 1020 |
| cacgtcgttc gcctcgtatc ggccatcggt gaaacttacg gagccgccct gttgcttcac | 1080 |
| atgttgacct cgaccatcaa gctgaccctg ttggcttacc aggcaaccaa aatcgatgca | 1140 |
| ctcaacgttt atggactgac cgtgatcggc tatctggtct atgctctggc tcaggtgttc | 1200 |
| ctgttttgca ttttcggcaa tcgattaatt gaagagagtt catcagtgat ggaggctgcc | 1260 |
| tactcgtgcc actggtatga cggttccgag gaagccaaaa ctttcgtgca aatcgtttgc | 1320 |
| cagcagtgtc agaaagcgat gaccatatcc ggggccaagt ttttcaccgt ttcactggat | 1380 |
| ctgttcgcat cggttctggg agcggtcgtc acctacttca tggtgttggt gcagttgaaa | 1440 |
| taa | 1443 |

<210> SEQ ID NO 60
<211> LENGTH: 1443
<212> TYPE: DNA
<213> ORGANISM: Artificial Sequence
<220> FEATURE:
<223> OTHER INFORMATION: synthetic

<400> SEQUENCE: 60

| | |
|---|---:|
| atgacaacct cgatgcagcc gagcaagtac acgggcctgg tcgccgacct gatgcccaac | 60 |
| atccgggcga tgaagtactc cggcctgttc atgcacaact tcacgggcgg cagtgccttc | 120 |
| atgaagaagg tgtactcctc cgtgcacctg gtgttcctcc tcatgcagtt caccttcatc | 180 |
| ctggtcaaca tggccctgaa cgccgaggag gtcaacgagc tgtcgggcaa cacgatcacg | 240 |
| accctcttct tcacccactg catcacgaag tttatctacc tggctgttaa ccagaagaat | 300 |
| ttctacagaa cattgaatat atggaaccag gtgaacacgc atcccttgtt cgccgagtcg | 360 |
| gatgctcgtt accattcgat cgcactggcg aagatgagga agctgttctt tctggtgatg | 420 |
| ctgaccacag tcgcctcggc caccgcctgg accacgatca ccttctttgg cgatagcgtc | 480 |
| aaaaacgtat tcgacaaaga gactaacgaa acgtatacgg tggaaattcc ccgattgccc | 540 |
| atcaaggctt ggtacccgtg ggatgcaatg agcggagtgc cgtactttt ctccttcatc | 600 |
| taccaggctt atttcctact gttttcgatg tgccaggcca acctcgccga tgtgatgttt | 660 |
| tgctcctggc tgcttttcac ttgcgaacag ctgcaacatt tgaagggtat aatgcgcccc | 720 |
| ctgatggaac tttccgccac gctggacacc taccgaccaa actcggctgc cctgttccgt | 780 |
| gtcgcttccg ccggatccaa atcggagctg atttgaatg aagagaaaga tcccgacacg | 840 |
| aaagatttcg acttgaacgg tatctacaac tcgaaagcgg actggggtgc ccagttcagg | 900 |
| gcgccatcca ctttgcaaac gttcggtgac aatggcatca tggtaatcc aaatggacta | 960 |
| accaagaagc aggaactgat ggtccgaagt gcgatcaagt actgggtgga gaggcacaag | 1020 |
| cacgtcgttc gcctcgtatc ggccatcggt gaaacttacg gagccgccct gttgcttcac | 1080 |
| atgttgacct cgaccatcaa gctgaccctg ttggcttacc aggcaaccaa aatcgatgca | 1140 |
| ctcaacgttt atggactgac cgtgatcggc tatctggtct atgctctggc tcaggtgttc | 1200 |
| ctgttttgca ttttcggcaa tcgattaatt gaagagagtt catcagtgat ggaggctgcc | 1260 |
| tactcgtgcc actggtatga cggttccgag gaagccaaaa ctttcgtgca aatcgtttgc | 1320 |
| cagcagtgtc agaaagcgat gaccatatcc ggggccaagt ttttcaccgt ttcactggat | 1380 |
| ctgttcgcat cggttctggg agcggtcgtc acctacttca tggtgttggt gcagttgaaa | 1440 |
| taa | 1443 |

<210> SEQ ID NO 61
<211> LENGTH: 1443
<212> TYPE: DNA
<213> ORGANISM: Artificial Sequence
<220> FEATURE:
<223> OTHER INFORMATION: syhthetic

<400> SEQUENCE: 61

| | |
|---|---|
| atgacaacct cgatgcagcc gagcaagtac acgggcctgg tcgccgacct gatgcccaac | 60 |
| atccgggcga tgaagtactc cggcctgttc atgcacaact tcacgggcgg cagtgccttc | 120 |
| atgaagaagg tgtactcctc cgtgcacctg gtgttcctcc tcatgcagtt caccttcatc | 180 |
| ctggtcaaca tggccctgaa cgccgaggag gtcaacgagc tgtcgggcaa cacgatcacg | 240 |
| accctcttct tcacccactg catcacgaag tttatctacc tggctgttaa ccagaagaat | 300 |
| ttctacagaa cattgaatat atggaaccag gtgaacacgc atcccttgtt cgccgagtcg | 360 |
| gatgctcgtt accattcgat cgcactggcg aagatgagga agctgttctt tctggtgatg | 420 |
| ctgaccacag tcgcctcggc caccgcctgg accacgatca ccttctttgg cgacagcgta | 480 |
| aaaatggtgg tggaccatga cgaactcc agcatcccgg tggagatacc ccggctgccg | 540 |
| attaagtcct ctacccgtg gaacgccagc cacggcatgt tctacatgat cagctttgcc | 600 |
| tttcagatct actacgtgct cttctcgatg atccactcca atctatgcga cgtgatgttc | 660 |
| tgctcttggc tgatattcgc ctgcgagcag ctgcagcact tgaagggtat aatgcgcccc | 720 |
| ctgatggaac tttccgccac gctggacacc taccgaccaa actcggctgc cctgttccgt | 780 |
| gtcgcttccg ccggatccaa atcggagctg attttgaatg aagagaaaga tcccgacacg | 840 |
| aaagatttcg acttgaacgg tatctacaac tcgaaagcgg actggggtgc ccagttcagg | 900 |
| gcgccatcca ctttgcaaac gttcggtgac aatggcatca atggtaatcc aaatggacta | 960 |
| accaagaagc aggaactgat ggtccgaagt gcgatcaagt actgggtgga gaggcacaag | 1020 |
| cacgtcgttc gcctcgtatc ggccatcggt gaaacttacg gagccgccct gttgcttcac | 1080 |
| atgttgacct cgaccatcaa gctgaccctg ttggcttacc aggcaaccaa atcgatgca | 1140 |
| ctcaacgttt atggactgac cgtgatcggc tatctggtct atgctctggc tcaggtgttc | 1200 |
| ctgttttgca ttttcggcaa tcgattaatt gaagagagtt catcagtgat ggaggctgcc | 1260 |
| tactcgtgcc actggtatga cggttccgag gaagccaaaa ctttcgtgca aatcgtttgc | 1320 |
| cagcagtgtc agaaagcgat gaccatatcc ggggccaagt ttttcaccgt ttcactggat | 1380 |
| ctgttcgcat cggttctggg agcggtcgtc acctacttca tggtgttggt gcagttgaaa | 1440 |
| taa | 1443 |

<210> SEQ ID NO 62
<211> LENGTH: 1461
<212> TYPE: DNA
<213> ORGANISM: Artificial Sequence
<220> FEATURE:
<223> OTHER INFORMATION: synthetic

<400> SEQUENCE: 62

| | |
|---|---|
| atgacaacct cgatgcagcc gagcaagtac acgggcctgg tcgccgacct gatgcccaac | 60 |
| atccgggcga tgaagtactc cggcctgttc atgcacaact tcacgggcgg cagtgccttc | 120 |
| atgaagaagg tgtactcctc cgtgcacctg gtgttcctcc tcatgcagtt caccttcatc | 180 |
| ctggtcaaca tggccctgaa cgccgaggag gtcaacgagc tgtcgggcaa cacgatcacg | 240 |
| accctcttct tcacccactg catcacgaag tttatctacc tggctgttaa ccagaagaat | 300 |

-continued

```
ttctacagaa cattgaatat atggaaccag gtgaacacgc atcccttgtt cgccgagtcg      360
gatgctcgtt accattcgat cgcactggcg aagatgagga agctgttctt tctggtgatg      420
ctgaccacag tcgcctcggc caccgcctgg accacgatca ccttctttgg cgacagcgta      480
aaaatggtgg tggaccatga gacgaactcc agcatcccgg tggagatacc ccggctgccg      540
attaagtcct tctacccgtg gaacgccagc cacggcatgt tctacatgat cagctttgcc      600
tttcagatct actacgtgct cttctcgatg atccactcca atctatgcga cgtgatgttc      660
tgctcttggc tgatattcgc ctgcgagcag ctgcagcact gaagggcat catgaagccg       720 ctgatggagc tgtccgcctc gctggacacc tacaggccca actcggcggc cctcttcagg      780
tccctgtcgg ccaactccaa gtcggagcta attcataatg aagaaaagga tcccggcacc      840
gacatggaca tgtcgggcat ctacagctcg aaagcggatt ggggcgctca gtttcgagca      900
ccctcgacac tgcagtcctt tggcgggaac ggggcggag gcaacgggtt ggtgaacggc       960
gctaatccca acgggctgac caaaaagcag gagatgatgg tgcgcagtgc catcaagtac     1020
tgggtcgagc ggcacaagca cgtggtgcga ctggtggctg ccatcggcga tacttacgga     1080
gccgccctcc tcctccacat gctgacctcg accatcaagc tgaccctgct ggcataccag     1140
gccaccaaaa tcgatgcact caacgtttat ggactgaccg tgatcggcta tctggtctat     1200
gctctggctc agtgttcct gttttgcatt ttcggcaatc gattaattga agagagttca     1260
tcagtgatga aggctgccta tcgtgccac tggtatgacg gttccgagga agccaaaact     1320
ttcgtgcaaa tcgtttgcca gcagtgtcag aaagcgatga ccatatccgg ggccaagttt     1380
ttcaccgttt cactggatct gttcgcatcg gttctgggag cggtcgtcac ctacttcatg     1440
gtgttggtgc agttgaaata a                                              1461
```

<210> SEQ ID NO 63
<211> LENGTH: 1461
<212> TYPE: DNA
<213> ORGANISM: Artificial Sequence
<220> FEATURE:
<223> OTHER INFORMATION: synthetic

<400> SEQUENCE: 63

```
atgacaacct cgatgcagcc gagcaagtac acgggcctgg tcgccgacct gatgcccaac       60
atccgggcga tgaagtactc cggcctgttc atgcacaact tcacgggcgg cagtgccttc      120
atgaagaagg tgtactcctc cgtgcacctg gtgttcctcc tcatgcagtt caccttcatc      180
ctggtcaaca tggccctgaa cgccgaggag gtcaacgagc tgtcgggcaa cacgatcacg      240
accctcttct tcacccactg catcacgaag tttatctacc tggctgttaa ccagaagaat      300
ttctacagaa cattgaatat atggaaccag gtgaacacgc atcccttgtt cgccgagtcg      360
gatgctcgtt accattcgat cgcactggcg aagatgagga agctgttctt tctggtgatg      420
ctgaccacag tcgcctcggc caccgcctgg accacgatca ccttctttgg cgacagcgta      480
aaaatggtgg tggaccatga gacgaactcc agcatcccgg tggagatacc ccggctgccg      540
attaagtcct tctacccgtg gaacgccagc cacggcatgt tctacatgat cagctttgcc      600
tttcagatct actacgtgct cttctcgatg atccactcca atctatgcga cgtgatgttc      660
tgctcttggc tgatattcgc ctgcgagcag ctgcagcact gaagggcat catgaagccg       720 ctgatggagc tgtccgcctc gctggacacc tacaggccca actcggcggc cctcttcagg      780
tccctgtcgg ccaactccaa gtcggagcta attcataatg aagaaaagga tcccggcacc      840
gacatggaca tgtcgggcat ctacagctcg aaagcggatt ggggcgctca gtttcgagca      900
```

```
ccctcgacac tgcagtcctt tggcgggaac gggggcggag gcaacgggtt ggtgaacggc      960
gctaatccca acgggctgac caaaaagcag gagatgatgg tgcgcagtgc catcaagtac     1020
tgggtcgagc ggcacaagca cgtggtgcga ctggtggctg ccatcggcga tacttacgga     1080
gccgccctcc tcctccacat gctgacctcg accatcaagc tgaccctgct ggcataccag     1140
gccaccaaaa tcaacggagt gaatgtctac gccttcacag tcgtcggata cctaggatac     1200
gcgctggccc aggtgttcca cttttgcatc tttggcaatc gattaattga agagagttca     1260
tcagtgatgg aggctgccta ctcgtgccac tggtatgacg gttccgagga agccaaaact     1320
ttcgtgcaaa tcgtttgcca gcagtgtcag aaagcgatga ccatatccgg ggccaagttt     1380
ttcaccgttt cactggatct gttcgcatcg gttctgggag cggtcgtcac ctacttcatg     1440
gtgttggtgc agttgaaata a                                               1461

<210> SEQ ID NO 64
<211> LENGTH: 1443
<212> TYPE: DNA
<213> ORGANISM: Artificial Sequence
<220> FEATURE:
<223> OTHER INFORMATION: synthetic

<400> SEQUENCE: 64
atgacaacct cgatgcagcc gagcaagtac acgggcctgg tcgccgacct gatgcccaac       60
atccgggcga tgaagtactc cggcctgttc atgcacaact tcacgggcgg cagtgccttc      120
atgaagaagg tgtactcctc cgtgcacctg gtgttcctcc tcatgcagtt caccttcatc      180
ctggtcaaca tggccctgaa cgccgaggag gtcaacgagc tgtcgggcaa cacgatcacg      240
accctcttct tcacccactg catcacgaag tttatctacc tggctgttaa ccagaagaat      300
ttctacagaa cattgaatat atggaaccag gtgaacacgc atcccttgtt cgccgagtcg      360
gatgctcgtt accattcgat cgcactggcg aagatgagga agctgttctt tctggtgatg      420
ctgaccacag tcgcctcggc caccgcctgg accacgatca ccttctttgg cgacagcgta      480
aaaatggtgg tggaccatga gacgaactcc agcatcccgg tggagatacc ccggctgccg      540
attaagtcct tctacccgtg gaacgccagc cacggcatgt tctacatgat cagctttgcc      600
tttcagatct actacgtgct cttctcgatg atccactcca atctatgcga cgtgatgttc      660
tgctcttggc tgatattcgc ctgcgagcag ctgcagcact tgaagggcat catgaagccg      720
ctgatggagc tgtccgcctc gctggacacc tacaggccca actcggcggc cctcttcagg      780
tccctgtcgg ccggatccaa atcggagctg attttgaatg aagagaaaga tcccgacacg      840
aaagatttcg acttgaacgg tatctacaac tcgaaagcgg actggggtgc ccagttcagg      900
gcgccatcca ctttgcaaac gttcggtgac aatggcatca atggtaatcc aaatggacta      960
accaagaagc aggaactgat ggtccgaagt gcgatcaagt actgggtgga gaggcacaag     1020
cacgtcgttc gcctcgtatc ggccatcggt gaaacttacg gagccgccct gttgcttcac     1080
atgttgacct cgaccatcaa gctgaccctg ttggcttacc aggcaaccaa atcgatgca      1140 ctcaacgttt atggactgac cgtgatcggc tatctggtct atgctctggc tcaggtgttc     1200
ctgttttgca ttttcggcaa tcgattaatt gaagagagtt catcagtgat ggaggctgcc     1260
tactcgtgcc actggtatga cggttccgag gaagccaaaa cttttcgtgca aatcgttttgc    1320 cagcagtgtc agaaagcgat gaccatatcc ggggccaagt ttttcaccgt ttcactggat     1380
ctgttcgcat cggttctggg agcggtcgtc acctacttca tggtgttggt gcagttgaaa     1440
```

-continued

| | |
|---|---|
| taa | 1443 |

<210> SEQ ID NO 65
<211> LENGTH: 1440
<212> TYPE: DNA
<213> ORGANISM: Artificial Sequence
<220> FEATURE:
<223> OTHER INFORMATION: synthetic

<400> SEQUENCE: 65

| | |
|---|---|
| atgacaacct cgatgcagcc gagcaagtac acgggcctgg tcgccgacct gatgcccaac | 60 |
| atccgggcga tgaagtactc cggcctgttc atgcacaact tcacgggcgg cagtgccttc | 120 |
| atgaagaagg tgtactcctc cgtgcacctg gtgttcctcc tcatgcagtt caccttcatc | 180 |
| ctggtcaaca tggccctgaa cgccgaggag gtcaacgagc tgtcgggcaa cacgatcacg | 240 |
| accctcttct tcacccactg catcacgaag tttatctacc tggctgttaa ccagaagaat | 300 |
| ttctacagaa cattgaatat atggaaccag gtgaacacgc atcccttgtt cgccgagtcg | 360 |
| gatgctcgtt accattcgat cgcactggcg aagatgagga agctgttctt tctggtgatg | 420 |
| ctgaccacag tcgcctcggc caccgcctgg accacgatca ccttctttgg cgacagcgta | 480 |
| aaaatggtgg tggaccatga gacgaactcc agcatcccgg tggagatacc ccggctgccg | 540 |
| attaagtcct tctacccgtg gaacgccagc cacggcatgt tctacatgat cagctttgcc | 600 |
| tttcagatct actacgtgct cttctcgatg atccactcca atctatgcga cgtgatgttc | 660 |
| tgctcttggc tgatattcgc ctgcgagcag ctgcagcact tgaagggcat catgaagccg | 720 |
| ctgatggagc tgtccgcctc gctggacacc tacaggccca actcggcggc cctcttcagg | 780 |
| tccctgtcgg ccaactccaa gtcggagcta attcataatg aagaaaagga tcccggcacc | 840 |
| gacatggaca tgtcgggcat ctacagctcg aaagcggatt ggggtgccca gttcagggcg | 900 |
| ccatccactt tgcaaacgtt cggtgacaat ggcatcaatg gtaatccaaa tggactaacc | 960 |
| aagaagcagg aactgatggt ccgaagtgcg atcaagtact gggtggagag cacaagcac | 1020 |
| gtcgttcgcc tcgtatcggc catcggtgaa acttacggag ccgccctgtt gcttcacatg | 1080 |
| ttgacctcga ccatcaagct gaccctgttg gcttaccagg caaccaaaat cgatgcactc | 1140 |
| aacgtttatg gactgaccgt gatcggctat ctggtctatg ctctggctca ggtgttcctg | 1200 |
| ttttgcattt tcggcaatcg attaattgaa gagagttcat cagtgatgga ggctgcctac | 1260 |
| tcgtgccact ggtatgacgg ttccgaggaa gccaaaactt tcgtgcaaat cgtttgccag | 1320 |
| cagtgtcaga aagcgatgac catatccggg gccaagtttt tcaccgtttc actggatctg | 1380 |
| ttcgcatcgg ttctgggagc ggtcgtcacc tacttcatgg tgttggtgca gttgaaataa | 1440 |

<210> SEQ ID NO 66
<211> LENGTH: 1461
<212> TYPE: DNA
<213> ORGANISM: Artificial Sequence
<220> FEATURE:
<223> OTHER INFORMATION: synthetic

<400> SEQUENCE: 66

| | |
|---|---|
| atgacaacct cgatgcagcc gagcaagtac acgggcctgg tcgccgacct gatgcccaac | 60 |
| atccgggcga tgaagtactc cggcctgttc atgcacaact tcacgggcgg cagtgccttc | 120 |
| atgaagaagg tgtactcctc cgtgcacctg gtgttcctcc tcatgcagtt caccttcatc | 180 |
| ctggtcaaca tggccctgaa cgccgaggag gtcaacgagc tgtcgggcaa cacgatcacg | 240 |
| accctcttct tcacccactg catcacgaag tttatctacc tggctgttaa ccagaagaat | 300 |

```
ttctacagaa cattgaatat atggaaccag gtgaacacgc atcccttgtt cgccgagtcg      360
gatgctcgtt accattcgat cgcactggcg aagatgagga agctgttctt tctggtgatg      420
ctgaccacag tcgcctcggc caccgcctgg accacgatca ccttctttgg cgacagcgta      480
aaaatggtgg tggaccatga gacgaactcc agcatcccgg tggagatacc ccggctgccg      540
attaagtcct tctacccgtg gaacgccagc cacggcatgt tctacatgat cagctttgcc      600
tttcagatct actacgtgct cttctcgatg atccactcca atctatgcga cgtgatgttc      660
tgctcttggc tgatattcgc ctgcgagcag ctgcagcact gaagggcat catgaagccg       720 ctgatggagc tgtccgcctc gctggacacc tacaggccca actcggcggc cctcttcagg      780
tccctgtcgg ccaactccaa gtcggagcta attcataatg aagaaaagga tcccggcacc      840
gacatggaca tgtcgggcat ctacagctcg aaagcggatt ggggcgctca gtttcgagca      900
ccctcgacac tgcagtcctt tggcgggaac ggggcggag gcaacgggtt ggtgaacggc       960
gctaatccca atggactaac caagaagcag gaactgatgg tccgaagtgc gatcaagtac     1020
tgggtggaga ggcacaagca cgtcgttcgc ctcgtatcgg ccatcggtga aacttacgga     1080
gccgccctgt tgcttcacat gttgacctcg accatcaagc tgaccctgtt ggcttaccag     1140
gcaaccaaaa tcgatgcact caacgtttat ggactgaccg tgatcggcta tctggtctat     1200
gctctggctc aggtgttcct gttttgcatt ttcggcaatc gattaattga agagagttca     1260
tcagtgatgg aggctgccta ctcgtgccac tggtatgacg gttccgagga agccaaaact     1320
ttcgtgcaaa tcgtttgcca gcagtgtcag aaagcgatga ccatatccgg ggccaagttt     1380
ttcaccgttt cactggatct gttcgcatcg gttctgggag cggtcgtcac ctacttcatg     1440
gtgttggtgc agttgaaata a                                              1461

<210> SEQ ID NO 67
<211> LENGTH: 1461
<212> TYPE: DNA
<213> ORGANISM: Artificial Sequence
<220> FEATURE:
<223> OTHER INFORMATION: synthetic

<400> SEQUENCE: 67
atgacaacct cgatgcagcc gagcaagtac acgggcctgg tcgccgacct gatgcccaac       60
atccgggcga tgaagtactc cggcctgttc atgcacaact tcacgggcgg cagtgccttc      120
atgaagaagg tgtactcctc cgtgcacctg gtgttcctcc tcatgcagtt caccttcatc      180
ctggtcaaca tggccctgaa cgccgaggag gtcaacgagc tgtcgggcaa cacgatcacg      240
accctcttct tcacccactg catcacgaag tttatctacc tggctgttaa ccagaagaat      300
ttctacagaa cattgaatat atggaaccag gtgaacacgc atcccttgtt cgccgagtcg      360
gatgctcgtt accattcgat cgcactggcg aagatgagga agctgttctt tctggtgatg      420
ctgaccacag tcgcctcggc caccgcctgg accacgatca ccttctttgg cgacagcgta      480
aaaatggtgg tggaccatga gacgaactcc agcatcccgg tggagatacc ccggctgccg      540
attaagtcct tctacccgtg gaacgccagc cacggcatgt tctacatgat cagctttgcc      600
tttcagatct actacgtgct cttctcgatg atccactcca atctatgcga cgtgatgttc      660
tgctcttggc tgatattcgc ctgcgagcag ctgcagcact gaagggcat catgaagccg       720 ctgatggagc tgtccgcctc gctggacacc tacaggccca actcggcggc cctcttcagg      780
tccctgtcgg ccaactccaa gtcggagcta attcataatg aagaaaagga tcccggcacc      840
```

| | |
|---|---:|
| gacatggaca tgtcgggcat ctacagctcg aaagcggatt ggggcgctca gtttcgagca | 900 |
| ccctcgacac tgcagtcctt tggcgggaac ggggcggag gcaacgggtt ggtgaacggc | 960 |
| gctaatccca acgggctgac caaaaagcag gagatgatgg tgcgcagtgc catcaagtac | 1020 |
| tgggtcgagc ggcacaagca cgtggtgcga ctggtggctg ccatcggcga tacttacgga | 1080 |
| gccgccctgt tgcttcacat gttgacctcg accatcaagc tgaccctgtt ggcttaccag | 1140 |
| gcaaccaaaa tcgatgcact caacgtttat ggactgaccg tgatcggcta tctggtctat | 1200 |
| gctctggctc aggtgttcct gttttgcatt ttcggcaatc gattaattga agagagttca | 1260 |
| tcagtgatgg aggctgccta ctcgtgccac tggtatgacg gttccgagga agccaaaact | 1320 |
| ttcgtgcaaa tcgtttgcca gcagtgtcag aaagcgatga ccatatccgg ggccaagttt | 1380 |
| ttcaccgttt cactggatct gttcgcatcg gttctgggag cggtcgtcac ctacttcatg | 1440 |
| gtgttggtgc agttgaaata a | 1461 |

<210> SEQ ID NO 68
<211> LENGTH: 1443
<212> TYPE: DNA
<213> ORGANISM: Artificial Sequence
<220> FEATURE:
<223> OTHER INFORMATION: synthetic

<400> SEQUENCE: 68

| | |
|---|---:|
| atgacaacct cgatgcagcc gagcaagtac acgggcctgg tcgccgacct gatgcccaac | 60 |
| atccgggcga tgaagtactc cggcctgttc atgcacaact tcacgggcgg cagtgccttc | 120 |
| atgaagaagg tgtactcctc cgtgcacctg gtgttcctcc tcatgcagtt caccttcatc | 180 |
| ctggtcaaca tggccctgaa cgccgaggag gtcaacgagc tgtcgggcaa cacgatcacg | 240 |
| accctcttct tcacccactg catcacgaag tttatctacc tggctgttaa ccagaagaat | 300 |
| ttctacagaa cattgaatat atggaaccag gtgaacacgc atcccttgtt cgccgagtcg | 360 |
| gatgctcgtt accattcgat cgcactggcg aagatgagga agctgttctt tctggtgatg | 420 |
| ctgaccacag tcgcctcggc caccgcctgg accacgatca ccttctttgg cgacagcgta | 480 |
| aaaatggtgg tggaccatga gacgaactcc agcatcccgg tggagatacc ccggctgccg | 540 |
| attaagtcct tctacccgtg gaacgccagc cacggcatgt tctacatgat cagctttgcc | 600 |
| tttcagatct actacgtgct cttctcgatg atccacgcca acctcgccga tgtgatgttt | 660 |
| tgctcctggc tgcttttcac ttgcgaacag ctgcaacatt tgaagggtat aatgcgcccc | 720 |
| ctgatggaac tttccgccac gctggacacc taccgaccaa actcggctgc cctgttccgt | 780 |
| gtcgcttccg ccggatccaa atcggagctg attttgaatg aagagaaaga tcccgacacg | 840 |
| aaagatttcg acttgaacgg tatctacaac tcgaaagcgg actggggtgc ccagttcagg | 900 |
| gcgccatcca ctttgcaaac gttcggtgac aatggcatca atggtaatcc aaatggacta | 960 |
| accaagaagc aggaactgat ggtccgaagt gcgatcaagt actgggtgga gaggcacaag | 1020 |
| cacgtcgttc gcctcgtatc ggccatcggt gaaacttacg gagccgccct gttgcttcac | 1080 |
| atgttgacct cgaccatcaa gctgacccctg ttggcttacc aggcaaccaa aatcgatgca | 1140 |
| ctcaacgttt atggactgac cgtgatcggc tatctggtct atgctctggc tcaggtgttc | 1200 |
| ctgttttgca ttttcggcaa tcgattaatt gaagagagtt catcagtgat ggaggctgcc | 1260 |
| tactcgtgcc actggtatga cggttccgag gaagccaaaa cttttcgtgca aatcgtttgc | 1320 |
| cagcagtgtc agaaagcgat gaccatatcc ggggccaagt ttttcaccgt ttcactggat | 1380 |
| ctgttcgcat cggttctggg agcggtcgtc acctacttca tggtgttggt gcagttgaaa | 1440 | taa 1443

<210> SEQ ID NO 69
<211> LENGTH: 480
<212> TYPE: PRT
<213> ORGANISM: Artificial Sequence
<220> FEATURE:
<223> OTHER INFORMATION: synthetic

<400> SEQUENCE: 69

Met Thr Thr Ser Met Gln Pro Ser Lys Tyr Thr Gly Leu Val Ala Asp
1               5                   10                  15

Leu Met Pro Asn Ile Arg Ala Met Lys Tyr Ser Gly Leu Phe Met His
                20                  25                  30

Asn Phe Thr Gly Gly Ser Ala Phe Met Lys Lys Val Tyr Ser Ser Val
            35                  40                  45

His Leu Val Phe Leu Leu Met Gln Phe Thr Phe Ile Leu Val Asn Met
        50                  55                  60

Ala Leu Asn Ala Glu Glu Val Asn Glu Leu Ser Gly Asn Thr Ile Thr
65                  70                  75                  80

Thr Leu Phe Phe Thr His Ser Val Thr Lys Phe Ile Tyr Val Ala Val
                85                  90                  95

Asn Ser Glu His Phe Tyr Arg Thr Leu Gly Ile Trp Asn Gln Pro Asn
                100                 105                 110

Ser His Ser Leu Phe Ala Glu Ser Asp Ala Arg Tyr His Ser Ile Ala
            115                 120                 125

Leu Ala Lys Met Arg Lys Leu Val Met Val Met Val Thr Thr Val
        130                 135                 140

Leu Ser Val Val Ala Trp Ile Thr Ile Thr Phe Phe Gly Asp Ser Val
145                 150                 155                 160

Lys Asn Val Phe Asp Lys Glu Thr Asn Glu Thr Tyr Thr Val Glu Ile
                165                 170                 175

Pro Arg Leu Pro Ile Lys Ala Trp Tyr Pro Trp Asp Ala Met Ser Gly
                180                 185                 190

Val Pro Tyr Phe Phe Ser Phe Ile Tyr Gln Ala Tyr Phe Leu Leu Phe
            195                 200                 205

Ser Met Cys Gln Ala Asn Leu Ala Asp Val Met Phe Cys Ser Trp Leu
        210                 215                 220

Leu Phe Thr Cys Glu Gln Leu Gln His Leu Lys Gly Ile Met Arg Pro
225                 230                 235                 240

Leu Met Glu Leu Ser Ala Thr Leu Asp Thr Tyr Arg Pro Asn Ser Ala
                245                 250                 255

Ala Leu Phe Arg Val Ala Ser Ala Gly Ser Lys Ser Glu Leu Ile Leu
                260                 265                 270

Asn Glu Glu Lys Asp Pro Asp Thr Lys Asp Phe Asp Leu Asn Gly Ile
            275                 280                 285

Tyr Asn Ser Lys Ala Asp Trp Gly Ala Gln Phe Arg Ala Pro Ser Thr
        290                 295                 300

Leu Gln Thr Phe Gly Asp Asn Gly Ile Asn Gly Asn Pro Asn Gly Leu
305                 310                 315                 320

Thr Lys Lys Gln Glu Leu Met Val Arg Ser Ala Ile Lys Tyr Trp Val
                325                 330                 335

Glu Arg His Lys His Val Val Arg Leu Val Ser Ala Ile Gly Glu Thr
                340                 345                 350

```
Tyr Gly Ala Ala Leu Leu Leu His Met Leu Thr Ser Thr Ile Lys Leu
            355                 360                 365

Thr Leu Leu Ala Tyr Gln Ala Thr Lys Ile Asp Ala Leu Asn Val Tyr
370                 375                 380

Gly Leu Thr Val Ile Gly Tyr Leu Val Tyr Ala Leu Ala Gln Val Phe
385                 390                 395                 400

Leu Phe Cys Ile Phe Gly Asn Arg Leu Ile Glu Ser Ser Ser Val
                405                 410                 415

Met Glu Ala Ala Tyr Ser Cys His Trp Tyr Asp Gly Ser Glu Ala
            420                 425                 430

Lys Thr Phe Val Gln Ile Val Cys Gln Gln Cys Gln Lys Ala Met Thr
        435                 440                 445

Ile Ser Gly Ala Lys Phe Phe Thr Val Ser Leu Asp Leu Phe Ala Ser
450                 455                 460

Val Leu Gly Ala Val Val Thr Tyr Phe Met Val Leu Val Gln Leu Lys
465                 470                 475                 480

<210> SEQ ID NO 70
<211> LENGTH: 480
<212> TYPE: PRT
<213> ORGANISM: Artificial Sequence
<220> FEATURE:
<223> OTHER INFORMATION: sunthetic

<400> SEQUENCE: 70

Met Thr Thr Ser Met Gln Pro Ser Lys Tyr Thr Gly Leu Val Ala Asp
1               5                   10                  15

Leu Met Pro Asn Ile Arg Ala Met Lys Tyr Ser Gly Leu Phe Met His
            20                  25                  30

Asn Phe Thr Gly Gly Ser Ala Phe Met Lys Lys Val Tyr Ser Ser Val
        35                  40                  45

His Leu Val Phe Leu Leu Met Gln Phe Thr Phe Ile Leu Val Asn Met
    50                  55                  60

Ala Leu Asn Ala Glu Glu Val Asn Glu Leu Ser Gly Asn Thr Ile Thr
65                  70                  75                  80

Thr Leu Phe Phe Thr His Cys Ile Thr Lys Phe Ile Tyr Leu Ala Val
                85                  90                  95

Asn Gln Lys Asn Phe Tyr Arg Thr Leu Asn Ile Trp Asn Gln Val Asn
            100                 105                 110

Thr His Pro Leu Phe Ala Glu Ser Asp Ala Arg Tyr His Ser Ile Ala
        115                 120                 125

Leu Ala Lys Met Arg Lys Leu Phe Phe Leu Val Met Leu Thr Thr Val
130                 135                 140

Ala Ser Ala Thr Ala Trp Thr Thr Ile Thr Phe Phe Gly Asp Ser Val
145                 150                 155                 160

Lys Asn Val Phe Asp Lys Glu Thr Asn Glu Thr Tyr Thr Val Glu Ile
                165                 170                 175

Pro Arg Leu Pro Ile Lys Ala Trp Tyr Pro Trp Asp Ala Met Ser Gly
            180                 185                 190

Val Pro Tyr Phe Phe Ser Phe Ile Tyr Gln Ala Tyr Phe Leu Leu Phe
        195                 200                 205

Ser Met Cys Gln Ala Asn Leu Ala Asp Val Met Phe Cys Ser Trp Leu
210                 215                 220

Leu Phe Thr Cys Glu Gln Leu Gln His Leu Lys Gly Ile Met Arg Pro
225                 230                 235                 240
```

Leu Met Glu Leu Ser Ala Thr Leu Asp Thr Tyr Arg Pro Asn Ser Ala
            245                 250                 255

Ala Leu Phe Arg Val Ala Ser Ala Gly Ser Lys Ser Glu Leu Ile Leu
        260                 265                 270

Asn Glu Glu Lys Asp Pro Asp Thr Lys Asp Phe Asp Leu Asn Gly Ile
            275                 280                 285

Tyr Asn Ser Lys Ala Asp Trp Gly Ala Gln Phe Arg Ala Pro Ser Thr
        290                 295                 300

Leu Gln Thr Phe Gly Asp Asn Gly Ile Asn Gly Asn Pro Asn Gly Leu
305                 310                 315                 320

Thr Lys Lys Gln Glu Leu Met Val Arg Ser Ala Ile Lys Tyr Trp Val
                325                 330                 335

Glu Arg His Lys His Val Val Arg Leu Val Ser Ala Ile Gly Glu Thr
            340                 345                 350

Tyr Gly Ala Ala Leu Leu Leu His Met Leu Thr Ser Thr Ile Lys Leu
        355                 360                 365

Thr Leu Leu Ala Tyr Gln Ala Thr Lys Ile Asp Ala Leu Asn Val Tyr
    370                 375                 380

Gly Leu Thr Val Ile Gly Tyr Leu Val Tyr Ala Leu Ala Gln Val Phe
385                 390                 395                 400

Leu Phe Cys Ile Phe Gly Asn Arg Leu Ile Glu Ser Ser Ser Val
                405                 410                 415

Met Glu Ala Ala Tyr Ser Cys His Trp Tyr Asp Gly Ser Glu Glu Ala
                420                 425                 430

Lys Thr Phe Val Gln Ile Val Cys Gln Gln Cys Gln Lys Ala Met Thr
            435                 440                 445

Ile Ser Gly Ala Lys Phe Phe Thr Val Ser Leu Asp Leu Phe Ala Ser
        450                 455                 460

Val Leu Gly Ala Val Val Thr Tyr Phe Met Val Leu Val Gln Leu Lys
465                 470                 475                 480

<210> SEQ ID NO 71
<211> LENGTH: 480
<212> TYPE: PRT
<213> ORGANISM: Artificial Sequence
<220> FEATURE:
<223> OTHER INFORMATION: synthetic

<400> SEQUENCE: 71

Met Thr Thr Ser Met Gln Pro Ser Lys Tyr Thr Gly Leu Val Ala Asp
1               5                   10                  15

Leu Met Pro Asn Ile Arg Ala Met Lys Tyr Ser Gly Leu Phe Met His
            20                  25                  30

Asn Phe Thr Gly Gly Ser Ala Phe Met Lys Lys Val Tyr Ser Ser Val
        35                  40                  45

His Leu Val Phe Leu Leu Met Gln Phe Thr Phe Ile Leu Val Asn Met
    50                  55                  60

Ala Leu Asn Ala Glu Glu Val Asn Glu Leu Ser Gly Asn Thr Ile Thr
65                  70                  75                  80

Thr Leu Phe Phe Thr His Cys Ile Thr Lys Phe Ile Tyr Leu Ala Val
                85                  90                  95

Asn Gln Lys Asn Phe Tyr Arg Thr Leu Asn Ile Trp Asn Gln Val Asn
            100                 105                 110

Thr His Pro Leu Phe Ala Glu Ser Asp Ala Arg Tyr His Ser Ile Ala
        115                 120                 125

Leu Ala Lys Met Arg Lys Leu Phe Phe Leu Val Met Leu Thr Thr Val
130                 135                 140

Ala Ser Ala Thr Ala Trp Thr Thr Ile Thr Phe Phe Gly Asp Ser Val
145                 150                 155                 160

Lys Met Val Val Asp His Glu Thr Asn Ser Ser Ile Pro Val Glu Ile
                165                 170                 175

Pro Arg Leu Pro Ile Lys Ser Phe Tyr Pro Trp Asn Ala Ser His Gly
                180                 185                 190

Met Phe Tyr Met Ile Ser Phe Ala Phe Gln Ile Tyr Tyr Val Leu Phe
            195                 200                 205

Ser Met Ile His Ser Asn Leu Cys Asp Val Met Phe Cys Ser Trp Leu
210                 215                 220

Ile Phe Ala Cys Glu Gln Leu Gln His Leu Lys Gly Ile Met Arg Pro
225                 230                 235                 240

Leu Met Glu Leu Ser Ala Thr Leu Asp Thr Tyr Arg Pro Asn Ser Ala
                245                 250                 255

Ala Leu Phe Arg Val Ala Ser Ala Gly Ser Lys Ser Glu Leu Ile Leu
                260                 265                 270

Asn Glu Glu Lys Asp Pro Asp Thr Lys Asp Phe Asp Leu Asn Gly Ile
            275                 280                 285

Tyr Asn Ser Lys Ala Asp Trp Gly Ala Gln Phe Arg Ala Pro Ser Thr
290                 295                 300

Leu Gln Thr Phe Gly Asp Asn Gly Ile Asn Gly Asn Pro Asn Gly Leu
305                 310                 315                 320

Thr Lys Lys Gln Glu Leu Met Val Arg Ser Ala Ile Lys Tyr Trp Val
                325                 330                 335

Glu Arg His Lys His Val Val Arg Leu Val Ser Ala Ile Gly Glu Thr
                340                 345                 350

Tyr Gly Ala Ala Leu Leu Leu His Met Leu Thr Ser Thr Ile Lys Leu
            355                 360                 365

Thr Leu Leu Ala Tyr Gln Ala Thr Lys Ile Asp Ala Leu Asn Val Tyr
370                 375                 380

Gly Leu Thr Val Ile Gly Tyr Leu Val Tyr Ala Leu Ala Gln Val Phe
385                 390                 395                 400

Leu Phe Cys Ile Phe Gly Asn Arg Leu Ile Glu Glu Ser Ser Val
                405                 410                 415

Met Glu Ala Ala Tyr Ser Cys His Trp Tyr Asp Gly Ser Glu Glu Ala
            420                 425                 430

Lys Thr Phe Val Gln Ile Val Cys Gln Gln Cys Gln Lys Ala Met Thr
                435                 440                 445

Ile Ser Gly Ala Lys Phe Phe Thr Val Ser Leu Asp Leu Phe Ala Ser
450                 455                 460

Val Leu Gly Ala Val Val Thr Tyr Phe Met Val Leu Val Gln Leu Lys
465                 470                 475                 480

<210> SEQ ID NO 72
<211> LENGTH: 486
<212> TYPE: PRT
<213> ORGANISM: Artificial Sequence
<220> FEATURE:
<223> OTHER INFORMATION: synthetic

<400> SEQUENCE: 72

Met Thr Thr Ser Met Gln Pro Ser Lys Tyr Thr Gly Leu Val Ala Asp
1               5                   10                  15

-continued

```
Leu Met Pro Asn Ile Arg Ala Met Lys Tyr Ser Gly Leu Phe Met His
        20                  25                  30

Asn Phe Thr Gly Gly Ser Ala Phe Met Lys Lys Val Tyr Ser Ser Val
            35                  40                  45

His Leu Val Phe Leu Leu Met Gln Phe Thr Phe Ile Leu Val Asn Met
 50                      55                  60

Ala Leu Asn Ala Glu Glu Val Asn Glu Leu Ser Gly Asn Thr Ile Thr
 65                  70                  75                  80

Thr Leu Phe Phe Thr His Cys Ile Thr Lys Phe Ile Tyr Leu Ala Val
                85                  90                  95

Asn Gln Lys Asn Phe Tyr Arg Thr Leu Asn Ile Trp Asn Gln Val Asn
                100                 105                 110

Thr His Pro Leu Phe Ala Glu Ser Asp Ala Arg Tyr His Ser Ile Ala
            115                 120                 125

Leu Ala Lys Met Arg Lys Leu Phe Phe Leu Val Met Leu Thr Thr Val
        130                 135                 140

Ala Ser Ala Thr Ala Trp Thr Thr Ile Thr Phe Phe Gly Asp Ser Val
145                 150                 155                 160

Lys Met Val Val Asp His Glu Thr Asn Ser Ser Ile Pro Val Glu Ile
                165                 170                 175

Pro Arg Leu Pro Ile Lys Ser Phe Tyr Pro Trp Asn Ala Ser His Gly
            180                 185                 190

Met Phe Tyr Met Ile Ser Phe Ala Phe Gln Ile Tyr Tyr Val Leu Phe
        195                 200                 205

Ser Met Ile His Ser Asn Leu Cys Asp Val Met Phe Cys Ser Trp Leu
210                 215                 220

Ile Phe Ala Cys Glu Gln Leu Gln His Leu Lys Gly Ile Met Lys Pro
225                 230                 235                 240

Leu Met Glu Leu Ser Ala Ser Leu Asp Thr Tyr Arg Pro Asn Ser Ala
                245                 250                 255

Ala Leu Phe Arg Ser Leu Ser Ala Asn Ser Lys Ser Glu Leu Ile His
            260                 265                 270

Asn Glu Glu Lys Asp Pro Gly Thr Asp Met Asp Met Ser Gly Ile Tyr
        275                 280                 285

Ser Ser Lys Ala Asp Trp Gly Ala Gln Phe Arg Ala Pro Ser Thr Leu
290                 295                 300

Gln Ser Phe Gly Gly Asn Gly Gly Gly Gly Asn Gly Leu Val Asn Gly
305                 310                 315                 320

Ala Asn Pro Asn Gly Leu Thr Lys Lys Gln Glu Met Met Val Arg Ser
                325                 330                 335

Ala Ile Lys Tyr Trp Val Glu Arg His Lys His Val Val Arg Leu Val
            340                 345                 350

Ala Ala Ile Gly Asp Thr Tyr Gly Ala Ala Leu Leu Leu His Met Leu
        355                 360                 365

Thr Ser Thr Ile Lys Leu Thr Leu Leu Ala Tyr Gln Ala Thr Lys Ile
370                 375                 380

Asp Ala Leu Asn Val Tyr Gly Leu Thr Val Ile Gly Tyr Leu Val Tyr
385                 390                 395                 400

Ala Leu Ala Gln Val Phe Leu Phe Cys Ile Phe Gly Asn Arg Leu Ile
                405                 410                 415

Glu Glu Ser Ser Ser Val Met Glu Ala Ala Tyr Ser Cys His Trp Tyr
            420                 425                 430

Asp Gly Ser Glu Glu Ala Lys Thr Phe Val Gln Ile Val Cys Gln Gln
```

```
                435                 440                 445
Cys Gln Lys Ala Met Thr Ile Ser Gly Ala Lys Phe Phe Thr Val Ser
            450                 455                 460

Leu Asp Leu Phe Ala Ser Val Leu Gly Ala Val Val Thr Tyr Phe Met
465                 470                 475                 480

Val Leu Val Gln Leu Lys
                485

<210> SEQ ID NO 73
<211> LENGTH: 486
<212> TYPE: PRT
<213> ORGANISM: Artificial Sequence
<220> FEATURE:
<223> OTHER INFORMATION: synthetic

<400> SEQUENCE: 73

Met Thr Thr Ser Met Gln Pro Ser Lys Tyr Thr Gly Leu Val Ala Asp
1               5                   10                  15

Leu Met Pro Asn Ile Arg Ala Met Lys Tyr Ser Gly Leu Phe Met His
            20                  25                  30

Asn Phe Thr Gly Gly Ser Ala Phe Met Lys Lys Val Tyr Ser Ser Val
        35                  40                  45

His Leu Val Phe Leu Leu Met Gln Phe Thr Phe Ile Leu Val Asn Met
    50                  55                  60

Ala Leu Asn Ala Glu Glu Val Asn Glu Leu Ser Gly Asn Thr Ile Thr
65                  70                  75                  80

Thr Leu Phe Phe Thr His Cys Ile Thr Lys Phe Ile Tyr Leu Ala Val
                85                  90                  95

Asn Gln Lys Asn Phe Tyr Arg Thr Leu Asn Ile Trp Asn Gln Val Asn
            100                 105                 110

Thr His Pro Leu Phe Ala Glu Ser Asp Ala Arg Tyr His Ser Ile Ala
        115                 120                 125

Leu Ala Lys Met Arg Lys Leu Phe Phe Leu Val Met Leu Thr Thr Val
    130                 135                 140

Ala Ser Ala Thr Ala Trp Thr Thr Ile Thr Phe Phe Gly Asp Ser Val
145                 150                 155                 160

Lys Met Val Val Asp His Glu Thr Asn Ser Ser Ile Pro Val Glu Ile
                165                 170                 175

Pro Arg Leu Pro Ile Lys Ser Phe Tyr Pro Trp Asn Ala Ser His Gly
            180                 185                 190

Met Phe Tyr Met Ile Ser Phe Ala Phe Gln Ile Tyr Tyr Val Leu Phe
        195                 200                 205

Ser Met Ile His Ser Asn Leu Cys Asp Val Met Phe Cys Ser Trp Leu
    210                 215                 220

Ile Phe Ala Cys Glu Gln Leu Gln His Leu Lys Gly Ile Met Lys Pro
225                 230                 235                 240

Leu Met Glu Leu Ser Ala Ser Leu Asp Thr Tyr Arg Pro Asn Ser Ala
                245                 250                 255

Ala Leu Phe Arg Ser Leu Ser Ala Asn Ser Lys Ser Glu Leu Ile His
            260                 265                 270

Asn Glu Glu Lys Asp Pro Gly Thr Asp Met Asp Met Ser Gly Ile Tyr
        275                 280                 285

Ser Ser Lys Ala Asp Trp Gly Ala Gln Phe Arg Ala Pro Ser Thr Leu
    290                 295                 300

Gln Ser Phe Gly Gly Asn Gly Gly Gly Asn Gly Leu Val Asn Gly
```

```
                305                 310                 315                 320
Ala Asn Pro Asn Gly Leu Thr Lys Lys Gln Glu Met Met Val Arg Ser
                    325                 330                 335

Ala Ile Lys Tyr Trp Val Glu Arg His Lys His Val Val Arg Leu Val
                    340                 345                 350

Ala Ala Ile Gly Asp Thr Tyr Gly Ala Ala Leu Leu Leu His Met Leu
                    355                 360                 365

Thr Ser Thr Ile Lys Leu Thr Leu Leu Ala Tyr Gln Ala Thr Lys Ile
                    370                 375                 380

Asn Gly Val Asn Val Tyr Ala Phe Thr Val Val Gly Tyr Leu Gly Tyr
385                 390                 395                 400

Ala Leu Ala Gln Val Phe His Phe Cys Ile Phe Gly Asn Arg Leu Ile
                    405                 410                 415

Glu Glu Ser Ser Ser Val Met Glu Ala Ala Tyr Ser Cys His Trp Tyr
                    420                 425                 430

Asp Gly Ser Glu Glu Ala Lys Thr Phe Val Gln Ile Val Cys Gln Gln
                    435                 440                 445

Cys Gln Lys Ala Met Thr Ile Ser Gly Ala Lys Phe Phe Thr Val Ser
                    450                 455                 460

Leu Asp Leu Phe Ala Ser Val Leu Gly Ala Val Val Thr Tyr Phe Met
465                 470                 475                 480

Val Leu Val Gln Leu Lys
                    485

<210> SEQ ID NO 74
<211> LENGTH: 480
<212> TYPE: PRT
<213> ORGANISM: Artificial Sequence
<220> FEATURE:
<223> OTHER INFORMATION: synthetic

<400> SEQUENCE: 74

Met Thr Thr Ser Met Gln Pro Ser Lys Tyr Thr Gly Leu Val Ala Asp
1               5                   10                  15

Leu Met Pro Asn Ile Arg Ala Met Lys Tyr Ser Gly Leu Phe Met His
                20                  25                  30

Asn Phe Thr Gly Gly Ser Ala Phe Met Lys Lys Val Tyr Ser Ser Val
                35                  40                  45

His Leu Val Phe Leu Leu Met Gln Phe Thr Phe Ile Leu Val Asn Met
            50                  55                  60

Ala Leu Asn Ala Glu Glu Val Asn Glu Leu Ser Gly Asn Thr Ile Thr
65                  70                  75                  80

Thr Leu Phe Phe Thr His Cys Ile Thr Lys Phe Ile Tyr Leu Ala Val
                85                  90                  95

Asn Gln Lys Asn Phe Tyr Arg Thr Leu Asn Ile Trp Asn Gln Val Asn
                    100                 105                 110

Thr His Pro Leu Phe Ala Glu Ser Asp Ala Arg Tyr His Ser Ile Ala
                115                 120                 125

Leu Ala Lys Met Arg Lys Leu Phe Phe Leu Val Met Leu Thr Thr Val
            130                 135                 140

Ala Ser Ala Thr Ala Trp Thr Thr Ile Thr Phe Phe Gly Asp Ser Val
145                 150                 155                 160

Lys Met Val Val Asp His Glu Thr Asn Ser Ser Ile Pro Val Glu Ile
                165                 170                 175

Pro Arg Leu Pro Ile Lys Ser Phe Tyr Pro Trp Asn Ala Ser His Gly
```

```
                180             185             190
Met Phe Tyr Met Ile Ser Phe Ala Phe Gln Ile Tyr Tyr Val Leu Phe
            195             200             205

Ser Met Ile His Ser Asn Leu Cys Asp Val Met Phe Cys Ser Trp Leu
210             215             220

Ile Phe Ala Cys Glu Gln Leu Gln His Leu Lys Gly Ile Met Lys Pro
225             230             235             240

Leu Met Glu Leu Ser Ala Ser Leu Asp Thr Tyr Arg Pro Asn Ser Ala
            245             250             255

Ala Leu Phe Arg Ser Leu Ser Ala Gly Ser Lys Ser Glu Leu Ile Leu
            260             265             270

Asn Glu Glu Lys Asp Pro Asp Thr Lys Asp Phe Asp Leu Asn Gly Ile
        275             280             285

Tyr Asn Ser Lys Ala Asp Trp Gly Ala Gln Phe Arg Ala Pro Ser Thr
        290             295             300

Leu Gln Thr Phe Gly Asp Asn Gly Ile Asn Gly Asn Pro Asn Gly Leu
305             310             315             320

Thr Lys Lys Gln Glu Leu Met Val Arg Ser Ala Ile Lys Tyr Trp Val
            325             330             335

Glu Arg His Lys His Val Val Arg Leu Val Ser Ala Ile Gly Glu Thr
            340             345             350

Tyr Gly Ala Ala Leu Leu Leu His Met Leu Thr Ser Thr Ile Lys Leu
            355             360             365

Thr Leu Leu Ala Tyr Gln Ala Thr Lys Ile Asp Ala Leu Asn Val Tyr
370             375             380

Gly Leu Thr Val Ile Gly Tyr Leu Val Tyr Ala Leu Ala Gln Val Phe
385             390             395             400

Leu Phe Cys Ile Phe Gly Asn Arg Leu Ile Glu Glu Ser Ser Ser Val
            405             410             415

Met Glu Ala Ala Tyr Ser Cys His Trp Tyr Asp Gly Ser Glu Glu Ala
            420             425             430

Lys Thr Phe Val Gln Ile Val Cys Gln Gln Cys Gln Lys Ala Met Thr
            435             440             445

Ile Ser Gly Ala Lys Phe Phe Thr Val Ser Leu Asp Leu Phe Ala Ser
        450             455             460

Val Leu Gly Ala Val Val Thr Tyr Phe Met Val Leu Gln Leu Lys
465             470             475             480

<210> SEQ ID NO 75
<211> LENGTH: 479
<212> TYPE: PRT
<213> ORGANISM: Artificial Sequence
<220> FEATURE:
<223> OTHER INFORMATION: synthetic

<400> SEQUENCE: 75

Met Thr Thr Ser Met Gln Pro Ser Lys Tyr Thr Gly Leu Val Ala Asp
1               5               10              15

Leu Met Pro Asn Ile Arg Ala Met Lys Tyr Ser Gly Leu Phe Met His
            20              25              30

Asn Phe Thr Gly Gly Ser Ala Phe Met Lys Lys Val Tyr Ser Ser Val
        35              40              45

His Leu Val Phe Leu Leu Met Gln Phe Thr Phe Ile Leu Val Asn Met
    50              55              60

Ala Leu Asn Ala Glu Glu Val Asn Glu Leu Ser Gly Asn Thr Ile Thr
```

```
            65                  70                  75                  80
Thr Leu Phe Phe Thr His Cys Ile Thr Lys Phe Ile Tyr Leu Ala Val
                    85                  90                  95

Asn Gln Lys Asn Phe Tyr Arg Thr Leu Asn Ile Trp Asn Gln Val Asn
                100                 105                 110

Thr His Pro Leu Phe Ala Glu Ser Asp Ala Arg Tyr His Ser Ile Ala
                115                 120                 125

Leu Ala Lys Met Arg Lys Leu Phe Phe Leu Val Met Leu Thr Thr Val
                130                 135                 140

Ala Ser Ala Thr Ala Trp Thr Thr Ile Thr Phe Phe Gly Asp Ser Val
145                 150                 155                 160

Lys Met Val Val Asp His Glu Thr Asn Ser Ser Ile Pro Val Glu Ile
                165                 170                 175

Pro Arg Leu Pro Ile Lys Ser Phe Tyr Pro Trp Asn Ala Ser His Gly
                180                 185                 190

Met Phe Tyr Met Ile Ser Phe Ala Phe Gln Ile Tyr Tyr Val Leu Phe
                195                 200                 205

Ser Met Ile His Ser Asn Leu Cys Asp Val Met Phe Cys Ser Trp Leu
                210                 215                 220

Ile Phe Ala Cys Glu Gln Leu Gln His Leu Lys Gly Ile Met Lys Pro
225                 230                 235                 240

Leu Met Glu Leu Ser Ala Ser Leu Asp Thr Tyr Arg Pro Asn Ser Ala
                245                 250                 255

Ala Leu Phe Arg Ser Leu Ser Ala Asn Ser Lys Ser Glu Leu Ile His
                260                 265                 270

Asn Glu Glu Lys Asp Pro Gly Thr Asp Met Asp Met Ser Gly Ile Tyr
                275                 280                 285

Ser Ser Lys Ala Asp Trp Gly Ala Gln Phe Arg Ala Pro Ser Thr Leu
                290                 295                 300

Gln Thr Phe Gly Asp Asn Gly Ile Asn Gly Asn Pro Asn Gly Leu Thr
305                 310                 315                 320

Lys Lys Gln Glu Leu Met Val Arg Ser Ala Ile Lys Tyr Trp Val Glu
                325                 330                 335

Arg His Lys His Val Val Arg Leu Val Ser Ala Ile Gly Glu Thr Tyr
                340                 345                 350

Gly Ala Ala Leu Leu Leu His Met Leu Thr Ser Thr Ile Lys Leu Thr
                355                 360                 365

Leu Leu Ala Tyr Gln Ala Thr Lys Ile Asp Ala Leu Asn Val Tyr Gly
                370                 375                 380

Leu Thr Val Ile Gly Tyr Leu Val Tyr Ala Leu Ala Gln Val Phe Leu
385                 390                 395                 400

Phe Cys Ile Phe Gly Asn Arg Leu Ile Glu Glu Ser Ser Ser Val Met
                405                 410                 415

Glu Ala Ala Tyr Ser Cys His Trp Tyr Asp Gly Ser Glu Glu Ala Lys
                420                 425                 430

Thr Phe Val Gln Ile Val Cys Gln Gln Cys Gln Lys Ala Met Thr Ile
                435                 440                 445

Ser Gly Ala Lys Phe Phe Thr Val Ser Leu Asp Leu Phe Ala Ser Val
                450                 455                 460

Leu Gly Ala Val Val Thr Tyr Phe Met Val Leu Val Gln Leu Lys
465                 470                 475

<210> SEQ ID NO 76
```

<211> LENGTH: 486
<212> TYPE: PRT
<213> ORGANISM: Artificial Sequence
<220> FEATURE:
<223> OTHER INFORMATION: synthetic

<400> SEQUENCE: 76

```
Met Thr Thr Ser Met Gln Pro Ser Lys Tyr Thr Gly Leu Val Ala Asp
1               5                   10                  15

Leu Met Pro Asn Ile Arg Ala Met Lys Tyr Ser Gly Leu Phe Met His
                20                  25                  30

Asn Phe Thr Gly Gly Ser Ala Phe Met Lys Lys Val Tyr Ser Ser Val
            35                  40                  45

His Leu Val Phe Leu Leu Met Gln Phe Thr Phe Ile Leu Val Asn Met
    50                  55                  60

Ala Leu Asn Ala Glu Glu Val Asn Glu Leu Ser Gly Asn Thr Ile Thr
65                  70                  75                  80

Thr Leu Phe Phe Thr His Cys Ile Thr Lys Phe Ile Tyr Leu Ala Val
                85                  90                  95

Asn Gln Lys Asn Phe Tyr Arg Thr Leu Asn Ile Trp Asn Gln Val Asn
                100                 105                 110

Thr His Pro Leu Phe Ala Glu Ser Asp Ala Arg Tyr His Ser Ile Ala
            115                 120                 125

Leu Ala Lys Met Arg Lys Leu Phe Phe Leu Val Met Leu Thr Thr Val
    130                 135                 140

Ala Ser Ala Thr Ala Trp Thr Thr Ile Thr Phe Phe Gly Asp Ser Val
145                 150                 155                 160

Lys Met Val Val Asp His Glu Thr Asn Ser Ser Ile Pro Val Glu Ile
                165                 170                 175

Pro Arg Leu Pro Ile Lys Ser Phe Tyr Pro Trp Asn Ala Ser His Gly
                180                 185                 190

Met Phe Tyr Met Ile Ser Phe Ala Phe Gln Ile Tyr Tyr Val Leu Phe
            195                 200                 205

Ser Met Ile His Ser Asn Leu Cys Asp Val Met Phe Cys Ser Trp Leu
    210                 215                 220

Ile Phe Ala Cys Glu Gln Leu Gln His Leu Lys Gly Ile Met Lys Pro
225                 230                 235                 240

Leu Met Glu Leu Ser Ala Ser Leu Asp Thr Tyr Arg Pro Asn Ser Ala
                245                 250                 255

Ala Leu Phe Arg Ser Leu Ser Ala Asn Ser Lys Ser Glu Leu Ile His
                260                 265                 270

Asn Glu Glu Lys Asp Pro Gly Thr Asp Met Asp Met Ser Gly Ile Tyr
            275                 280                 285

Ser Ser Lys Ala Asp Trp Gly Ala Gln Phe Arg Ala Pro Ser Thr Leu
    290                 295                 300

Gln Ser Phe Gly Gly Asn Gly Gly Gly Asn Gly Leu Val Asn Gly
305                 310                 315                 320

Ala Asn Pro Asn Gly Leu Thr Lys Lys Gln Glu Leu Met Val Arg Ser
                325                 330                 335

Ala Ile Lys Tyr Trp Val Glu Arg His Lys His Val Val Arg Leu Val
                340                 345                 350

Ser Ala Ile Gly Glu Thr Tyr Gly Ala Ala Leu Leu Leu His Met Leu
            355                 360                 365

Thr Ser Thr Ile Lys Leu Thr Leu Leu Ala Tyr Gln Ala Thr Lys Ile
    370                 375                 380
```

Asp Ala Leu Asn Val Tyr Gly Leu Thr Val Ile Gly Tyr Leu Val Tyr
385                 390                 395                 400

Ala Leu Ala Gln Val Phe Leu Phe Cys Ile Phe Gly Asn Arg Leu Ile
                405                 410                 415

Glu Glu Ser Ser Ser Val Met Glu Ala Ala Tyr Ser Cys His Trp Tyr
                420                 425                 430

Asp Gly Ser Glu Glu Ala Lys Thr Phe Val Gln Ile Val Cys Gln Gln
                435                 440                 445

Cys Gln Lys Ala Met Thr Ile Ser Gly Ala Lys Phe Phe Thr Val Ser
        450                 455                 460

Leu Asp Leu Phe Ala Ser Val Leu Gly Ala Val Val Tyr Phe Met
465                 470                 475                 480

Val Leu Val Gln Leu Lys
                485

<210> SEQ ID NO 77
<211> LENGTH: 486
<212> TYPE: PRT
<213> ORGANISM: Artificial Sequence
<220> FEATURE:
<223> OTHER INFORMATION: synthetic

<400> SEQUENCE: 77

Met Thr Thr Ser Met Gln Pro Ser Lys Tyr Thr Gly Leu Val Ala Asp
1               5                   10                  15

Leu Met Pro Asn Ile Arg Ala Met Lys Tyr Ser Gly Leu Phe Met His
                20                  25                  30

Asn Phe Thr Gly Gly Ser Ala Phe Met Lys Lys Val Tyr Ser Ser Val
                35                  40                  45

His Leu Val Phe Leu Leu Met Gln Phe Thr Phe Ile Leu Val Asn Met
        50                  55                  60

Ala Leu Asn Ala Glu Glu Val Asn Glu Leu Ser Gly Asn Thr Ile Thr
65                  70                  75                  80

Thr Leu Phe Phe Thr His Cys Ile Thr Lys Phe Ile Tyr Leu Ala Val
                85                  90                  95

Asn Gln Lys Asn Phe Tyr Arg Thr Leu Asn Ile Trp Asn Gln Val Asn
                100                 105                 110

Thr His Pro Leu Phe Ala Glu Ser Asp Ala Arg Tyr His Ser Ile Ala
            115                 120                 125

Leu Ala Lys Met Arg Lys Leu Phe Leu Val Met Leu Thr Thr Val
130                 135                 140

Ala Ser Ala Thr Ala Trp Thr Thr Ile Thr Phe Phe Gly Asp Ser Val
145                 150                 155                 160

Lys Met Val Val Asp His Glu Thr Asn Ser Ser Ile Pro Val Glu Ile
                165                 170                 175

Pro Arg Leu Pro Ile Lys Ser Phe Tyr Pro Trp Asn Ala Ser His Gly
                180                 185                 190

Met Phe Tyr Met Ile Ser Phe Ala Phe Gln Ile Tyr Tyr Val Leu Phe
                195                 200                 205

Ser Met Ile His Ser Asn Leu Cys Asp Val Met Phe Cys Ser Trp Leu
        210                 215                 220

Ile Phe Ala Cys Glu Gln Leu Gln His Leu Lys Gly Ile Met Lys Pro
225                 230                 235                 240

Leu Met Glu Leu Ser Ala Ser Leu Asp Thr Tyr Arg Pro Asn Ser Ala
                245                 250                 255

```
Ala Leu Phe Arg Ser Leu Ser Ala Asn Ser Lys Ser Glu Leu Ile His
            260                 265                 270

Asn Glu Glu Lys Asp Pro Gly Thr Asp Met Asp Met Ser Gly Ile Tyr
            275                 280                 285

Ser Ser Lys Ala Asp Trp Gly Ala Gln Phe Arg Ala Pro Ser Thr Leu
            290                 295                 300

Gln Ser Phe Gly Gly Asn Gly Gly Gly Asn Gly Leu Val Asn Gly
305                 310                 315                 320

Ala Asn Pro Asn Gly Leu Thr Lys Lys Gln Glu Met Met Val Arg Ser
            325                 330                 335

Ala Ile Lys Tyr Trp Val Glu Arg His Lys His Val Val Arg Leu Val
            340                 345                 350

Ala Ala Ile Gly Asp Thr Tyr Gly Ala Ala Leu Leu Leu His Met Leu
            355                 360                 365

Thr Ser Thr Ile Lys Leu Thr Leu Leu Ala Tyr Gln Ala Thr Lys Ile
            370                 375                 380

Asp Ala Leu Asn Val Tyr Gly Leu Thr Val Ile Gly Tyr Leu Val Tyr
385                 390                 395                 400

Ala Leu Ala Gln Val Phe Leu Phe Cys Ile Phe Gly Asn Arg Leu Ile
            405                 410                 415

Glu Glu Ser Ser Ser Val Met Glu Ala Ala Tyr Ser Cys His Trp Tyr
            420                 425                 430

Asp Gly Ser Glu Glu Ala Lys Thr Phe Val Gln Ile Val Cys Gln Gln
            435                 440                 445

Cys Gln Lys Ala Met Thr Ile Ser Gly Ala Lys Phe Phe Thr Val Ser
            450                 455                 460

Leu Asp Leu Phe Ala Ser Val Leu Gly Ala Val Val Thr Tyr Phe Met
465                 470                 475                 480

Val Leu Val Gln Leu Lys
            485

<210> SEQ ID NO 78
<211> LENGTH: 480
<212> TYPE: PRT
<213> ORGANISM: Artificial Sequence
<220> FEATURE:
<223> OTHER INFORMATION: synthetic

<400> SEQUENCE: 78

Met Thr Thr Ser Met Gln Pro Ser Lys Tyr Thr Gly Leu Val Ala Asp
1               5                   10                  15

Leu Met Pro Asn Ile Arg Ala Met Lys Tyr Ser Gly Leu Phe Met His
            20                  25                  30

Asn Phe Thr Gly Gly Ser Ala Phe Met Lys Lys Val Tyr Ser Ser Val
            35                  40                  45

His Leu Val Phe Leu Leu Met Gln Phe Thr Phe Ile Leu Val Asn Met
            50                  55                  60

Ala Leu Asn Ala Glu Glu Val Asn Glu Leu Ser Gly Asn Thr Ile Thr
65                  70                  75                  80

Thr Leu Phe Phe Thr His Cys Ile Thr Lys Phe Ile Tyr Leu Ala Val
            85                  90                  95

Asn Gln Lys Asn Phe Tyr Arg Thr Leu Asn Ile Trp Asn Gln Val Asn
            100                 105                 110

Thr His Pro Leu Phe Ala Glu Ser Asp Ala Arg Tyr His Ser Ile Ala
            115                 120                 125
```

Leu Ala Lys Met Arg Lys Leu Phe Phe Leu Val Met Leu Thr Thr Val
    130                 135                 140

Ala Ser Ala Thr Ala Trp Thr Thr Ile Thr Phe Phe Gly Asp Ser Val
145                 150                 155                 160

Lys Met Val Val Asp His Glu Thr Asn Ser Ser Ile Pro Val Glu Ile
                165                 170                 175

Pro Arg Leu Pro Ile Lys Ser Phe Tyr Pro Trp Asn Ala Ser His Gly
            180                 185                 190

Met Phe Tyr Met Ile Ser Phe Ala Phe Gln Ile Tyr Tyr Val Leu Phe
        195                 200                 205

Ser Met Ile His Ala Asn Leu Ala Asp Val Met Phe Cys Ser Trp Leu
    210                 215                 220

Leu Phe Thr Cys Glu Gln Leu Gln His Leu Lys Gly Ile Met Arg Pro
225                 230                 235                 240

Leu Met Glu Leu Ser Ala Thr Leu Asp Thr Tyr Arg Pro Asn Ser Ala
                245                 250                 255

Ala Leu Phe Arg Val Ala Ser Ala Gly Ser Lys Ser Glu Leu Ile Leu
            260                 265                 270

Asn Glu Glu Lys Asp Pro Asp Thr Lys Asp Phe Asp Leu Asn Gly Ile
        275                 280                 285

Tyr Asn Ser Lys Ala Asp Trp Gly Ala Gln Phe Arg Ala Pro Ser Thr
    290                 295                 300

Leu Gln Thr Phe Gly Asp Asn Gly Ile Asn Gly Asn Pro Asn Gly Leu
305                 310                 315                 320

Thr Lys Lys Gln Glu Leu Met Val Arg Ser Ala Ile Lys Tyr Trp Val
                325                 330                 335

Glu Arg His Lys His Val Val Arg Leu Val Ser Ala Ile Gly Glu Thr
            340                 345                 350

Tyr Gly Ala Ala Leu Leu Leu His Met Leu Thr Ser Thr Ile Lys Leu
        355                 360                 365

Thr Leu Leu Ala Tyr Gln Ala Thr Lys Ile Asp Ala Leu Asn Val Tyr
370                 375                 380

Gly Leu Thr Val Ile Gly Tyr Leu Val Tyr Ala Leu Ala Gln Val Phe
385                 390                 395                 400

Leu Phe Cys Ile Phe Gly Asn Arg Leu Ile Glu Glu Ser Ser Ser Val
                405                 410                 415

Met Glu Ala Ala Tyr Ser Cys His Trp Tyr Asp Gly Ser Glu Glu Ala
            420                 425                 430

Lys Thr Phe Val Gln Ile Val Cys Gln Gln Cys Gln Lys Ala Met Thr
        435                 440                 445

Ile Ser Gly Ala Lys Phe Phe Thr Val Ser Leu Asp Leu Phe Ala Ser
    450                 455                 460

Val Leu Gly Ala Val Val Thr Tyr Phe Met Val Leu Val Gln Leu Lys
465                 470                 475                 480

<210> SEQ ID NO 79
<211> LENGTH: 1437
<212> TYPE: DNA
<213> ORGANISM: Artificial Sequence
<220> FEATURE:
<223> OTHER INFORMATION: synthetic

<400> SEQUENCE: 79
atgaacgtcc aaccgacaaa gtaccatggg ctggtgctcg acttgatgcc gaacatccgg    60

```
ctgatgcagg gcttcggtca ctttctgttc cgttacgtaa atgggccggt cctgattaag    120
aaggtgtact cctccgtgca cctggtgttc ctcctcatgc agttcacctt catcctggtc    180
aacatggcca tgaatacagg ggacgtcaat gagctaacgg caaacaccat cacgaccctc    240
ttcttcaccc actgcatcac gaagtttatc tacctggctg ttaactcgga acatttctac    300
cgcacgctgg gcatctggaa tcaaccgaac agtcattcac tttttgccga atcggatgct    360
cggtaccatt cgattgcgtt ggctaagatg cgaaaactgt tctttctggt gatgctgacc    420
acagtcgcct cggccaccgc ctggaccacg atcaccttct ttggcgatag cgtcaaaaac    480
gtattcgaca aagagactaa cgaaacgtat acggtggaaa ttccccgatt gcccatcaag    540
gcttggtacc cgtgggatgc aatgcacggc atgttctaca tgatcagctt tgcctttcag    600
atctactacg tgctcttctc gatgatccac tccaatctat gcgacgtgat gttctgctct    660
tggctgatat tcgcctgcga gcagctgcag cacttgaagg gtataatgcg cccctgatg    720 gaactttccg ccacgctgga cacctaccga ccaaactcgg ctgccctgtt ccgtgtcgct    780
tccgccggat ccaaatcgga gctgattttg aatgaagaga agatcccga cacgaaagat    840 ttcgacttga acggtatcta caactcgaaa gcggactggg gtgcccagtt cagggcgcca    900
tccactttgc aaacgttcgg tgacaatggc atcaatggta atccaaatgg actaaccaag    960
aagcaggaac tgatggtccg aagtgcgatc aagtactggg tggagaggca caagcacgtc   1020
gttcgcctcg tatcggccat cggtgaaact tacgagccg ccctgttgct tcacatgttg   1080
acctcgacca tcaagctgac cctgttggct taccaggcaa ccaaaatcga tgcactcaac   1140
gtttatggac tgaccgtgat cggctatctg gtctatgctc tggctcaggt gttcctgttt   1200 tgcatttttcg gcaatcgatt aattgaagag agttcatcag tgatggaggc tgcctactcg   1260
tgccactggt atgacggttc cgaggaagcc aaaactttcg tgcaaatcgt ttgccagcag   1320
tgtcagaaag cgatgaccat atccggggcc aagttttca ccgtttcact ggatctgttc   1380
gcatcggttc tgggagcggt cgtcacctac ttcatggtgt tggtgcagtt gaaataa      1437
```

<210> SEQ ID NO 80
<211> LENGTH: 44
<212> TYPE: DNA
<213> ORGANISM: Artificial Sequence
<220> FEATURE:
<223> OTHER INFORMATION: synthetic

<400> SEQUENCE: 80

```
tggaattctg cagatcacca tgaacgtcca accgacaaag tacc              44
```

<210> SEQ ID NO 81
<211> LENGTH: 35
<212> TYPE: DNA
<213> ORGANISM: Artificial Sequence
<220> FEATURE:
<223> OTHER INFORMATION: synthetic

<400> SEQUENCE: 81

```
gccactgtgc tggatttatt tcaactgcac caaca                        35
```

<210> SEQ ID NO 82
<211> LENGTH: 478
<212> TYPE: PRT
<213> ORGANISM: Artificial Sequence
<220> FEATURE:
<223> OTHER INFORMATION: synthetic

<400> SEQUENCE: 82

-continued

```
Met Asn Val Gln Pro Thr Lys Tyr His Gly Leu Val Leu Asp Leu Met
1               5                   10                  15

Pro Asn Ile Arg Leu Met Gln Gly Phe Gly His Phe Leu Phe Arg Tyr
            20                  25                  30

Val Asn Gly Pro Val Leu Ile Lys Lys Val Tyr Ser Ser Val His Leu
            35                  40                  45

Val Phe Leu Leu Met Gln Phe Thr Phe Ile Leu Val Asn Met Ala Met
50                      55                  60

Asn Thr Gly Asp Val Asn Glu Leu Thr Ala Asn Thr Ile Thr Thr Leu
65                  70                  75                  80

Phe Phe Thr His Cys Ile Thr Lys Phe Ile Tyr Leu Ala Val Asn Ser
                85                  90                  95

Glu His Phe Tyr Arg Thr Leu Gly Ile Trp Asn Gln Pro Asn Ser His
                100                 105                 110

Ser Leu Phe Ala Glu Ser Asp Ala Arg Tyr His Ser Ile Ala Leu Ala
            115                 120                 125

Lys Met Arg Lys Leu Phe Phe Leu Val Met Leu Thr Thr Val Ala Ser
130                 135                 140

Ala Thr Ala Trp Thr Thr Ile Thr Phe Phe Gly Asp Ser Val Lys Asn
145                 150                 155                 160

Val Phe Asp Lys Glu Thr Asn Glu Thr Tyr Thr Val Glu Ile Pro Arg
                165                 170                 175

Leu Pro Ile Lys Ala Trp Tyr Pro Trp Asp Ala Met His Gly Met Phe
            180                 185                 190

Tyr Met Ile Ser Phe Ala Phe Gln Ile Tyr Tyr Val Leu Phe Ser Met
                195                 200                 205

Ile His Ser Asn Leu Cys Asp Val Met Phe Cys Ser Trp Leu Ile Phe
            210                 215                 220

Ala Cys Glu Gln Leu Gln His Leu Lys Gly Ile Met Arg Pro Leu Met
225                 230                 235                 240

Glu Leu Ser Ala Thr Leu Asp Thr Tyr Arg Pro Asn Ser Ala Ala Leu
                245                 250                 255

Phe Arg Val Ala Ser Ala Gly Ser Lys Ser Glu Leu Ile Leu Asn Glu
            260                 265                 270

Glu Lys Asp Pro Asp Thr Lys Asp Phe Asp Leu Asn Gly Ile Tyr Asn
            275                 280                 285

Ser Lys Ala Asp Trp Gly Ala Gln Phe Arg Ala Pro Ser Thr Leu Gln
            290                 295                 300

Thr Phe Gly Asp Asn Gly Ile Asn Gly Asn Pro Asn Gly Leu Thr Lys
305                 310                 315                 320

Lys Gln Glu Leu Met Val Arg Ser Ala Ile Lys Tyr Trp Val Glu Arg
                325                 330                 335

His Lys His Val Val Arg Leu Val Ser Ala Ile Gly Glu Thr Tyr Gly
                340                 345                 350

Ala Ala Leu Leu Leu His Met Leu Thr Ser Thr Ile Lys Leu Thr Leu
                355                 360                 365

Leu Ala Tyr Gln Ala Thr Lys Ile Asp Ala Leu Asn Val Tyr Gly Leu
            370                 375                 380

Thr Val Ile Gly Tyr Leu Val Tyr Ala Leu Ala Gln Val Phe Leu Phe
385                 390                 395                 400

Cys Ile Phe Gly Asn Arg Leu Ile Glu Glu Ser Ser Val Met Glu
                405                 410                 415
```

Ala Ala Tyr Ser Cys His Trp Tyr Asp Gly Ser Glu Glu Ala Lys Thr
            420                 425                 430

Phe Val Gln Ile Val Cys Gln Gln Cys Gln Lys Ala Met Thr Ile Ser
        435                 440                 445

Gly Ala Lys Phe Phe Thr Val Ser Leu Asp Leu Phe Ala Ser Val Leu
    450                 455                 460

Gly Ala Val Val Thr Tyr Phe Met Val Leu Val Gln Leu Lys
465                 470                 475

<210> SEQ ID NO 83
<211> LENGTH: 1443
<212> TYPE: DNA
<213> ORGANISM: Artificial Sequence
<220> FEATURE:
<223> OTHER INFORMATION: synthetic

<400> SEQUENCE: 83

| | | | | |
|---|---|---|---|---|
| atgacaacct cgatgcagcc gagcaagtac acgggcctgg tcgccgacct gatgcccaac | | | | 60 |
| atccgggcga tgaagtactc cggcctgttc atgcacaact tcacgggcgg cagtgccttc | | | | 120 |
| atgcggaagc tgtactcctg gtggaacctg ataatgatcc tgctgcaata ttttgccatc | | | | 180 |
| atgggcaatc tggtgctgaa cgccgaggag gtcaacgagc tgtcgggcaa cacgataacg | | | | 240 |
| acgctgtttt tcacccattc tgtgaccaag ttcatctacg tcgccgtcaa ccagaagaat | | | | 300 |
| ttctacagaa cattgaatat atggaaccag gtgaacacga tcccttgtt cgccgagtcg | | | | 360 |
| gatgctcgtt accattcgat cgcactggcg aagatgagga agctgctggt catggtgatg | | | | 420 |
| gtgactacag tgctatccgt cgtcgcatgg atcacgataa cattcttcgg cgacagcgta | | | | 480 |
| aaaatggtgg tggaccatga cgaactcc agcatcccgg tggagatacc ccggctgccg | | | | 540 |
| attaagtcct ctacccgtg gaacgccagc agcggagtgc cgtacttttt ctccttcatc | | | | 600 |
| taccaggctt atttcctact gttttcgatg tgccaggcca acctcgccga tgtgatgttt | | | | 660 |
| tgctcctggc tgcttttcac ttgcgaacag ctgcaacatt tgaagggtat aatgcgcccc | | | | 720 |
| ctgatggaac tttccgccac gctggacacc taccgaccaa actcggctgc cctgttccgt | | | | 780 |
| gtcgcttccg ccggatccaa atcggagctg attttgaatg aagagaaaga tcccgacacg | | | | 840 |
| aaagatttcg acttgaacgg tatctacaac tcgaaagcgg actgggtgc ccagttcagg | | | | 900 |
| gcgccatcca ctttgcaaac gttcggtgac aatggcatca atggtaatcc aaatggacta | | | | 960 |
| accaagaagc aggaactgat ggtccgaagt gcgatcaagt actgggtgga gaggcacaag | | | | 1020 |
| cacgtcgttc gcctcgtatc ggccatcggt gaaacttacg gagccgccct gttgcttcac | | | | 1080 |
| atgttgacct cgaccatcaa gctgaccctg ttggcttacc aggcaaccaa atcgatgca | | | | 1140 |
| ctcaacgttt atggactgac cgtgatcggc tatctggtct atgctctggc tcaggtgttc | | | | 1200 |
| ctgttttgca ttttcggcaa tcgattaatt gaagagagtt catcagtgat ggaggctgcc | | | | 1260 |
| tactcgtgcc actggtatga cggttccgag gaagccaaaa ctttcgtgca aatcgtttgc | | | | 1320 |
| cagcagtgtc agaaagcgat gaccatatcc ggggccaagt ttttcaccgt ttcactggat | | | | 1380 |
| ctgttcgcat cggttctggg agcggtcgtc acctacttca tggtgttggt gcagttgaaa | | | | 1440 |
| taa | | | | 1443 |

<210> SEQ ID NO 84
<211> LENGTH: 45
<212> TYPE: DNA
<213> ORGANISM: Artificial Sequence
<220> FEATURE:
<223> OTHER INFORMATION: synthetic -continued

<400> SEQUENCE: 84
tggaattctg cagatcacca tgacaacctc gatgcagccg agcaa        45

<210> SEQ ID NO 85
<211> LENGTH: 35
<212> TYPE: DNA
<213> ORGANISM: Artificial Sequence
<220> FEATURE:
<223> OTHER INFORMATION: synthetic

<400> SEQUENCE: 85
gccactgtgc tggatttatt tcaactgcac caaca        35

<210> SEQ ID NO 86
<211> LENGTH: 480
<212> TYPE: PRT
<213> ORGANISM: Artificial Sequence
<220> FEATURE:
<223> OTHER INFORMATION: synthetic

<400> SEQUENCE: 86

```
Met Thr Thr Ser Met Gln Pro Ser Lys Tyr Thr Gly Leu Val Ala Asp
1               5                   10                  15

Leu Met Pro Asn Ile Arg Ala Met Lys Tyr Ser Gly Leu Phe Met His
            20                  25                  30

Asn Phe Thr Gly Gly Ser Ala Phe Met Arg Lys Leu Tyr Ser Trp Trp
        35                  40                  45

Asn Leu Ile Met Ile Leu Leu Gln Tyr Phe Ala Ile Met Gly Asn Leu
    50                  55                  60

Val Leu Asn Ala Glu Glu Val Asn Glu Leu Ser Gly Asn Thr Ile Thr
65                  70                  75                  80

Thr Leu Phe Phe Thr His Ser Val Thr Lys Phe Ile Tyr Val Ala Val
                85                  90                  95

Asn Gln Lys Asn Phe Tyr Arg Thr Leu Asn Ile Trp Asn Gln Val Asn
            100                 105                 110

Thr His Pro Leu Phe Ala Glu Ser Asp Ala Arg Tyr His Ser Ile Ala
        115                 120                 125

Leu Ala Lys Met Arg Lys Leu Leu Val Met Val Met Val Thr Thr Val
    130                 135                 140

Leu Ser Val Val Ala Trp Ile Thr Ile Thr Phe Phe Gly Asp Ser Val
145                 150                 155                 160

Lys Met Val Val Asp His Glu Thr Asn Ser Ser Ile Pro Val Glu Ile
                165                 170                 175

Pro Arg Leu Pro Ile Lys Ser Phe Tyr Pro Trp Asn Ala Ser Ser Gly
            180                 185                 190

Val Pro Tyr Phe Phe Ser Phe Ile Tyr Gln Ala Tyr Phe Leu Leu Phe
        195                 200                 205

Ser Met Cys Gln Ala Asn Leu Ala Asp Val Met Phe Cys Ser Trp Leu
    210                 215                 220

Leu Phe Thr Cys Glu Gln Leu Gln His Leu Lys Gly Ile Met Arg Pro
225                 230                 235                 240

Leu Met Glu Leu Ser Ala Thr Leu Asp Thr Tyr Arg Pro Asn Ser Ala
                245                 250                 255

Ala Leu Phe Arg Val Ala Ser Ala Gly Ser Lys Ser Glu Leu Ile Leu
            260                 265                 270

Asn Glu Glu Lys Asp Pro Asp Thr Lys Asp Phe Asp Leu Asn Gly Ile
```

275                 280                 285
Tyr Asn Ser Lys Ala Asp Trp Gly Ala Gln Phe Arg Ala Pro Ser Thr
    290                 295                 300

Leu Gln Thr Phe Gly Asp Asn Gly Ile Asn Gly Asn Pro Asn Gly Leu
305                 310                 315                 320

Thr Lys Lys Gln Glu Leu Met Val Arg Ser Ala Ile Lys Tyr Trp Val
                325                 330                 335

Glu Arg His Lys His Val Val Arg Leu Val Ser Ala Ile Gly Glu Thr
                340                 345                 350

Tyr Gly Ala Ala Leu Leu Leu His Met Leu Thr Ser Thr Ile Lys Leu
            355                 360                 365

Thr Leu Leu Ala Tyr Gln Ala Thr Lys Ile Asp Ala Leu Asn Val Tyr
370                 375                 380

Gly Leu Thr Val Ile Gly Tyr Leu Val Tyr Ala Leu Ala Gln Val Phe
385                 390                 395                 400

Leu Phe Cys Ile Phe Gly Asn Arg Leu Ile Glu Glu Ser Ser Ser Val
                405                 410                 415

Met Glu Ala Ala Tyr Ser Cys His Trp Tyr Asp Gly Ser Glu Glu Ala
                420                 425                 430

Lys Thr Phe Val Gln Ile Val Cys Gln Gln Cys Gln Lys Ala Met Thr
            435                 440                 445

Ile Ser Gly Ala Lys Phe Phe Thr Val Ser Leu Asp Leu Phe Ala Ser
        450                 455                 460

Val Leu Gly Ala Val Val Thr Tyr Phe Met Val Leu Val Gln Leu Lys
465                 470                 475                 480

<210> SEQ ID NO 87
<211> LENGTH: 40
<212> TYPE: DNA
<213> ORGANISM: Artificial Sequence
<220> FEATURE:
<223> OTHER INFORMATION: synthetic

<400> SEQUENCE: 87
acgatcacct tctttggtga ctctgtgaaa aaggtcatcg                        40

<210> SEQ ID NO 88
<211> LENGTH: 42
<212> TYPE: DNA
<213> ORGANISM: Artificial Sequence
<220> FEATURE:
<223> OTHER INFORMATION: synthetic

<400> SEQUENCE: 88
gccactgtgc tggattcact tcagttgcac caacaccatg aa                     42

<210> SEQ ID NO 89
<211> LENGTH: 40
<212> TYPE: DNA
<213> ORGANISM: Artificial Sequence
<220> FEATURE:
<223> OTHER INFORMATION: synthetic

<400> SEQUENCE: 89
cagctgcagc acttgaagaa tatcatgaag cctttgatgg                        40

<210> SEQ ID NO 90
<211> LENGTH: 42
<212> TYPE: DNA
<213> ORGANISM: Artificial Sequence
<220> FEATURE:
<223> OTHER INFORMATION: synthetic

<400> SEQUENCE: 90
gccactgtgc tggattcact tcagttgcac caacaccatg aa            42

<210> SEQ ID NO 91
<211> LENGTH: 40
<212> TYPE: DNA
<213> ORGANISM: Artificial Sequence
<220> FEATURE:
<223> OTHER INFORMATION: synthetic

<400> SEQUENCE: 91
ctggcatacc aggccacaaa gatacatgca gtagatacat               40

<210> SEQ ID NO 92
<211> LENGTH: 42
<212> TYPE: DNA
<213> ORGANISM: Artificial Sequence
<220> FEATURE:
<223> OTHER INFORMATION: synthetic

<400> SEQUENCE: 92
gccactgtgc tggattcact tcagttgcac caacaccatg aa            42

<210> SEQ ID NO 93
<211> LENGTH: 40
<212> TYPE: DNA
<213> ORGANISM: Artificial Sequence
<220> FEATURE:
<223> OTHER INFORMATION: synthetic

<400> SEQUENCE: 93
tgcatctttg gcaatcgtct cattgaagag agctcatcag               40

<210> SEQ ID NO 94
<211> LENGTH: 42
<212> TYPE: DNA
<213> ORGANISM: Artificial Sequence
<220> FEATURE:
<223> OTHER INFORMATION: synthetic

<400> SEQUENCE: 94
gccactgtgc tggattcact tcagttgcac caacaccatg aa            42

<210> SEQ ID NO 95
<211> LENGTH: 1443
<212> TYPE: DNA
<213> ORGANISM: Artificial Sequence
<220> FEATURE:
<223> OTHER INFORMATION: synthetic

<400> SEQUENCE: 95
atgacaacct cgatgcagcc gagcaagtac acgggcctgg tcgccgacct gatgcccaac    60
atccgggcga tgaagtactc cggcctgttc atgcacaact tcacgggcgg cagtgccttc   120
atgaagaagg tgtactcctc cgtgcacctg gtgttcctcc tcatgcagtt caccttcatc   180
ctggtcaaca tggccctgaa cgccgaggag gtcaacgagc tgtcgggcaa cacgatcacg   240
accctcttct tcacccactg catcacgaag tttatctacc tggctgttaa ccagaagaat   300
ttctacagaa cattgaatat atggaaccag gtgaacacgc atcccttgtt cgccgagtcg   360
gatgctcgtt accattcgat cgcactggcg aagatgagga agctgttctt tctggtgatg   420

| | |
|---|---:|
| ctgaccacag tcgcctcggc caccgcctgg accacgatca ccttctttgg tgactctgtg | 480 |
| aaaaaggtca tcgaccctgt caccaacgaa acgacctacg tcgagatacc aaggttgatg | 540 |
| gttcgttcct ggtatcctta cgacccagt cacgggatgg cccatatttt aacactgata | 600 |
| ttccaatttt actggctgat attctgcatg cggacgcga atctactgga cgtgttgttc | 660 |
| tgctcgtggc tcctgttcgc ttgcgagcag atacagcatt tgaagaatat catgaagcct | 720 |
| ttgatggaat tcagcgccac gctggacacc gtcgtgccaa acagtgggga actgttcaag | 780 |
| gctggcagtg cagagcagcc gaaggaacag gagccattgc caccagtcac gccgccccag | 840 |
| ggtgaaaaca tgttggacat ggatcttcga gggatatata gcaacaggac cgacttcacg | 900 |
| accaccttcc ggccaactgc tggaatgacg ttcaacggcg gggtcgggcc aaatggggttg | 960 |
| accaagaaac aggaaatgct ggtacgaagc gccatcaagt actgggtaga gagacacaag | 1020 |
| catatcgtta gactcgtaac tgcaattgga gacgcctatg gtgtagcttt gctgctacat | 1080 |
| atgttgacta ctactattac gttaactttg ctcgcttacc aagcaacaaa gatacatgca | 1140 |
| gtagatacat acgcagcatc agtagtaggt tatttgctat attctttagg acaagtcttt | 1200 |
| atgctctgta tatttggaaa tcgtctcatt gaagagagct catcagtgat ggaagcagct | 1260 |
| tattcttgtc actggtatga tggatcagag gaggccaaaa catttgtaca gattgtttgc | 1320 |
| cagcagtgtc agaaagcgat gtcgatttca ggggcaaagt tcttcactgt atctttggat | 1380 |
| ctctttgctt cggtgttggg agctatggtt acctacttca tggtgttggt gcaactgaag | 1440 |
| tga | 1443 |

<210> SEQ ID NO 96
<211> LENGTH: 1443
<212> TYPE: DNA
<213> ORGANISM: Artificial Sequence
<220> FEATURE:
<223> OTHER INFORMATION: synthetic

<400> SEQUENCE: 96

| | |
|---|---:|
| atgacaacct cgatgcagcc gagcaagtac acgggcctgg tcgccgacct gatgcccaac | 60 |
| atccgggcga tgaagtactc cggcctgttc atgcacaact tcacgggcgg cagtgccttc | 120 |
| atgaagaagg tgtactcctc cgtgcacctg gtgttcctcc tcatgcagtt caccttcatc | 180 |
| ctggtcaaca tggccctgaa cgccgaggag gtcaacgagc tgtcgggcaa cacgatcacg | 240 |
| accctcttct tcacccactg catcacgaag tttatctacc tggctgttaa ccagaagaat | 300 |
| ttctacagaa cattgaatat atggaaccag gtgaacacgc atcccttgtt cgccgagtcg | 360 |
| gatgctcgtt accattcgat cgcactggcg aagatgagga agctgttctt tctggtgatg | 420 |
| ctgaccacag tcgcctcggc caccgcctgg accacgatca ccttctttgg cgacagcgta | 480 |
| aaaatggtgg tggaccatga gacgaactcc agcatcccgg tggagatacc ccggctgccg | 540 |
| attaagtcct ctacccgtg aacgccagcc acggcatgt tctacatgat cagctttgcc | 600 |
| tttcagatct actacgtgct cttctcgatg atccactcca atctatgcga cgtgatgttc | 660 |
| tgctcttggc tgatattcgc ctgcgagcag ctgcagcact tgaagaatat catgaagcct | 720 |
| ttgatggaat tcagcgccac gctggacacc gtcgtgccaa acagtgggga actgttcaag | 780 |
| gctggcagtg cagagcagcc gaaggaacag gagccattgc caccagtcac gccgccccag | 840 |
| ggtgaaaaca tgttggacat ggatcttcga gggatatata gcaacaggac cgacttcacg | 900 |
| accaccttcc ggccaactgc tggaatgacg ttcaacggcg gggtcgggcc aaatggggttg | 960 |
| accaagaaac aggaaatgct ggtacgaagc gccatcaagt actgggtaga gagacacaag | 1020 |

| | |
|---|---|
| catatcgtta gactcgtaac tgcaattgga gacgcctatg gtgtagcttt gctgctacat | 1080 |
| atgttgacta ctactattac gttaactttg ctcgcttacc aagcaacaaa gatacatgca | 1140 |
| gtagatacat acgcagcatc agtagtaggt tatttgctat attctttagg acaagtcttt | 1200 |
| atgctctgta tatttggaaa tcgtctcatt gaagagagct catcagtgat ggaagcagct | 1260 |
| tattcttgtc actggtatga tggatcagag gaggccaaaa catttgtaca gattgtttgc | 1320 |
| cagcagtgtc agaaagcgat gtcgatttca ggggcaaagt tcttcactgt atctttggat | 1380 |
| ctctttgctt cggtgttggg agctatggtt acctacttca tggtgttggt gcaactgaag | 1440 |
| tga | 1443 |

<210> SEQ ID NO 97
<211> LENGTH: 1461
<212> TYPE: DNA
<213> ORGANISM: Artificial Sequence
<220> FEATURE:
<223> OTHER INFORMATION: synthetic

<400> SEQUENCE: 97

| | |
|---|---|
| atgacaacct cgatgcagcc gagcaagtac acgggcctgg tcgccgacct gatgcccaac | 60 |
| atccgggcga tgaagtactc cggcctgttc atgcacaact tcacgggcgg cagtgccttc | 120 |
| atgaagaagg tgtactcctc cgtgcacctg gtgttcctcc tcatgcagtt caccttcatc | 180 |
| ctggtcaaca tggccctgaa cgccgaggag gtcaacgagc tgtcgggcaa cacgatcacg | 240 |
| accctcttct tcacccactg catcacgaag tttatctacc tggctgttaa ccagaagaat | 300 |
| ttctacagaa cattgaatat atggaaccag gtgaacacgc atcccttgtt cgccgagtcg | 360 |
| gatgctcgtt accattcgat cgcactggcg aagatgagga agctgttctt tctggtgatg | 420 |
| ctgaccacag tcgcctcggc caccgcctgg accacgatca ccttctttgg cgacagcgta | 480 |
| aaaatggtgg tggaccatga gacgaactcc agcatcccgg tggagatacc ccggctgccg | 540 |
| attaagtcct ctacccgtg aacgccagc cacggcatgt tctacatgat cagctttgcc | 600 |
| tttcagatct actacgtgct cttctcgatg atccactcca atctatgcga cgtgatgttc | 660 |
| tgctcttggc tgatattcgc ctgcgagcag ctgcagcact gaagggcat catgaagccg | 720 |
| ctgatggagc tgtccgcctc gctggacacc tacaggccca actcggcggc cctcttcagg | 780 |
| tccctgtcgg ccaactccaa gtcggagcta attcataatg aagaaaagga tcccggcacc | 840 |
| gacatggaca tgtcgggcat ctacagctcg aaagcggatt ggggcgctca gtttcgagca | 900 |
| ccctcgacac tgcagtcctt tggcgggaac ggggcggag caacgggtt ggtgaacggc | 960 |
| gctaatccca acgggctgac caaaaagcag gagatgatgg tgcgcagtgc catcaagtac | 1020 |
| tgggtcgagc ggcacaagca cgtggtgcga ctggtggctg ccatcggcga tacttacgga | 1080 |
| gccgccctcc tcctccacat gctgacctcg accatcaagc tgaccctgct ggcataccag | 1140 |
| gccacaaaga tacatgcagt agatacatac gcagcatcag tagtaggtta tttgctatat | 1200 |
| tctttaggac aagtctttat gctctgtata tttggaaatc gtctcattga agagagctca | 1260 |
| tcagtgatgg aagcagctta ttcttgtcac tggtatgatg gatcagagga ggccaaaaca | 1320 |
| tttgtacaga ttgtttgcca gcagtgtcag aaagcgatgt cgatttcagg ggcaaagttc | 1380 |
| ttcactgtat ctttggatct ctttgcttcg gtgttgggag ctatggttac ctacttcatg | 1440 |
| gtgttggtgc aactgaagtg a | 1461 |

<210> SEQ ID NO 98

<211> LENGTH: 1461
<212> TYPE: DNA
<213> ORGANISM: Artificial Sequence
<220> FEATURE:
<223> OTHER INFORMATION: synthetic

<400> SEQUENCE: 98

```
atgacaacct cgatgcagcc gagcaagtac acgggcctgg tcgccgacct gatgcccaac      60
atccgggcga tgaagtactc cggcctgttc atgcacaact tcacgggcgg cagtgccttc     120
atgaagaagg tgtactcctc cgtgcacctg gtgttcctcc tcatgcagtt caccttcatc     180
ctggtcaaca tggccctgaa cgccgaggag gtcaacgagc tgtcgggcaa cacgatcacg     240
accctcttct tcacccactg catcacgaag tttatctacc tggctgttaa ccagaagaat     300
ttctacagaa cattgaatat atggaaccag gtgaacacgc atcccttgtt cgccgagtcg     360
gatgctcgtt accattcgat cgcactggcg aagatgagga gctgttcttt ctggtgatg     420
ctgaccacag tcgcctcggc caccgcctgg accacgatca ccttctttgg cgacagcgta     480
aaaatggtgg tggaccatga gacgaactcc agcatcccgg tggagatacc ccggctgccg     540
attaagtcct tctacccgtg gaacgccagc cacggcatgt tctacatgat cagctttgcc     600
tttcagatct actacgtgct cttctcgatg atccactcca atctatgcga cgtgatgttc     660
tgctcttggc tgatattcgc ctgcgagcag ctgcagcact tgaagggcat catgaagccg     720
ctgatggagc tgtccgcctc gctggacacc tacaggccca ctcggcggc cctcttcagg     780
tccctgtcgg ccaactccaa gtcggagcta attcataatg aagaaaagga tcccggcacc     840
gacatggaca tgtcgggcat ctacagctcg aaagcggatt ggggcgctca gtttcgagca     900
ccctcgacac tgcagtcctt tggcgggaac ggggcggag caacgggtt ggtgaacggc     960
gctaatccca acgggctgac caaaaagcag gagatgatgg tgcgcagtgc catcaagtac    1020
tgggtcgagc ggcacaagca cgtggtgcga ctggtggctg ccatcggcga tacttacgga    1080
gccgccctcc tcctccacat gctgacctcg accatcaagc tgaccctgct ggcataccag    1140
gccaccaaaa tcaacggagt gaatgtctac gccttcacag tcgtcggata cctaggatac    1200
gcgctggccc aggtgttcca cttttgcatc tttggcaatc gtctcattga agagagctca    1260
tcagtgatgg aagcagctta ttcttgtcac tggtatgatg gatcagagga ggccaaaaca    1320
tttgtacaga ttgttttgcca gcagtgtcag aaagcgatgt cgatttcagg ggcaaagttc    1380
ttcactgtat ctttggatct ctttgcttcg gtgttgggag ctatggttac ctacttcatg    1440
gtgttggtgc aactgaagtg a                                              1461
```

<210> SEQ ID NO 99
<211> LENGTH: 480
<212> TYPE: PRT
<213> ORGANISM: Artificial Sequence
<220> FEATURE:
<223> OTHER INFORMATION: synthetic

<400> SEQUENCE: 99

```
Met Thr Thr Ser Met Gln Pro Ser Lys Tyr Thr Gly Leu Val Ala Asp
1               5                   10                  15

Leu Met Pro Asn Ile Arg Ala Met Lys Tyr Ser Gly Leu Phe Met His
            20                  25                  30

Asn Phe Thr Gly Gly Ser Ala Phe Met Lys Lys Val Tyr Ser Ser Val
        35                  40                  45

His Leu Val Phe Leu Leu Met Gln Phe Thr Phe Ile Leu Val Asn Met
    50                  55                  60
```

```
Ala Leu Asn Ala Glu Glu Val Asn Glu Leu Ser Gly Asn Thr Ile Thr
 65                  70                  75                  80

Thr Leu Phe Phe Thr His Cys Ile Thr Lys Phe Ile Tyr Leu Ala Val
                 85                  90                  95

Asn Gln Lys Asn Phe Tyr Arg Thr Leu Asn Ile Trp Asn Gln Val Asn
            100                 105                 110

Thr His Pro Leu Phe Ala Glu Ser Asp Ala Arg Tyr His Ser Ile Ala
        115                 120                 125

Leu Ala Lys Met Arg Lys Leu Phe Phe Leu Val Met Leu Thr Thr Val
130                 135                 140

Ala Ser Ala Thr Ala Trp Thr Thr Ile Thr Phe Phe Gly Asp Ser Val
145                 150                 155                 160

Lys Lys Val Ile Asp Pro Val Thr Asn Glu Thr Thr Tyr Val Glu Ile
                165                 170                 175

Pro Arg Leu Met Val Arg Ser Trp Tyr Pro Tyr Asp Pro Ser His Gly
            180                 185                 190

Met Ala His Ile Leu Thr Leu Ile Phe Gln Phe Tyr Trp Leu Ile Phe
        195                 200                 205

Cys Met Ala Asp Ala Asn Leu Leu Asp Val Leu Phe Cys Ser Trp Leu
210                 215                 220

Leu Phe Ala Cys Glu Gln Ile Gln His Leu Lys Asn Ile Met Lys Pro
225                 230                 235                 240

Leu Met Glu Phe Ser Ala Thr Leu Asp Thr Val Pro Asn Ser Gly
                245                 250                 255

Glu Leu Phe Lys Ala Gly Ser Ala Glu Gln Pro Lys Glu Gln Glu Pro
            260                 265                 270

Leu Pro Pro Val Thr Pro Pro Gln Gly Glu Asn Met Leu Asp Met Asp
        275                 280                 285

Leu Arg Gly Ile Tyr Ser Asn Arg Thr Asp Phe Thr Thr Thr Phe Arg
290                 295                 300

Pro Thr Ala Gly Met Thr Phe Asn Gly Gly Val Gly Pro Asn Gly Leu
305                 310                 315                 320

Thr Lys Lys Gln Glu Met Leu Val Arg Ser Ala Ile Lys Tyr Trp Val
                325                 330                 335

Glu Arg His Lys His Ile Val Arg Leu Val Thr Ala Ile Gly Asp Ala
            340                 345                 350

Tyr Gly Val Ala Leu Leu Leu His Met Leu Thr Thr Ile Thr Leu
        355                 360                 365

Thr Leu Leu Ala Tyr Gln Ala Thr Lys Ile His Ala Val Asp Thr Tyr
        370                 375                 380

Ala Ala Ser Val Val Gly Tyr Leu Leu Tyr Ser Leu Gly Gln Val Phe
385                 390                 395                 400

Met Leu Cys Ile Phe Gly Asn Arg Leu Ile Glu Glu Ser Ser Val
                405                 410                 415

Met Glu Ala Ala Tyr Ser Cys His Trp Tyr Asp Gly Ser Glu Glu Ala
            420                 425                 430

Lys Thr Phe Val Gln Ile Val Cys Gln Gln Cys Gln Lys Ala Met Ser
        435                 440                 445

Ile Ser Gly Ala Lys Phe Phe Thr Val Ser Leu Asp Leu Phe Ala Ser
        450                 455                 460

Val Leu Gly Ala Met Val Thr Tyr Phe Met Val Leu Val Gln Leu Lys
465                 470                 475                 480
```

```
<210> SEQ ID NO 100
<211> LENGTH: 480
<212> TYPE: PRT
<213> ORGANISM: Artificial Sequence
<220> FEATURE:
<223> OTHER INFORMATION: synthetic

<400> SEQUENCE: 100
```

Met Thr Thr Ser Met Gln Pro Ser Lys Tyr Thr Gly Leu Val Ala Asp
1               5                   10                  15

Leu Met Pro Asn Ile Arg Ala Met Lys Tyr Ser Gly Leu Phe Met His
            20                  25                  30

Asn Phe Thr Gly Gly Ser Ala Phe Met Lys Lys Val Tyr Ser Ser Val
        35                  40                  45

His Leu Val Phe Leu Leu Met Gln Phe Thr Phe Ile Leu Val Asn Met
    50                  55                  60

Ala Leu Asn Ala Glu Glu Val Asn Glu Leu Ser Gly Asn Thr Ile Thr
65                  70                  75                  80

Thr Leu Phe Phe Thr His Cys Ile Thr Lys Phe Ile Tyr Leu Ala Val
                85                  90                  95

Asn Gln Lys Asn Phe Tyr Arg Thr Leu Asn Ile Trp Asn Gln Val Asn
            100                 105                 110

Thr His Pro Leu Phe Ala Glu Ser Asp Ala Arg Tyr His Ser Ile Ala
        115                 120                 125

Leu Ala Lys Met Arg Lys Leu Phe Phe Leu Val Met Leu Thr Thr Val
    130                 135                 140

Ala Ser Ala Thr Ala Trp Thr Thr Ile Thr Phe Gly Asp Ser Val
145                 150                 155                 160

Lys Met Val Val Asp His Glu Thr Asn Ser Ser Ile Pro Val Glu Ile
                165                 170                 175

Pro Arg Leu Pro Ile Lys Ser Phe Tyr Pro Trp Asn Ala Ser His Gly
            180                 185                 190

Met Phe Tyr Met Ile Ser Phe Ala Phe Gln Ile Tyr Tyr Val Leu Phe
        195                 200                 205

Ser Met Ile His Ser Asn Leu Cys Asp Val Met Phe Cys Ser Trp Leu
    210                 215                 220

Ile Phe Ala Cys Glu Gln Leu Gln His Leu Lys Asn Ile Met Lys Pro
225                 230                 235                 240

Leu Met Glu Phe Ser Ala Thr Leu Asp Thr Val Pro Asn Ser Gly
                245                 250                 255

Glu Leu Phe Lys Ala Gly Ser Ala Glu Gln Pro Lys Glu Gln Glu Pro
            260                 265                 270

Leu Pro Pro Val Thr Pro Gln Gly Glu Asn Met Leu Asp Met Asp
        275                 280                 285

Leu Arg Gly Ile Tyr Ser Asn Arg Thr Asp Phe Thr Thr Thr Phe Arg
    290                 295                 300

Pro Thr Ala Gly Met Thr Phe Asn Gly Gly Val Gly Pro Asn Gly Leu
305                 310                 315                 320

Thr Lys Lys Gln Glu Met Leu Val Arg Ser Ala Ile Lys Tyr Trp Val
                325                 330                 335

Glu Arg His Lys His Ile Val Arg Leu Val Thr Ala Ile Gly Asp Ala
            340                 345                 350

Tyr Gly Val Ala Leu Leu Leu His Met Leu Thr Thr Thr Ile Thr Leu
        355                 360                 365

```
Thr Leu Leu Ala Tyr Gln Ala Thr Lys Ile His Ala Val Asp Thr Tyr
    370                 375                 380

Ala Ala Ser Val Val Gly Tyr Leu Leu Tyr Ser Leu Gly Gln Val Phe
385                 390                 395                 400

Met Leu Cys Ile Phe Gly Asn Arg Leu Ile Glu Glu Ser Ser Val
            405                 410                 415

Met Glu Ala Ala Tyr Ser Cys His Trp Tyr Asp Gly Ser Glu Glu Ala
                420                 425                 430

Lys Thr Phe Val Gln Ile Val Cys Gln Gln Cys Gln Lys Ala Met Ser
            435                 440                 445

Ile Ser Gly Ala Lys Phe Phe Thr Val Ser Leu Asp Leu Phe Ala Ser
450                 455                 460

Val Leu Gly Ala Met Val Thr Tyr Phe Met Val Leu Val Gln Leu Lys
465                 470                 475                 480
```

<210> SEQ ID NO 101
<211> LENGTH: 486
<212> TYPE: PRT
<213> ORGANISM: Artificial Sequence
<220> FEATURE:
<223> OTHER INFORMATION: synthetic

<400> SEQUENCE: 101

```
Met Thr Thr Ser Met Gln Pro Ser Lys Tyr Thr Gly Leu Val Ala Asp
1               5                   10                  15

Leu Met Pro Asn Ile Arg Ala Met Lys Tyr Ser Gly Leu Phe Met His
            20                  25                  30

Asn Phe Thr Gly Gly Ser Ala Phe Met Lys Lys Val Tyr Ser Ser Val
        35                  40                  45

His Leu Val Phe Leu Leu Met Gln Phe Thr Phe Ile Leu Val Asn Met
    50                  55                  60

Ala Leu Asn Ala Glu Glu Val Asn Glu Leu Ser Gly Asn Thr Ile Thr
65                  70                  75                  80

Thr Leu Phe Phe Thr His Cys Ile Thr Lys Phe Ile Tyr Leu Ala Val
                85                  90                  95

Asn Gln Lys Asn Phe Tyr Arg Thr Leu Asn Ile Trp Asn Gln Val Asn
            100                 105                 110

Thr His Pro Leu Phe Ala Glu Ser Asp Ala Arg Tyr His Ser Ile Ala
        115                 120                 125

Leu Ala Lys Met Arg Lys Leu Phe Phe Leu Val Met Leu Thr Thr Val
    130                 135                 140

Ala Ser Ala Thr Ala Trp Thr Thr Ile Thr Phe Phe Gly Asp Ser Val
145                 150                 155                 160

Lys Met Val Val Asp His Glu Thr Asn Ser Ser Ile Pro Val Glu Ile
                165                 170                 175

Pro Arg Leu Pro Ile Lys Ser Phe Tyr Pro Trp Asn Ala Ser His Gly
            180                 185                 190

Met Phe Tyr Met Ile Ser Phe Ala Phe Gln Ile Tyr Tyr Val Leu Phe
        195                 200                 205

Ser Met Ile His Ser Asn Leu Cys Asp Val Met Phe Cys Ser Trp Leu
    210                 215                 220

Ile Phe Ala Cys Glu Gln Leu Gln His Leu Lys Gly Ile Met Lys Pro
225                 230                 235                 240

Leu Met Glu Leu Ser Ala Ser Leu Asp Thr Tyr Arg Pro Asn Ser Ala
                245                 250                 255
```

```
Ala Leu Phe Arg Ser Leu Ser Ala Asn Ser Lys Ser Glu Leu Ile His
            260                 265                 270

Asn Glu Glu Lys Asp Pro Gly Thr Asp Met Asp Met Ser Gly Ile Tyr
        275                 280                 285

Ser Ser Lys Ala Asp Trp Gly Ala Gln Phe Arg Ala Pro Ser Thr Leu
    290                 295                 300

Gln Ser Phe Gly Gly Asn Gly Gly Gly Asn Gly Leu Val Asn Gly
305                 310                 315                 320

Ala Asn Pro Asn Gly Leu Thr Lys Lys Gln Glu Met Met Val Arg Ser
                325                 330                 335

Ala Ile Lys Tyr Trp Val Glu Arg His Lys His Val Val Arg Leu Val
            340                 345                 350

Ala Ala Ile Gly Asp Thr Tyr Gly Ala Ala Leu Leu Leu His Met Leu
        355                 360                 365

Thr Ser Thr Ile Lys Leu Thr Leu Leu Ala Tyr Gln Ala Thr Lys Ile
    370                 375                 380

His Ala Val Asp Thr Tyr Ala Ala Ser Val Val Gly Tyr Leu Leu Tyr
385                 390                 395                 400

Ser Leu Gly Gln Val Phe Met Leu Cys Ile Phe Gly Asn Arg Leu Ile
                405                 410                 415

Glu Glu Ser Ser Ser Val Met Glu Ala Ala Tyr Ser Cys His Trp Tyr
            420                 425                 430

Asp Gly Ser Glu Glu Ala Lys Thr Phe Val Gln Ile Val Cys Gln Gln
        435                 440                 445

Cys Gln Lys Ala Met Ser Ile Ser Gly Ala Lys Phe Phe Thr Val Ser
    450                 455                 460

Leu Asp Leu Phe Ala Ser Val Leu Gly Ala Met Val Thr Tyr Phe Met
465                 470                 475                 480

Val Leu Val Gln Leu Lys
                485

<210> SEQ ID NO 102
<211> LENGTH: 486
<212> TYPE: PRT
<213> ORGANISM: Artificial Sequence
<220> FEATURE:
<223> OTHER INFORMATION: synthetic

<400> SEQUENCE: 102

Met Thr Thr Ser Met Gln Pro Ser Lys Tyr Thr Gly Leu Val Ala Asp
1               5                   10                  15

Leu Met Pro Asn Ile Arg Ala Met Lys Tyr Ser Gly Leu Phe Met His
            20                  25                  30

Asn Phe Thr Gly Gly Ser Ala Phe Met Lys Lys Val Tyr Ser Ser Val
        35                  40                  45

His Leu Val Phe Leu Leu Met Gln Phe Thr Phe Ile Leu Val Asn Met
    50                  55                  60

Ala Leu Asn Ala Glu Glu Val Asn Glu Leu Ser Gly Asn Thr Ile Thr
65                  70                  75                  80

Thr Leu Phe Phe Thr His Cys Ile Thr Lys Phe Ile Tyr Leu Ala Val
                85                  90                  95

Asn Gln Lys Asn Phe Tyr Arg Thr Leu Asn Ile Trp Asn Gln Val Asn
            100                 105                 110

Thr His Pro Leu Phe Ala Glu Ser Asp Ala Arg Tyr His Ser Ile Ala
        115                 120                 125
```

Leu Ala Lys Met Arg Lys Leu Phe Phe Leu Val Met Leu Thr Thr Val
130                 135                 140

Ala Ser Ala Thr Ala Trp Thr Thr Ile Thr Phe Phe Gly Asp Ser Val
145                 150                 155                 160

Lys Met Val Val Asp His Glu Thr Asn Ser Ser Ile Pro Val Glu Ile
                165                 170                 175

Pro Arg Leu Pro Ile Lys Ser Phe Tyr Pro Trp Asn Ala Ser His Gly
            180                 185                 190

Met Phe Tyr Met Ile Ser Phe Ala Phe Gln Ile Tyr Tyr Val Leu Phe
        195                 200                 205

Ser Met Ile His Ser Asn Leu Cys Asp Val Met Phe Cys Ser Trp Leu
210                 215                 220

Ile Phe Ala Cys Glu Gln Leu Gln His Leu Lys Gly Ile Met Lys Pro
225                 230                 235                 240

Leu Met Glu Leu Ser Ala Ser Leu Asp Thr Tyr Arg Pro Asn Ser Ala
                245                 250                 255

Ala Leu Phe Arg Ser Leu Ser Ala Asn Ser Lys Ser Glu Leu Ile His
            260                 265                 270

Asn Glu Glu Lys Asp Pro Gly Thr Asp Met Asp Met Ser Gly Ile Tyr
        275                 280                 285

Ser Ser Lys Ala Asp Trp Gly Ala Gln Phe Arg Ala Pro Ser Thr Leu
290                 295                 300

Gln Ser Phe Gly Gly Asn Gly Gly Gly Gly Asn Gly Leu Val Asn Gly
305                 310                 315                 320

Ala Asn Pro Asn Gly Leu Thr Lys Lys Gln Glu Met Met Val Arg Ser
                325                 330                 335

Ala Ile Lys Tyr Trp Val Glu Arg His Lys His Val Val Arg Leu Val
            340                 345                 350

Ala Ala Ile Gly Asp Thr Tyr Gly Ala Ala Leu Leu Leu His Met Leu
        355                 360                 365

Thr Ser Thr Ile Lys Leu Thr Leu Leu Ala Tyr Gln Ala Thr Lys Ile
370                 375                 380

Asn Gly Val Asn Val Tyr Ala Phe Thr Val Val Gly Tyr Leu Gly Tyr
385                 390                 395                 400

Ala Leu Ala Gln Val Phe His Phe Cys Ile Phe Gly Asn Arg Leu Ile
                405                 410                 415

Glu Glu Ser Ser Ser Val Met Glu Ala Ala Tyr Ser Cys His Trp Tyr
            420                 425                 430

Asp Gly Ser Glu Glu Ala Lys Thr Phe Val Gln Ile Val Cys Gln Gln
        435                 440                 445

Cys Gln Lys Ala Met Ser Ile Ser Gly Ala Lys Phe Phe Thr Val Ser
450                 455                 460

Leu Asp Leu Phe Ala Ser Val Leu Gly Ala Met Val Thr Tyr Phe Met
465                 470                 475                 480

Val Leu Val Gln Leu Lys
                485

<210> SEQ ID NO 103
<211> LENGTH: 44
<212> TYPE: DNA
<213> ORGANISM: Artificial Sequence
<220> FEATURE:
<223> OTHER INFORMATION: synthetic

<400> SEQUENCE: 103
tggaattctg cagatcacca tgaacgtcca accgacaaag tacc                44

<210> SEQ ID NO 104
<211> LENGTH: 26
<212> TYPE: DNA
<213> ORGANISM: Artificial Sequence
<220> FEATURE:
<223> OTHER INFORMATION: synthetic

<400> SEQUENCE: 104
caaatgttgc agctgttcgc aagtga                                   26

<210> SEQ ID NO 105
<211> LENGTH: 42
<212> TYPE: DNA
<213> ORGANISM: Artificial Sequence
<220> FEATURE:
<223> OTHER INFORMATION: synthetic

<400> SEQUENCE: 105
cagctgcaac atttgaagaa tatcatgaag cctttgatgg aa                  42

<210> SEQ ID NO 106
<211> LENGTH: 42
<212> TYPE: DNA
<213> ORGANISM: Artificial Sequence
<220> FEATURE:
<223> OTHER INFORMATION: synthetic

<400> SEQUENCE: 106
gccactgtgc tggattcact tcagttgcac caacaccatg aa                  42

<210> SEQ ID NO 107
<211> LENGTH: 1437
<212> TYPE: DNA
<213> ORGANISM: Artificial Sequence
<220> FEATURE:
<223> OTHER INFORMATION: synthetic

<400> SEQUENCE: 107
atgaacgtcc aaccgacaaa gtaccatggg ctggtgctcg acttgatgcc gaacatccgg    60
ctgatgcagg gcttcggtca cttctgttc cgttacgtaa atgggccggt cctgattcgg   120
aagctgtact cctggtggaa cctgataatg atcctgctgc aatattttgc catcatgggc   180
aatctggtga tgaatacagg ggacgtcaat gagctaacgg caaacaccat aacgacgctg   240
ttttcaccc attctgtgac caagttcatc tacgtcgccg tcaactcgga acatttctac   300
cgcacgctgg gcatctggaa tcaaccgaac agtcattcac ttttttgccga atcggatgct   360
cggtaccatt cgattgcgtt ggctaagatg cgaaaactgc tggtcatggt gatggtgact   420
acagtgctat ccgtcgtcgc atggatcacg ataacattct tcggcgatag cgtcaaaaac   480
gtattcgaca aagagactaa cgaaacgtat acggtggaaa ttccccgatt gcccatcaag   540
gcttggtacc cgtgggatgc aatgagcgga gtgccgtact ttttctcctt catctaccag   600
gcttatttcc tactgttttc gatgtgccag gccaacctcg ccgatgtgat gttttgctcc   660
tggctgcttt tcacttgcga acagctgcaa catttgaaga atatcatgaa gcctttgatg   720
gaattcagcg ccacgctgga caccgtcgtg ccaaacagtg gggaactgtt caaggctggc   780
agtgcagagc agccgaagga acaggagcca ttgccaccag tcacgccgcc ccagggtgaa   840
aacatgttgg acatggatct tcagggata tatagcaaca ggaccgactt cacgaccacc   900
ttccggccaa ctgctggaat gacgttcaac ggcggggtcg ggccaaatgg gttgaccaag   960

```
aaacaggaaa tgctggtacg aagcgccatc aagtactggg tagagagaca caagcatatc   1020
gttagactcg taactgcaat tggagacgcc tatggtgtag ctttgctgct acatatgttg   1080
actactacta ttacgttaac tttgctcgct taccaagcaa caaagataca tgcagtagat   1140
acatacgcag catcagtagt aggttatttg ctatattctt taggacaagt ctttatgctc   1200
tgtatatttg gaaatcgtct cattgaagag agctcatcag tgatggaagc agcttattct   1260
tgtcactggt atgatggatc agaggaggcc aaaacatttg tacagattgt ttgccagcag   1320
tgtcagaaag cgatgtcgat tcaggggca aagttcttca ctgtatcttt ggatctcttt    1380
gcttcggtgt tgggagctat ggttacctac ttcatggtgt tggtgcaact gaagtga      1437
```

<210> SEQ ID NO 108
<211> LENGTH: 478
<212> TYPE: PRT
<213> ORGANISM: Artificial Sequence
<220> FEATURE:
<223> OTHER INFORMATION: synthetic

<400> SEQUENCE: 108

```
Met Asn Val Gln Pro Thr Lys Tyr His Gly Leu Val Leu Asp Leu Met
1               5                   10                  15

Pro Asn Ile Arg Leu Met Gln Gly Phe Gly His Phe Leu Phe Arg Tyr
            20                  25                  30

Val Asn Gly Pro Val Leu Ile Arg Lys Leu Tyr Ser Trp Trp Asn Leu
        35                  40                  45

Ile Met Ile Leu Leu Gln Tyr Phe Ala Ile Met Gly Asn Leu Val Met
    50                  55                  60

Asn Thr Gly Asp Val Asn Glu Leu Thr Ala Asn Thr Ile Thr Thr Leu
65                  70                  75                  80

Phe Phe Thr His Ser Val Thr Lys Phe Ile Tyr Val Ala Val Asn Ser
                85                  90                  95

Glu His Phe Tyr Arg Thr Leu Gly Ile Trp Asn Gln Pro Asn Ser His
            100                 105                 110

Ser Leu Phe Ala Glu Ser Asp Ala Arg Tyr His Ser Ile Ala Leu Ala
        115                 120                 125

Lys Met Arg Lys Leu Leu Val Met Val Met Val Thr Thr Val Leu Ser
    130                 135                 140

Val Val Ala Trp Ile Thr Ile Thr Phe Phe Gly Asp Ser Val Lys Asn
145                 150                 155                 160

Val Phe Asp Lys Glu Thr Asn Glu Thr Tyr Thr Val Glu Ile Pro Arg
                165                 170                 175

Leu Pro Ile Lys Ala Trp Tyr Pro Trp Asp Ala Met Ser Gly Val Pro
            180                 185                 190

Tyr Phe Phe Ser Phe Ile Tyr Gln Ala Tyr Phe Leu Leu Phe Ser Met
        195                 200                 205

Cys Gln Ala Asn Leu Ala Asp Val Met Phe Cys Ser Trp Leu Leu Phe
    210                 215                 220

Thr Cys Glu Gln Leu Gln His Leu Lys Asn Ile Met Lys Pro Leu Met
225                 230                 235                 240

Glu Phe Ser Ala Thr Leu Asp Thr Val Val Pro Asn Ser Gly Glu Leu
                245                 250                 255

Phe Lys Ala Gly Ser Ala Glu Gln Pro Lys Glu Gln Glu Pro Leu Pro
            260                 265                 270

Pro Val Thr Pro Pro Gln Gly Glu Asn Met Leu Asp Met Asp Leu Arg
```

|  |  |  |  |  |  |  |  |  |  |  |  |  |
|---|---|---|---|---|---|---|---|---|---|---|---|---|
|  |  | 275 |  |  |  | 280 |  |  |  | 285 |  |  |

Gly Ile Tyr Ser Asn Arg Thr Asp Phe Thr Thr Thr Phe Arg Pro Thr
290                 295                 300

Ala Gly Met Thr Phe Asn Gly Val Gly Pro Asn Gly Leu Thr Lys
305                 310                 315                 320

Lys Gln Glu Met Leu Val Arg Ser Ala Ile Lys Tyr Trp Val Glu Arg
            325                 330                 335

His Lys His Ile Val Arg Leu Val Thr Ala Ile Gly Asp Ala Tyr Gly
        340                 345                 350

Val Ala Leu Leu Leu His Met Leu Thr Thr Thr Ile Thr Leu Thr Leu
    355                 360                 365

Leu Ala Tyr Gln Ala Thr Lys Ile His Ala Val Asp Thr Tyr Ala Ala
370                 375                 380

Ser Val Val Gly Tyr Leu Leu Tyr Ser Leu Gly Gln Val Phe Met Leu
385                 390                 395                 400

Cys Ile Phe Gly Asn Arg Leu Ile Glu Glu Ser Ser Ser Val Met Glu
            405                 410                 415

Ala Ala Tyr Ser Cys His Trp Tyr Asp Gly Ser Glu Glu Ala Lys Thr
        420                 425                 430

Phe Val Gln Ile Val Cys Gln Gln Cys Gln Lys Ala Met Ser Ile Ser
    435                 440                 445

Gly Ala Lys Phe Phe Thr Val Ser Leu Asp Leu Phe Ala Ser Val Leu
450                 455                 460

Gly Ala Met Val Thr Tyr Phe Met Val Leu Val Gln Leu Lys
465                 470                 475

<210> SEQ ID NO 109
<211> LENGTH: 45
<212> TYPE: DNA
<213> ORGANISM: Artificial Sequence
<220> FEATURE:
<223> OTHER INFORMATION: synthetic

<400> SEQUENCE: 109
tggaattctg cagatcacca tgcaagtcca gccgaccaag tacgt         45

<210> SEQ ID NO 110
<211> LENGTH: 26
<212> TYPE: DNA
<213> ORGANISM: Artificial Sequence
<220> FEATURE:
<223> OTHER INFORMATION: synthetic

<400> SEQUENCE: 110
caagtgttgc agctgctcgc aggcta         26

<210> SEQ ID NO 111
<211> LENGTH: 40
<212> TYPE: DNA
<213> ORGANISM: Artificial Sequence
<220> FEATURE:
<223> OTHER INFORMATION: synthetic

<400> SEQUENCE: 111
cagctgcaac acttgaagaa tatcatgaag cctttgatgg         40

<210> SEQ ID NO 112
<211> LENGTH: 42
<212> TYPE: DNA
<213> ORGANISM: Artificial Sequence
<220> FEATURE:
<223> OTHER INFORMATION: synthetic

<400> SEQUENCE: 112
gccactgtgc tggattcact tcagttgcac caacaccatg aa    42

<210> SEQ ID NO 113
<211> LENGTH: 1437
<212> TYPE: DNA
<213> ORGANISM: Artificial Sequence
<220> FEATURE:
<223> OTHER INFORMATION: synthetic

<400> SEQUENCE: 113

| | |
|---|---|
| atgcaagtcc agccgaccaa gtacgtcggc ctcgtcgccg acctgatgcc gaacattcgg | 60 |
| ctgatgcagg ccagcggtca ctttctgttc cgctacgtca ccggcccgat actgatccgc | 120 |
| aaggtgtact cctggtggac gctcgccatg gtgctgatcc agttcttcgc catcctcggc | 180 |
| aacctggcga cgaacgcgga cgacgtgaac gagctgaccg ccaacacgat cacgaccctg | 240 |
| ttcttcacgc actcggtcac caagttcatc tactttgcgg tcaactcgga gaacttctac | 300 |
| cggacgctcg ccatctggaa ccagaccaac acgcaccccgc tgtttgccga atcggacgcc | 360 |
| cggtaccatt cgattgcgct cgccaagatg cggaagctgc tggtgctggt gatggccacc | 420 |
| accgtcctgt cggttgtcgc ctgggttacg ataacatttt tcggcgagag cgtcaagacc | 480 |
| gtgctcgata aggcaaccaa cgagacgtac acggtggata taccccggct gcccatcaag | 540 |
| tcctggtatc cgtggaatgc aatgagcgga ccggcgtaca ttttctcttt catctaccag | 600 |
| atttacttcc tgctgttttc gatggtccag agcaacctcg cggatgtcat gttctgctcc | 660 |
| tggttgctgc tagcctgcga gcagctgcaa cacttgaaga atatcatgaa gcctttgatg | 720 |
| gaattcagcg ccacgctgga caccgtcgtg ccaaacagtg gggaactgtt caaggctggc | 780 |
| agtgcagagc agccgaagga acaggagcca ttgccaccag tcacgccgcc ccagggtgaa | 840 |
| aacatgttgg acatggatct tcgagggata tatagcaaca ggaccgactt cacgaccacc | 900 |
| ttccggccaa ctgctggaat gacgttcaac ggcggggtcg ggccaaatgg gttgaccaag | 960 |
| aaacaggaaa tgctggtacg aagcgccatc aagtactggg tagagagaca caagcatatc | 1020 |
| gttagactcg taactgcaat tggagacgcc tatggtgtag ctttgctgct acatatgttg | 1080 |
| actactacta ttacgttaac tttgctcgct taccaagcaa caaagataca tgcagtagat | 1140 |
| acatacgcag catcagtagt aggttatttg ctatattctt taggacaagt ctttatgctc | 1200 |
| tgtatatttg gaaatcgtct cattgaagag agctcatcag tgatggaagc agcttattct | 1260 |
| tgtcactggt atgatggatc agaggaggcc aaaacatttg tacagattgt ttgccagcag | 1320 |
| tgtcagaaag cgatgtcgat ttcaggggca aagttcttca ctgtatcttt ggatctcttt | 1380 |
| gcttcggtgt tgggagctat ggttacctac ttcatggtgt tggtgcaact gaagtga | 1437 |

<210> SEQ ID NO 114
<211> LENGTH: 478
<212> TYPE: PRT
<213> ORGANISM: Artificial Sequence
<220> FEATURE:
<223> OTHER INFORMATION: synthetic

<400> SEQUENCE: 114

Met Gln Val Gln Pro Thr Lys Tyr Val Gly Leu Val Ala Asp Leu Met
1               5                   10                  15

Pro Asn Ile Arg Leu Met Gln Ala Ser Gly His Phe Leu Phe Arg Tyr

```
            20                  25                  30
Val Thr Gly Pro Ile Leu Ile Arg Lys Val Tyr Ser Trp Trp Thr Leu
         35                  40                  45
Ala Met Val Leu Ile Gln Phe Phe Ala Ile Leu Gly Asn Leu Ala Thr
 50                  55                  60
Asn Ala Asp Asp Val Asn Glu Leu Thr Ala Asn Thr Ile Thr Thr Leu
 65                  70                  75                  80
Phe Phe Thr His Ser Val Thr Lys Phe Ile Tyr Phe Ala Val Asn Ser
                 85                  90                  95
Glu Asn Phe Tyr Arg Thr Leu Ala Ile Trp Asn Gln Thr Asn Thr His
                100                 105                 110
Pro Leu Phe Ala Glu Ser Asp Ala Arg Tyr His Ser Ile Ala Leu Ala
                115                 120                 125
Lys Met Arg Lys Leu Leu Val Leu Val Met Ala Thr Thr Val Leu Ser
                130                 135                 140
Val Val Ala Trp Val Thr Ile Thr Phe Phe Gly Glu Ser Val Lys Thr
145                 150                 155                 160
Val Leu Asp Lys Ala Thr Asn Glu Thr Tyr Thr Val Asp Ile Pro Arg
                165                 170                 175
Leu Pro Ile Lys Ser Trp Tyr Pro Trp Asn Ala Met Ser Gly Pro Ala
                180                 185                 190
Tyr Ile Phe Ser Phe Ile Tyr Gln Ile Tyr Phe Leu Leu Phe Ser Met
                195                 200                 205
Val Gln Ser Asn Leu Ala Asp Val Met Phe Cys Ser Trp Leu Leu Leu
            210                 215                 220
Ala Cys Glu Gln Leu Gln His Leu Lys Asn Ile Met Lys Pro Leu Met
225                 230                 235                 240
Glu Phe Ser Ala Thr Leu Asp Thr Val Val Pro Asn Ser Gly Glu Leu
                245                 250                 255
Phe Lys Ala Gly Ser Ala Glu Gln Pro Lys Glu Gln Glu Pro Leu Pro
                260                 265                 270
Pro Val Thr Pro Pro Gln Gly Glu Asn Met Leu Asp Met Asp Leu Arg
                275                 280                 285
Gly Ile Tyr Ser Asn Arg Thr Asp Phe Thr Thr Thr Phe Arg Pro Thr
            290                 295                 300
Ala Gly Met Thr Phe Asn Gly Val Gly Pro Asn Gly Leu Thr Lys
305                 310                 315                 320
Lys Gln Glu Met Leu Val Arg Ser Ala Ile Lys Tyr Trp Val Glu Arg
                325                 330                 335
His Lys His Ile Val Arg Leu Val Thr Ala Ile Gly Asp Ala Tyr Gly
                340                 345                 350
Val Ala Leu Leu Leu His Met Leu Thr Thr Ile Thr Leu Thr Leu
            355                 360                 365
Leu Ala Tyr Gln Ala Thr Lys Ile His Ala Val Asp Thr Tyr Ala Ala
            370                 375                 380
Ser Val Val Gly Tyr Leu Leu Tyr Ser Leu Gly Gln Val Phe Met Leu
385                 390                 395                 400
Cys Ile Phe Gly Asn Arg Leu Ile Glu Glu Ser Ser Val Met Glu
                405                 410                 415
Ala Ala Tyr Ser Cys His Trp Tyr Asp Gly Ser Glu Glu Ala Lys Thr
                420                 425                 430
Phe Val Gln Ile Val Cys Gln Gln Cys Gln Lys Ala Met Ser Ile Ser
                435                 440                 445
```

Gly Ala Lys Phe Phe Thr Val Ser Leu Asp Leu Phe Ala Ser Val Leu
          450                 455                 460

Gly Ala Met Val Thr Tyr Phe Met Val Leu Val Gln Leu Lys
465                 470                 475

<210> SEQ ID NO 115
<211> LENGTH: 36
<212> TYPE: DNA
<213> ORGANISM: Artificial Sequence
<220> FEATURE:
<223> OTHER INFORMATION: synthetic

<400> SEQUENCE: 115
tggaattctg cagatcacca tgggaggtaa gttctc                                    36

<210> SEQ ID NO 116
<211> LENGTH: 33
<212> TYPE: DNA
<213> ORGANISM: Artificial Sequence
<220> FEATURE:
<223> OTHER INFORMATION: synthetic

<400> SEQUENCE: 116
gccactgtgc tggattcact tctgacttgg ttc                                       33

<210> SEQ ID NO 117
<211> LENGTH: 1176
<212> TYPE: DNA
<213> ORGANISM: Aedes aegypti

<400> SEQUENCE: 117
atgaacgacc tggtgaagtt tgagtccttc attcgggtgc cggagatatt cttcgacatg          60
atcggaatca cacgctacgg ggaagctcga gatacctgga aggctcgact caagcaggcg         120
ttcttctgga gttcatacgc caacacaatt ttctgtctga tcattgagca tatctacttc         180
atcaaagcgg cggggaactt cacgaacttt ttggaattga cggccttggc accgtgcatc         240
ggattcacgg cgctgtcgat agtcaaaatt atgacgatca agttgaacga agccaagttg         300
aacggaattc tcgatcggct tagtgactta ttcccgagga gtcacctcga tcaggatcga         360
tatcgaacgt acaactataa tctcgagtcg caaatggtga tgaagtcatt ctcgattctc         420
tacatgatct tgatttggat cttcaatctg cttccgttgg tatcgatgtt ggtgaactac         480
atttcgactg aatactgga aaaggagctt ccctacttca tgtggtattg gtatgattgg         540
cacaaggcag gttactacga gataacgttc ttccaccaga actggggagc cttcgattca         600
gctgtgttca acctcagcac ggatttactc ttttgtgcaa tcattcttct gatttgtttg         660
caatttgaca tattggcgta cagattgcga catgctaaag gtgattataa ggagttggaa         720
caatgtgtaa aactgcatca gtcagtcgtt gagttgagca accagctgga aggaatattc         780
tcaccttcca ttttggtcaa cttttgtcgga agctcggtaa taatctgtct ggtgggattc         840
caagctacgt ccaatatcag tgcattcgat tgttcaaat tcattctctt tctgatttca         900
tcgttagttc aagttttttct attgtgctac tacggaaaca aattgattga agcgagttca         960 caaataggg actgtgcctt cgaaggtaca tggtacatgg cagacttgcg ctaccaaaag        1020
tcgcttcttt tcgtgatgac tcgagctggc cagtggcaaa agctgacggc gatgaaattc        1080
tccgtagttt cgttggcaag ctattcggcg atcttaagta cgtcgttttc atacttcacc        1140
ttgctgaaga ccatctatga accaagtcag aagtga                                 1176

<210> SEQ ID NO 118
<211> LENGTH: 391
<212> TYPE: PRT
<213> ORGANISM: Aedes aegypti

<400> SEQUENCE: 118

```
Met Asn Asp Leu Val Lys Phe Glu Ser Phe Ile Arg Val Pro Glu Ile
1               5                   10                  15

Phe Phe Asp Met Ile Gly Ile Thr Arg Tyr Gly Glu Ala Arg Asp Thr
            20                  25                  30

Trp Lys Ala Arg Leu Lys Gln Ala Phe Phe Trp Ser Ser Tyr Ala Asn
        35                  40                  45

Thr Ile Phe Cys Leu Ile Ile Glu His Ile Tyr Phe Ile Lys Ala Ala
    50                  55                  60

Gly Asn Phe Thr Asn Phe Leu Glu Leu Thr Ala Leu Ala Pro Cys Ile
65                  70                  75                  80

Gly Phe Thr Ala Leu Ser Ile Val Lys Ile Met Thr Ile Lys Leu Asn
                85                  90                  95

Glu Ala Lys Leu Asn Gly Ile Leu Asp Arg Leu Ser Asp Leu Phe Pro
            100                 105                 110

Arg Ser His Leu Asp Gln Asp Arg Tyr Arg Thr Tyr Asn Tyr Asn Leu
        115                 120                 125

Glu Ser Gln Met Val Met Lys Ser Phe Ser Ile Leu Tyr Met Ile Leu
    130                 135                 140

Ile Trp Ile Phe Asn Leu Leu Pro Leu Val Ser Met Leu Val Asn Tyr
145                 150                 155                 160

Ile Ser Thr Gly Ile Leu Glu Lys Glu Leu Pro Tyr Phe Met Trp Tyr
                165                 170                 175

Trp Tyr Asp Trp His Lys Ala Gly Tyr Tyr Glu Ile Thr Phe Phe His
            180                 185                 190

Gln Asn Trp Gly Ala Phe Asp Ser Ala Val Phe Asn Leu Ser Thr Asp
        195                 200                 205

Leu Leu Phe Cys Ala Ile Ile Leu Leu Ile Cys Leu Gln Phe Asp Ile
    210                 215                 220

Leu Ala Tyr Arg Leu Arg His Ala Lys Gly Asp Tyr Lys Glu Leu Glu
225                 230                 235                 240

Gln Cys Val Lys Leu His Gln Ser Val Val Glu Leu Ser Asn Gln Leu
                245                 250                 255

Glu Gly Ile Phe Ser Pro Ser Ile Leu Val Asn Phe Val Gly Ser Ser
            260                 265                 270

Val Ile Ile Cys Leu Val Gly Phe Gln Ala Thr Ser Asn Ile Ser Ala
        275                 280                 285

Phe Asp Leu Phe Lys Phe Ile Leu Phe Leu Ile Ser Ser Leu Val Gln
    290                 295                 300

Val Phe Leu Leu Cys Tyr Tyr Gly Asn Lys Leu Ile Glu Ala Ser Ser
305                 310                 315                 320

Gln Ile Gly Tyr Cys Ala Phe Glu Gly Thr Trp Tyr Met Ala Asp Leu
                325                 330                 335

Arg Tyr Gln Lys Ser Leu Leu Phe Val Met Thr Arg Ala Gly Gln Trp
            340                 345                 350

Gln Lys Leu Thr Ala Met Lys Phe Ser Val Val Ser Leu Ala Ser Tyr
        355                 360                 365

Ser Ala Ile Leu Ser Thr Ser Phe Ser Tyr Phe Thr Leu Leu Lys Thr
    370                 375                 380
```

Ile Tyr Glu Pro Ser Gln Lys
385                 390

<210> SEQ ID NO 119
<211> LENGTH: 30
<212> TYPE: DNA
<213> ORGANISM: Artificial Sequence
<220> FEATURE:
<223> OTHER INFORMATION: synthetic

<400> SEQUENCE: 119
caccatggac agttttctgc aagtacagaa                                    30

<210> SEQ ID NO 120
<211> LENGTH: 30
<212> TYPE: DNA
<213> ORGANISM: Artificial Sequence
<220> FEATURE:
<223> OTHER INFORMATION: synthetic

<400> SEQUENCE: 120
ttaggagaat gatctcagca ttgtgatgta                                    30

<210> SEQ ID NO 121
<211> LENGTH: 1158
<212> TYPE: DNA
<213> ORGANISM: Drosophila melanogaster

<400> SEQUENCE: 121
atggacagtt ttctgcaagt acagaagagc accattgccc ttctgggctt tgatctcttt      60
agtgaaaatc gagaaatgtg gaaacgcccc tatagagcaa tgaatgtgtt tagcatagct     120
gccatttttc cctttatcct ggcagctgtg ctccataatt ggaagaatgt attgctgctg     180
gccgatgcca tggtggccct actaataacc attctgggcc tattcaagtt tagcatgata     240
ctttacttac gtcgcgattt caagcgactg attgacaaat ttcgtttgct catgtcgaat     300
gaggcggaac agggcgagga atacgccgag attctcaacg cagcaaacaa gcaggatcaa     360
cgaatgtgca ctctgtttag acttgtttc ctcctcgcct gggccttgaa tagtgttctg     420
cccctcgtga atgggtctc cagctattgg ttagcaggtc atgcagagcc cgagttgcct     480
tttcctgtc tttttccctg gaatatccac atcattcgca attatgtttt gagcttcatc     540
tggagcgctt tcgcctcgac aggtgtggtt ttacctgctg tcagcttgga taccatattc     600
tgttccttca ccagcaacct gtgcgccttc ttcaaaattg cgcagtacaa ggtggttaga     660
tttaagggcg atcccttaa agaatcacag gccacattga acaaagtctt tgccctgtac     720
cagaccagct tggatatgtg caacgatctg aatcagtgct accaaccgat tatctgcgcc     780
cagttcttca tttcatctct gcaactctgc atgctgggat atctgttctc cattactttt     840
gcccagacag agggcgtcta ctatgcctca ttcatagcca caatcattat acaagcctat     900
atctactgct actgcgggga gaacctgaag acgagagtg ccagcttcga gtgggccatc     960
tacgacagtc cgtggcacga gagtttgggt gctggtggag cctctacctc gatctgccga    1020
tccttgctga tcagcatgat gcgggctcat cggggattcc gcattacggg atactttttc    1080
gaggcaaaca tggaggcctt ctcatcgatt gttcgcacgg cgatgtccta catcacaatg    1140
ctgagatcat tctcctaa                                                  1158

<210> SEQ ID NO 122
<211> LENGTH: 385

```
<212> TYPE: PRT
<213> ORGANISM: Drosophila melanogaster

<400> SEQUENCE: 122

Met Asp Ser Phe Leu Gln Val Gln Lys Ser Thr Ile Ala Leu Leu Gly
1               5                   10                  15

Phe Asp Leu Phe Ser Glu Asn Arg Glu Met Trp Lys Arg Pro Tyr Arg
                20                  25                  30

Ala Met Asn Val Phe Ser Ile Ala Ala Ile Phe Pro Phe Ile Leu Ala
            35                  40                  45

Ala Val Leu His Asn Trp Lys Asn Val Leu Leu Ala Asp Ala Met
        50                  55                  60

Val Ala Leu Leu Ile Thr Ile Leu Gly Leu Phe Lys Phe Ser Met Ile
65                  70                  75                  80

Leu Tyr Leu Arg Arg Asp Phe Lys Arg Leu Ile Asp Lys Phe Arg Leu
                85                  90                  95

Leu Met Ser Asn Glu Ala Glu Gln Gly Glu Glu Tyr Ala Glu Ile Leu
                100                 105                 110

Asn Ala Ala Asn Lys Gln Asp Gln Arg Met Cys Thr Leu Phe Arg Thr
            115                 120                 125

Cys Phe Leu Leu Ala Trp Ala Leu Asn Ser Val Leu Pro Leu Val Arg
    130                 135                 140

Met Gly Leu Ser Tyr Trp Leu Ala Gly His Ala Glu Pro Glu Leu Pro
145                 150                 155                 160

Phe Pro Cys Leu Phe Pro Trp Asn Ile His Ile Ile Arg Asn Tyr Val
                165                 170                 175

Leu Ser Phe Ile Trp Ser Ala Phe Ala Ser Thr Gly Val Val Leu Pro
                180                 185                 190

Ala Val Ser Leu Asp Thr Ile Phe Cys Ser Phe Thr Ser Asn Leu Cys
            195                 200                 205

Ala Phe Phe Lys Ile Ala Gln Tyr Lys Val Val Arg Phe Lys Gly Gly
    210                 215                 220

Ser Leu Lys Glu Ser Gln Ala Thr Leu Asn Lys Val Phe Ala Leu Tyr
225                 230                 235                 240

Gln Thr Ser Leu Asp Met Cys Asn Asp Leu Asn Gln Cys Tyr Gln Pro
                245                 250                 255

Ile Ile Cys Ala Gln Phe Phe Ile Ser Ser Leu Gln Leu Cys Met Leu
            260                 265                 270

Gly Tyr Leu Phe Ser Ile Thr Phe Ala Gln Thr Glu Gly Val Tyr Tyr
    275                 280                 285

Ala Ser Phe Ile Ala Thr Ile Ile Gln Ala Tyr Ile Tyr Cys Tyr
290                 295                 300

Cys Gly Glu Asn Leu Lys Thr Glu Ser Ala Ser Phe Glu Trp Ala Ile
305                 310                 315                 320

Tyr Asp Ser Pro Trp His Glu Ser Leu Gly Ala Gly Gly Ala Ser Thr
                325                 330                 335

Ser Ile Cys Arg Ser Leu Leu Ile Ser Met Met Arg Ala His Arg Gly
            340                 345                 350

Phe Arg Ile Thr Gly Tyr Phe Phe Glu Ala Asn Met Glu Ala Phe Ser
    355                 360                 365

Ser Ile Val Arg Thr Ala Met Ser Tyr Ile Thr Met Leu Arg Ser Phe
    370                 375                 380

Ser
385
```

<210> SEQ ID NO 123
<211> LENGTH: 1206
<212> TYPE: DNA
<213> ORGANISM: Bombyx mori

<400> SEQUENCE: 123

| | | | | | | |
|---|---|---|---|---|---|---|
| atgaagctcc | tggagaagct | agaggacccc | gatcgtcctt | tactaggacc | aaacgtcaaa | 60 |
| gctttgaagt | tctggggggct | tctgttaccg | gaaagcagat | caaaaaagta | ttttacccta | 120 |
| tttatgcatt | tcgctgtgac | tgttttcact | gccactgaat | atatagacgt | atggtttgtt | 180 |
| aaatcagacc | tagctttgtt | attaaacaat | ctgaagataa | caatgttggc | gactgtaagc | 240 |
| gttttgaagg | ttaccacttt | tttgttgtgg | caaaatgcct | ggcgtgacct | cattggttac | 300 |
| gtatctcgag | ctgatttaga | gcaaagggcc | acttcggact | cgagaaagtt | ggctctgata | 360 |
| aacggattta | ccggctactg | ccgcaaaata | acgtattatt | actggttctt | gatgtatacg | 420 |
| accgtggcaa | ttgttacagt | acaaccaata | tttaagtttt | tttcatcagc | tgcctacaga | 480 |
| ctggacgtcc | aatctggaaa | cggtacatac | ctgcaagtag | taagttcctg | gataccgtgg | 540 |
| gataaaaata | ctttacccgg | atacctattg | gcctctattt | accagacata | cgcagccatt | 600 |
| tatggtggag | ctggatcac | gtccttcgac | accaatgcca | tagttataat | ggtatttttt | 660 |
| agagctgaat | tggaactatt | gaggattgat | tgtgctgctt | tatttgatga | tgaaaaatct | 720 |
| ttcggtgata | tggcttttat | gaggagattg | aaagagtgtc | atagaagaca | tacagaactt | 780 |
| gtcaaacatt | ctcggctgtt | cgattcttgt | tgtcgccga | taatgcttct | ctacatgttt | 840 |
| gtctgctcgg | taatgctttg | tgtgacggct | taccaaatta | caatagaaac | aaatccgatg | 900 |
| gaacggttcc | tcatgaccga | gtatttggtt | tcggcgtgg | cccagctatt | catgtactgt | 960 |
| tggcacagta | atgatgttct | ctatgcgagt | caggatctat | ccagaggtcc | ttacgagagt | 1020 |
| gcctggtggt | cgagagatgt | gaagtaccgc | aaaaatttat | atatattggt | ggcgcagttt | 1080 |
| aacaaggtta | ttgtctttc | cgcgggcccc | ttcactaagc | ttacggtcgc | cacttttatc | 1140 |
| aggatcctca | aaggagccta | tagttactac | acactgctca | gtcagtcgca | atgaataaa | 1200 |
| acatga | | | | | | 1206 |

<210> SEQ ID NO 124
<211> LENGTH: 41
<212> TYPE: DNA
<213> ORGANISM: Artificial Sequence
<220> FEATURE:
<223> OTHER INFORMATION: synthetic

<400> SEQUENCE: 124
tggaattctg cagatcacca tgaagctcct ggagaagcta g          41

<210> SEQ ID NO 125
<211> LENGTH: 41
<212> TYPE: DNA
<213> ORGANISM: Artificial Sequence
<220> FEATURE:
<223> OTHER INFORMATION: synthetic

<400> SEQUENCE: 125
gccactgtgc tggattcatg ttttattcat tgcgactga c           41

<210> SEQ ID NO 126
<211> LENGTH: 401
<212> TYPE: PRT

-continued

<213> ORGANISM: Bombyx mori

<400> SEQUENCE: 126

```
Met Lys Leu Leu Glu Lys Leu Glu Asp Pro Asp Arg Pro Leu Leu Gly
1               5                   10                  15

Pro Asn Val Lys Ala Leu Lys Phe Trp Gly Leu Leu Pro Glu Ser
            20                  25                  30      Ser

Arg Ser Lys Lys Tyr Phe Tyr Leu Phe Met His Phe Ala Val Thr Val
            35                  40                  45

Phe Thr Ala Thr Glu Tyr Ile Asp Val Trp Phe Val Lys Ser Asp Leu
        50                  55                  60

Ala Leu Leu Leu Asn Asn Leu Lys Ile Thr Met Leu Ala Thr Val Ser
65                  70                  75                  80

Val Leu Lys Val Thr Thr Phe Leu Leu Trp Gln Asn Ala Trp Arg Asp
                85                  90                  95

Leu Ile Gly Tyr Val Ser Arg Ala Asp Leu Glu Gln Arg Ala Thr Ser
            100                 105                 110

Asp Ser Arg Lys Leu Ala Leu Ile Asn Gly Phe Thr Gly Tyr Cys Arg
        115                 120                 125

Lys Ile Thr Tyr Tyr Tyr Trp Phe Leu Met Tyr Thr Thr Val Ala Ile
    130                 135                 140

Val Thr Val Gln Pro Ile Phe Lys Phe Phe Ser Ser Ala Ala Tyr Arg
145                 150                 155                 160

Leu Asp Val Gln Ser Gly Asn Gly Thr Tyr Leu Gln Val Val Ser Ser
                165                 170                 175

Trp Ile Pro Trp Asp Lys Asn Thr Leu Pro Gly Tyr Leu Leu Ala Ser
            180                 185                 190

Ile Tyr Gln Thr Tyr Ala Ala Ile Tyr Gly Gly Gly Trp Ile Thr Ser
        195                 200                 205

Phe Asp Thr Asn Ala Ile Val Ile Met Val Phe Phe Arg Ala Glu Leu
    210                 215                 220

Glu Leu Leu Arg Ile Asp Cys Ala Ala Leu Phe Asp Asp Glu Lys Ser
225                 230                 235                 240

Phe Gly Asp Met Ala Phe Met Arg Arg Leu Lys Glu Cys His Arg Arg
                245                 250                 255

His Thr Glu Leu Val Lys His Ser Arg Leu Phe Asp Ser Cys Leu Ser
            260                 265                 270

Pro Ile Met Leu Leu Tyr Met Phe Val Cys Ser Val Met Leu Cys Val
        275                 280                 285

Thr Ala Tyr Gln Ile Thr Ile Glu Thr Asn Pro Met Glu Arg Phe Leu
    290                 295                 300

Met Thr Glu Tyr Leu Val Phe Gly Val Ala Gln Leu Phe Met Tyr Cys
305                 310                 315                 320

Trp His Ser Asn Asp Val Leu Tyr Ala Ser Gln Asp Leu Ser Arg Gly
                325                 330                 335

Pro Tyr Glu Ser Ala Trp Trp Ser Arg Asp Val Lys Tyr Arg Lys Asn
            340                 345                 350

Leu Tyr Ile Leu Val Ala Gln Phe Asn Lys Val Ile Val Phe Ser Ala
        355                 360                 365

Gly Pro Phe Thr Lys Leu Thr Val Ala Thr Phe Ile Arg Ile Leu Lys
    370                 375                 380

Gly Ala Tyr Ser Tyr Tyr Thr Leu Leu Ser Gln Ser Gln Met Asn Lys
385                 390                 395                 400
```

Thr

<210> SEQ ID NO 127
<211> LENGTH: 591
<212> TYPE: DNA
<213> ORGANISM: Aequorea victoria

<400> SEQUENCE: 127

| | | | | |
|---|---|---|---|---|
| atgacaagca | aacaatactc | agtcaagctt | acatcagact | tcgacaaccc aagatggatt | 60 |
| ggacgacaca | agcatatgtt | caatttcctt | gatgtcaacc | acaatggaaa aatctctctt | 120 |
| gacgagatgg | tctacaaggc | atctgatatt | gtcatcaata | accttggagc aacacctgag | 180 |
| caagccaaac | gacacaaaga | tgctgtagaa | gccttcttcg | gaggagctgg aatgaaatat | 240 |
| ggtgtggaaa | ctgattggcc | tgcatatatt | gaaggatgga | aaaaattggc tactgatgaa | 300 |
| ttggagaaat | acgccaaaaa | cgaaccaacg | ctcatccgta | tgggggtgaa tgctttgttt | 360 |
| gatatcgttg | acaaagatca | aaatggagcc | attacactgg | atgaatggaa agcatacacc | 420 |
| aaagctgctg | gtatcatcca | atcatcagaa | gattgcgagg | aaacattcag agtgtgcgat | 480 |
| attgatgaaa | gtggacaact | cgatgttgat | gagatgacaa | gacaacattt aggattttgg | 540 |
| tacaccatgg | atcctgcttg | cgaaaagctc | tacggtggag | ctgtccccta a | 591 |

<210> SEQ ID NO 128
<211> LENGTH: 24
<212> TYPE: DNA
<213> ORGANISM: Artificial Sequence
<220> FEATURE:
<223> OTHER INFORMATION: synthetic

<400> SEQUENCE: 128
caccatgaca agcaaacaat actc        24

<210> SEQ ID NO 129
<211> LENGTH: 22
<212> TYPE: DNA
<213> ORGANISM: Artificial Sequence
<220> FEATURE:
<223> OTHER INFORMATION: synthetic

<400> SEQUENCE: 129 ttagggggaca gctccaccgt ag        22

<210> SEQ ID NO 130
<211> LENGTH: 196
<212> TYPE: PRT
<213> ORGANISM: Aequorea victoria

<400> SEQUENCE: 130

Met Thr Ser Lys Gln Tyr Ser Val Lys Leu Thr Ser Asp Phe Asp Asn
 1               5                  10                  15

Pro Arg Trp Ile Gly Arg His Lys His Met Phe Asn Phe Leu Asp Val
            20                  25                  30

Asn His Asn Gly Lys Ile Ser Leu Asp Glu Met Val Tyr Lys Ala Ser
        35                  40                  45

Asp Ile Val Ile Asn Asn Leu Gly Ala Thr Pro Glu Gln Ala Lys Arg
    50                  55                  60

His Lys Asp Ala Val Glu Ala Phe Phe Gly Gly Ala Gly Met Lys Tyr
65                  70                  75                  80

Gly Val Glu Thr Asp Trp Pro Ala Tyr Ile Glu Gly Trp Lys Lys Leu
                85                  90                  95

Ala Thr Asp Glu Leu Glu Lys Tyr Ala Lys Asn Glu Pro Thr Leu Ile
            100                 105                 110

Arg Ile Trp Gly Asp Ala Leu Phe Asp Ile Val Asp Lys Asp Gln Asn
        115                 120                 125

Gly Ala Ile Thr Leu Asp Glu Trp Lys Ala Tyr Thr Lys Ala Ala Gly
130                 135                 140

Ile Ile Gln Ser Ser Glu Asp Cys Glu Glu Thr Phe Arg Val Cys Asp
145                 150                 155                 160

Ile Asp Glu Ser Gly Gln Leu Asp Val Asp Glu Met Thr Arg Gln His
                165                 170                 175

Leu Gly Phe Trp Tyr Thr Met Asp Pro Ala Cys Glu Lys Leu Tyr Gly
            180                 185                 190

Gly Ala Val Pro
        195

<210> SEQ ID NO 131
<211> LENGTH: 42
<212> TYPE: DNA
<213> ORGANISM: Artificial Sequence
<220> FEATURE:
<223> OTHER INFORMATION: synthetic

<400> SEQUENCE: 131
gtggcggccg ctcgaggcca ccatgacaag caaacaatac tc        42

<210> SEQ ID NO 132
<211> LENGTH: 38
<212> TYPE: DNA
<213> ORGANISM: Artificial Sequence
<220> FEATURE:
<223> OTHER INFORMATION: synthetic

<400> SEQUENCE: 132
gccctctaga ctcgagttag gggacagctc caccgtag        38

<210> SEQ ID NO 133
<211> LENGTH: 42
<212> TYPE: DNA
<213> ORGANISM: Artificial Sequence
<220> FEATURE:
<223> OTHER INFORMATION: synthetic

<400> SEQUENCE: 133
gtggcggccg ctcgaggcca ccatgacaag caaacaatac tc        42

<210> SEQ ID NO 134
<211> LENGTH: 38
<212> TYPE: DNA
<213> ORGANISM: Artificial Sequence
<220> FEATURE:
<223> OTHER INFORMATION: synthetic

<400> SEQUENCE: 134
gccctctaga ctcgagttag gggacagctc caccgtag        38

<210> SEQ ID NO 135
<211> LENGTH: 232
<212> TYPE: PRT
<213> ORGANISM: Aedes aegypti

<400> SEQUENCE: 135

Met Asn Val Gln Pro Thr Lys Tyr His Gly Leu Val Leu Asp Leu Met

```
  1               5                  10                 15
Pro Asn Ile Arg Leu Met Gln Gly Phe Gly His Phe Leu Phe Arg Tyr
                20                 25                 30
Val Asn Gly Pro Val Leu Ile Arg Lys Leu Tyr Ser Trp Trp Asn Leu
                35                 40                 45
Ile Met Ile Leu Leu Gln Tyr Phe Ala Ile Met Gly Asn Leu Val Met
                50                 55                 60
Asn Thr Gly Asp Val Asn Glu Leu Thr Ala Asn Thr Ile Thr Thr Leu
 65                 70                 75                 80
Phe Phe Thr His Ser Val Thr Lys Phe Ile Tyr Val Ala Val Asn Ser
                85                 90                 95
Glu His Phe Tyr Arg Thr Leu Gly Ile Trp Asn Gln Pro Asn Ser His
                100                105                110
Ser Leu Phe Ala Glu Ser Asp Ala Arg Tyr His Ser Ile Ala Leu Ala
                115                120                125
Lys Met Arg Lys Leu Leu Val Met Val Met Val Thr Thr Val Leu Ser
                130                135                140
Val Val Ala Trp Ile Thr Ile Thr Phe Phe Gly Asp Ser Val Lys Asn
145                150                155                160
Val Phe Asp Lys Glu Thr Asn Glu Thr Tyr Thr Val Glu Ile Pro Arg
                165                170                175
Leu Pro Ile Lys Ala Trp Tyr Pro Trp Asp Ala Met Ser Gly Val Pro
                180                185                190
Tyr Phe Phe Ser Phe Ile Tyr Gln Ala Tyr Phe Leu Leu Phe Ser Met
                195                200                205
Cys Gln Ala Asn Leu Ala Asp Val Met Phe Cys Ser Trp Leu Leu Phe
                210                215                220
Thr Cys Glu Gln Leu Gln His Leu
225                230
```

<210> SEQ ID NO 136
<211> LENGTH: 232
<212> TYPE: PRT
<213> ORGANISM: Anopheles gambiae

<400> SEQUENCE: 136

```
Met Gln Val Gln Pro Thr Lys Tyr Val Gly Leu Val Ala Asp Leu Met
 1               5                  10                 15
Pro Asn Ile Arg Leu Met Gln Ala Ser Gly His Phe Leu Phe Arg Tyr
                20                 25                 30
Val Thr Gly Pro Ile Leu Ile Arg Lys Val Tyr Ser Trp Trp Thr Leu
                35                 40                 45
Ala Met Val Leu Ile Gln Phe Phe Ala Ile Leu Gly Asn Leu Ala Thr
                50                 55                 60
Asn Ala Asp Asp Val Asn Glu Leu Thr Ala Asn Thr Ile Thr Thr Leu
 65                 70                 75                 80
Phe Phe Thr His Ser Val Thr Lys Phe Ile Tyr Phe Ala Val Asn Ser
                85                 90                 95
Glu Asn Phe Tyr Arg Thr Leu Ala Ile Trp Asn Gln Thr Asn Thr His
                100                105                110
Pro Leu Phe Ala Glu Ser Asp Ala Arg Tyr His Ser Ile Ala Leu Ala
                115                120                125
Lys Met Arg Lys Leu Leu Val Leu Val Met Ala Thr Thr Val Leu Ser
                130                135                140
```

```
Val Val Ala Trp Val Thr Ile Thr Phe Phe Gly Glu Ser Val Lys Thr
145                 150                 155                 160

Val Leu Asp Lys Ala Thr Asn Glu Thr Tyr Thr Val Asp Ile Pro Arg
                165                 170                 175

Leu Pro Ile Lys Ser Trp Tyr Pro Trp Asn Ala Met Ser Gly Pro Ala
                180                 185                 190

Tyr Ile Phe Ser Phe Ile Tyr Gln Ile Tyr Phe Leu Leu Phe Ser Met
                195                 200                 205

Val Gln Ser Asn Leu Ala Asp Val Met Phe Cys Ser Trp Leu Leu Leu
                210                 215                 220

Ala Cys Glu Gln Leu Gln His Leu
225                 230
```

<210> SEQ ID NO 137
<211> LENGTH: 246
<212> TYPE: PRT
<213> ORGANISM: Aedes aegypti

<400> SEQUENCE: 137

```
Lys Gly Ile Met Arg Pro Leu Met Glu Leu Ser Ala Thr Leu Asp Thr
1               5                   10                  15

Tyr Arg Pro Asn Ser Ala Ala Leu Phe Arg Val Ala Ser Ala Gly Ser
                20                  25                  30

Lys Ser Glu Leu Ile Leu Asn Glu Glu Lys Asp Pro Asp Thr Lys Asp
            35                  40                  45

Phe Asp Leu Asn Gly Ile Tyr Asn Ser Lys Ala Asp Trp Gly Ala Gln
50                  55                  60

Phe Arg Ala Pro Ser Thr Leu Gln Thr Phe Gly Asp Asn Gly Ile Asn
65                  70                  75                  80

Gly Asn Pro Asn Gly Leu Thr Lys Lys Gln Glu Leu Met Val Arg Ser
                85                  90                  95

Ala Ile Lys Tyr Trp Val Glu Arg His Lys His Val Val Arg Leu Val
                100                 105                 110

Ser Ala Ile Gly Glu Thr Tyr Gly Ala Ala Leu Leu Leu His Met Leu
            115                 120                 125

Thr Ser Thr Ile Lys Leu Thr Leu Leu Ala Tyr Gln Ala Thr Lys Ile
130                 135                 140

Asp Ala Leu Asn Val Tyr Gly Leu Thr Val Ile Gly Tyr Leu Val Tyr
145                 150                 155                 160

Ala Leu Ala Gln Val Phe Leu Phe Cys Ile Phe Gly Asn Arg Leu Ile
                165                 170                 175

Glu Glu Ser Ser Ser Val Met Glu Ala Ala Tyr Ser Cys His Trp Tyr
                180                 185                 190

Asp Gly Ser Glu Glu Ala Lys Thr Phe Val Gln Ile Val Cys Gln Gln
                195                 200                 205

Cys Gln Lys Ala Met Thr Ile Ser Gly Ala Lys Phe Phe Thr Val Ser
210                 215                 220

Leu Asp Leu Phe Ala Ser Val Leu Gly Ala Val Val Thr Tyr Phe Met
225                 230                 235                 240

Val Leu Val Gln Leu Lys
                245
```